United States Patent
Shelton, IV et al.

(10) Patent No.: US 11,160,602 B2
(45) Date of Patent: Nov. 2, 2021

(54) CONTROL OF SURGICAL FIELD IRRIGATION

(71) Applicant: Ethicon LLC, Guaynabo, PR (US)

(72) Inventors: Frederick E. Shelton, IV, Hillsboro, OH (US); David C. Yates, West Chester, OH (US); Heather Doak, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 479 days.

(21) Appl. No.: 15/689,853

(22) Filed: Aug. 29, 2017

(65) Prior Publication Data

US 2019/0059980 A1    Feb. 28, 2019

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61M 1/802* (2021.05); *A61B 18/1482* (2013.01); *A61B 34/30* (2016.02); *A61B 2018/0063* (2013.01); *A61B 2018/00208* (2013.01); *A61B 2018/00404* (2013.01);
(Continued)

(58) Field of Classification Search
CPC .............. A61B 34/30; A61B 2034/301; A61B 2034/302; A61B 2034/303; A61B 18/14
See application file for complete search history.

(56) References Cited

U.S. PATENT DOCUMENTS

| 5,322,055 A | 6/1994 | Davison et al. |
| 5,403,276 A * | 4/1995 | Schechter ........ A61B 17/32002 604/118 |

(Continued)

FOREIGN PATENT DOCUMENTS

| WO | WO-2014151621 A1 | 9/2014 |
| WO | WO-2014151952 A1 | 9/2014 |

OTHER PUBLICATIONS

U.S. Appl. No. 15/200,283 entitled "Methods, Systems, And Devices For Initializing A Surgical Tool" filed Jul. 1, 2016.
(Continued)

*Primary Examiner* — Michael F Peffley
*Assistant Examiner* — Bo Ouyang
(74) *Attorney, Agent, or Firm* — Mintz Levin Cohn Ferris Glovsky and Popeo, P.C.

(57) ABSTRACT

A surgical system includes an electrosurgical tool configured to be releasably coupled to a surgical robotic system having a control system. The tool has a shaft having an end effector with treatment electrodes configured to apply electrosurgical power to a tissue, and aspiration and irrigation tubes having ports in the vicinity of the electrodes. The control system can control a flow rate of an irrigation fluid based on deviation of power delivered by the electrodes to the tissue from a power set point, or based on an aspiration rate that is controlled based on tissue impedance. The tool can have first and second ports and a conduit configured to selectively provide or aspirate fluids through at least one of the ports. At least one of a flow rate and an aspiration rate are controlled by the control system based on a rotational angle of the shaft relative to a ground.

20 Claims, 22 Drawing Sheets

(51) Int. Cl.
*A61M 1/00* (2006.01)
*A61B 18/00* (2006.01)
*A61M 3/02* (2006.01)
*A61B 34/30* (2016.01)
*A61B 90/00* (2016.01)

(52) U.S. Cl.
CPC ............ *A61B 2018/00595* (2013.01); *A61B 2018/00642* (2013.01); *A61B 2018/00666* (2013.01); *A61B 2018/00744* (2013.01); *A61B 2018/00875* (2013.01); *A61B 2018/126* (2013.01); *A61B 2090/061* (2016.02); *A61B 2090/064* (2016.02); *A61B 2090/066* (2016.02); *A61B 2218/002* (2013.01); *A61B 2218/007* (2013.01); *A61M 1/0058* (2013.01); *A61M 3/022* (2014.02); *A61M 3/0254* (2013.01); *A61M 2205/364* (2013.01)

(56) References Cited

U.S. PATENT DOCUMENTS

| | | |
|---|---|---|
| 5,558,671 A | 9/1996 | Yates |
| 5,681,276 A * | 10/1997 | Lundquist .......... A61B 18/1477 604/22 |
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,039,735 A | 3/2000 | Greep |
| 6,066,137 A | 5/2000 | Greep |
| 6,132,368 A | 10/2000 | Cooper |
| 6,168,605 B1 | 1/2001 | Measamer et al. |
| 6,231,565 B1 | 5/2001 | Tovey et al. |
| 6,325,811 B1 | 12/2001 | Messerly |
| 6,364,888 B1 | 4/2002 | Niemeyer et al. |
| 6,500,176 B1 | 12/2002 | Truckai et al. |
| 6,635,034 B1 * | 10/2003 | Cosmescu .............. A61B 18/14 601/35 |
| 6,736,810 B2 | 5/2004 | Hoey et al. |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV |
| 7,524,320 B2 | 4/2009 | Tierney et al. |
| 7,549,564 B2 | 6/2009 | Boudreaux |
| 7,559,450 B2 | 7/2009 | Wales et al. |
| 7,654,431 B2 | 2/2010 | Hueil et al. |
| 7,691,098 B2 | 4/2010 | Wallace et al. |
| 7,780,054 B2 | 8/2010 | Wales |
| 7,784,662 B2 | 8/2010 | Wales et al. |
| 7,798,386 B2 | 9/2010 | Schall et al. |
| 7,806,891 B2 | 10/2010 | Nowlin et al. |
| 7,824,401 B2 | 11/2010 | Manzo et al. |
| 8,439,910 B2 | 5/2013 | Greep et al. |
| 8,461,744 B2 | 6/2013 | Wiener et al. |
| 8,469,252 B2 | 6/2013 | Holcomb et al. |
| 8,602,286 B2 | 12/2013 | Crainich et al. |
| 8,684,253 B2 | 4/2014 | Giordano et al. |
| 8,771,270 B2 | 7/2014 | Burbank |
| 8,986,302 B2 | 3/2015 | Aldridge et al. |
| 9,023,071 B2 | 5/2015 | Miller et al. |
| 9,072,536 B2 | 7/2015 | Shelton, IV et al. |
| 9,095,367 B2 | 8/2015 | Olson et al. |
| 9,119,657 B2 | 9/2015 | Shelton, IV et al. |
| 9,168,092 B2 | 10/2015 | Horner et al. |
| 9,393,037 B2 | 7/2016 | Olson et al. |
| 9,445,816 B2 | 9/2016 | Swayze et al. |
| 9,585,658 B2 | 3/2017 | Shelton, IV |
| 9,713,468 B2 | 7/2017 | Harris et al. |
| 9,713,471 B2 | 7/2017 | Holcomb et al. |
| 10,675,082 B2 | 6/2020 | Shelton, IV et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2010/0191282 A1 | 7/2010 | Harris et al. |
| 2010/0198248 A1 | 8/2010 | Vakharia |
| 2011/0015631 A1 | 1/2011 | Wiener et al. |
| 2011/0087218 A1 | 4/2011 | Boudreaux et al. |
| 2011/0087256 A1 | 4/2011 | Wiener et al. |
| 2012/0078139 A1 | 3/2012 | Aldridge et al. |
| 2012/0078243 A1 | 3/2012 | Worrell et al. |
| 2012/0078247 A1 | 3/2012 | Worrell et al. |
| 2012/0116379 A1 | 5/2012 | Yates et al. |
| 2012/0165809 A1 * | 6/2012 | Christian ............ A61B 18/1492 606/41 |
| 2012/0292367 A1 | 11/2012 | Morgan et al. |
| 2013/0012957 A1 | 1/2013 | Shelton, IV et al. |
| 2013/0023868 A1 | 1/2013 | Worrell et al. |
| 2013/0030385 A1 * | 1/2013 | Schultz ............... A61B 18/1492 604/247 |
| 2013/0030428 A1 | 1/2013 | Worrell et al. |
| 2013/0261648 A1 | 10/2013 | Laurent et al. |
| 2013/0325034 A1 | 12/2013 | Schena et al. |
| 2014/0005718 A1 | 1/2014 | Shelton, IV et al. |
| 2014/0151952 A1 | 6/2014 | Kozaki |
| 2014/0166728 A1 | 6/2014 | Swayze et al. |
| 2014/0171970 A1 | 6/2014 | Martin et al. |
| 2014/0246474 A1 * | 9/2014 | Hall ................. A61B 17/07207 227/175.1 |
| 2014/0257269 A1 * | 9/2014 | Woloszko ............ A61B 18/148 606/34 |
| 2014/0263541 A1 | 9/2014 | Leimbach et al. |
| 2014/0276757 A1 | 9/2014 | Ellman |
| 2014/0276931 A1 | 9/2014 | Parihar et al. |
| 2015/0209059 A1 | 7/2015 | Trees et al. |
| 2015/0209573 A1 | 7/2015 | Hibner et al. |
| 2015/0272575 A1 * | 10/2015 | Leimbach ............ A61B 17/072 227/175.3 |
| 2015/0282825 A1 | 10/2015 | Trees et al. |
| 2015/0335376 A1 * | 11/2015 | Hufnagel ............ A61B 18/1402 606/39 |
| 2015/0365296 A1 | 12/2015 | Bunte et al. |
| 2016/0019918 A1 | 1/2016 | Juman |
| 2016/0019919 A1 | 1/2016 | Gale et al. |
| 2016/0089533 A1 | 3/2016 | Turner et al. |
| 2016/0128767 A1 * | 5/2016 | Azamian ............ A61B 18/1492 606/41 |
| 2016/0175060 A1 | 6/2016 | Park |
| 2016/0242844 A1 * | 8/2016 | Orczy-Timko .... A61B 18/1492 |
| 2016/0287252 A1 | 10/2016 | Parihar |
| 2016/0367243 A1 | 12/2016 | Martin et al. |
| 2017/0056038 A1 | 3/2017 | Hess et al. |
| 2017/0196637 A1 | 7/2017 | Shelton, IV et al. |
| 2017/0202609 A1 | 7/2017 | Shelton, IV et al. |
| 2018/0116751 A1 | 5/2018 | Schwartz et al. |
| 2019/0059929 A1 | 2/2019 | Shelton, IV et al. |

OTHER PUBLICATIONS

U.S. Appl. No. 15/237,653 entitled "Methods, Systems, And Devices For Controlling A Motor Of A Robotic Surgical System" filed Aug. 16, 2016.

U.S. Appl. No. 15/422,767 entitled "Robotic Surgical System and Methods for Articulation Calibration" filed Feb. 2, 2017.

U.S. Appl. No. 15/634,620 entitled "Surgical Stapler with Independently Actuated Drivers to Provide Varying Staple Heights" filed Jun. 27, 2017.

(56) References Cited

OTHER PUBLICATIONS

U.S. Appl. No. 15/674,075 entitled "Clip Retention for Surgical Clip Applier" filed Aug. 10, 2017.
U.S. Appl. No. 15/674,086 entitled "Surgical Clip Applier Jaw Alignment" filed Aug. 10, 2017.
U.S. Appl. No. 15/674,096 entitled "Surgical Device with Overload Mechanism" filed Aug. 10, 2017.
U.S. Appl. No. 15/674,121 entitled "Jaw for Clip Applier" filed Aug. 10, 2017.
U.S. Appl. No. 15/674,125 entitled "Clip Appliers with Extended Jaw Tip" filed Aug. 10, 2017.
U.S. Appl. No. 15/674,166 entitled "Surgical Clip Applier" filed Aug. 10, 2017.
U.S. Appl. No. 15/689,072 entitled "Methods, Systems, and Devices for Controlling Electrosurgical Tools" filed Aug. 29, 2017.
U.S. Appl. No. 29/613,511 entitled "Clip Applier Rotation Knob" filed Aug. 10, 2017.

* cited by examiner

CONTROL OF SURGICAL FIELD IRRIGATION

FIELD

Surgical devices and methods are provided for controlling irrigation of a surgical field by an electrosurgical tool.

BACKGROUND

More and more surgical procedures are being performed using electrically-powered surgical devices that are either hand-held or that are coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

A common concern with electrically-powered surgical devices is the lack of control and tactile feedback that is inherent to a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a cutting and/or sealing operation (e.g., an actuation button or switch is typically binary and provides no feedback on how much tissue has been cut, etc.) or the forces being encountered (e.g., toughness of the tissue). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue.

In addition, electrically-powered devices can be less precise in operation than manually-operated devices. For example, users of manually-operated devices are able to instantly stop the progress of a mechanism by simply releasing the actuation mechanism. With an electrically-powered device, however, releasing an actuation button or switch may not result in instantaneous halting of a mechanism, as the electric motor may continue to drive the mechanism until the kinetic energy of its moving components is dissipated. As a result, a mechanism may continue to advance for some amount of time even after a user releases an actuation button.

Accordingly, there remains a need for improved devices and methods that address current issues with electrically-powered surgical devices.

SUMMARY

In one aspect, a surgical system is provided that in some embodiments includes a surgical tool and a plurality of motors. The surgical tool includes a shaft having an end effector at a distal end thereof and at least one treatment electrode associated with the end effector, an aspiration tube extending through the shaft and having an inlet port at a distal end thereof, and an irrigation tube extending through the shaft and having an outlet port in proximity to the at least one electrode, the irrigation tube being in fluid communication with a fluid source. The surgical tool also includes a housing operably connected to the shaft, the housing having a pump in fluid communication with the irrigation tube, the pump having at least one first rotatable element configured to be selectively driven to actuate the pump. The plurality of motors are configured to be operably connected to the housing, and a first motor of the motors is configured to selectively drive the first rotatable element of the pump to control a flow rate of a fluid delivered through the irrigation tube.

The surgical system can vary in many various ways. For example, the aspiration tube can be extendible and retractable, and the housing can further include a second rotatable element configured to be selectively driven by a second motor of the motors to control extension and retraction of the aspiration tube. As another example, the at least one electrode can be two electrodes configured to apply radiofrequency (RF) energy to tissue. As a further example, the housing can further have a third rotatable element configured to be selectively driven to cause articulation of the end effector with respect to the shaft, and the housing further has a fourth rotatable element configured to be selectively driven to cause rotation of the shaft about a longitudinal axis thereof.

In some embodiments, the surgical system is a surgical robotic system having a tool driver assembly configured to operably mate with the housing, and the surgical robotic system is associated with a control system. The surgical system can include an electrosurgical generator configured to provide electrosurgical energy to the at least one electrode and configured to be controlled by the control system.

The control system can have various configurations and it can include various controllers. In some embodiments, the control system includes a proportional-integral-derivative (PID) controller that is configured to output a current control value to the first motor based on a difference between a flow rate set point and an actual flow rate, wherein the actual flow rate is determined based on monitored tissue impedance and the flow rate set point is determined based on a power set point. The PID module can be configured to output the current control value to the first motor such that the flow rate of the fluid increases when the tissue impedance increases. The flow rate set point can be determined based on desired power to be applied by the at least one electrode to a tissue to cause a desired effect on the tissue.

In some embodiments, the surgical system further includes a vacuum source in fluid communication with the aspiration tube and controlled by a fifth motor of the motors. In such embodiments, the control system is configured to control the fifth motor to selectively drive the vacuum source to adjust, based on measured tissue impedance, an aspiration rate of fluid aspirated through the aspiration tube, and control the first motor to selectively drive the first rotatable element to actuate the pump to adjust the flow rate of the fluid based on the aspiration rate. The control system can be configured to control the fifth motor such that the vacuum source increases the aspiration rate as the impedance increases, and pump increases the flow rate of the fluid such that an increase in the flow rate occurs with a predetermined delay and proportionate to an increase in the aspiration rate.

In some embodiments, the control system associated with the surgical robotic system is configured to control power provided by an electrosurgical generator to the at least one electrode, based on a tilting angle of the at least one electrode with respect to a gravity vector. The control system can be configured to increase the power when the tilting angle exceeds a predetermined value.

In another aspect, a surgical system is provided that in some embodiments includes an electromechanical device including an instrument shaft and an end effector formed at a distal end thereof and first and second treatment electrodes associated with the end effector, an aspiration tube extending through the shaft and having an inlet port in proximity to the electrodes, the aspiration tube being in fluid communication with a vacuum source, an irrigation tube extending through the shaft and having an outlet port in proximity to the electrodes, the irrigation tube being in fluid communication with a fluid source, and a housing coupled proximally to the shaft, the housing comprising a pump operably coupled to the irrigation tube, the housing being configured to operably connect to a tool drive assembly of a robotic surgical system. The surgical system also includes a control system configured to control a flow rate of a fluid delivered through the outlet port of the irrigation tube based on power received by the electrodes.

The control system of the surgical system can vary in many ways. For example, in some embodiments, the control system can be configured to control the flow rate by controlling an aspiration rate of fluid aspirated through the inlet port of the aspiration tube based on the power, and by controlling the flow rate based on the controlled aspiration rate. As another example, in some embodiments, the control system is configured to control the flow rate based monitoring a deviation of the power from a power set point.

In another aspect, a method of treating tissue is provided that in some embodiments includes actuating a power generator to deliver power to a tissue at a treatment site through first and second electrodes of an electrosurgical tool operably coupled to the power generator, monitoring impedance of the tissue as the electrical energy is applied to the tissue to determine a deviation of actual power from a power set point, and controlling a flow rate of a fluid provided to the treatment site by an irrigation tube in fluid communication with a pump, the flow rate being controlled based on the monitored impedance.

The method can vary in many ways. For example, the method can further include controlling the flow rate of the irrigation fluid when it is determined that the electrodes are in contact with the tissue. As another example, the method can further include controlling the power generator to cease power delivery through the electrodes when the monitored impedance exceeds a predetermined impedance maximum, and to resume power delivery if the monitored impedance remains above the predetermined impedance maximum for a predetermined time period.

In some embodiments, the method further includes controlling an aspiration rate of a fluid aspirated from the treatment site in proximity to the electrodes such that the aspiration rate is increased in response to an increase in the monitored impedance, and further controlling the flow rate such that the flow rate increases proportionate to an increase in the aspiration rate.

In another aspect, a surgical system is provided that, in some embodiments, includes an electrosurgical device, at least one conduit, and a control system. The electrosurgical device includes an instrument shaft and an end effector formed at a distal end thereof, and the end effector has first and second electrodes that are opposed to each other and first and second fluid ports adjacent to the first and second electrodes. The at least one conduit is configured to selectively communicate an irrigation fluid between a fluid source and at least one of the first and second fluid ports. The control system is configured to monitor a rotational angle of the shaft relative to a ground and to increase a flow rate of the irrigation fluid through the first port when the rotational angle exceeds a first predetermined angle and to decrease a flow rate of the irrigation fluid through the second port when the flow rate of the irrigation fluid through the first port increases.

The surgical system can vary in many ways. For example, the control system can be configured to increase the flow rate of the irrigation fluid through the first port and to decrease the flow rate of the irrigation fluid through the second port as the first port moves farther away from the ground and the second port moves closer to the ground. As another example, the electrosurgical device can be configured to be releasably coupled to a tool drive assembly comprising at least one motor configured to drive a drive assembly of the fluid source, the drive assembly being operably coupled to the conduit and configured to control a flow rate of the irrigation fluid through the conduit.

In some embodiments, the ground is defined as a normal to a gravity vector. In some embodiments, the control system is configured to increase the flow rate of the irrigation fluid through the first port and to decrease the flow rate of the irrigation fluid through the second port when the rotational angle exceeds the first predetermined angle and while the rotational angle remains less than a second predetermined angle. In some embodiments, the second predetermined angle is about 22.5 degrees.

In some embodiments, the flow rate of the irrigation fluid through the first port increases proportionally to the decrease of the flow rate of the irrigation fluid through the second port. In some embodiments, the flow rate of the irrigation fluid through the first port increases proportionally to the decrease of the flow rate of the irrigation fluid through the second port. The first and second ports can be disposed on the same side of the first and second electrodes.

In another aspect, a surgical system is provided that, in some embodiments, includes an electromechanical tool including an instrument shaft and an end effector formed at a distal end thereof, the end effector having first and second electrodes and first and second fluid communication ports adjacent to the first and second electrodes, and at least one conduit configured to provide selective fluid communication between each of the first and second ports and an irrigation fluid source and a vacuum source. The control system is configured to monitor a rotational angle of the shaft relative to the ground, and the control system is further configured to, while the rotational angle is below a first predetermined angle, control the conduit to deliver the irrigation fluid through the first port at a first flow rate, and control the conduit to aspirate the irrigation fluid through the second port at a first aspiration rate. The control system is also configured to, when the rotational angle exceeds the first predetermined angle, control the conduit to deliver the irrigation fluid through the second port at a second flow rate, and control the conduit to aspirate the irrigation fluid through the first port at a second aspiration rate.

The surgical system can vary in many ways. For example, the first flow rate can be proportional to the first aspiration rate, and the second flow rate can be proportional to the second aspiration rate. As another example, the first predetermined angle can be about 90 degrees. As a further example, the electrosurgical device can be configured to be releasably coupled to a tool drive assembly comprising at least one motor configured to selectively drive the irrigation fluid source and the vacuum source. As yet another example, the control system can be further configured to control the conduit to increase the first flow rate of the irrigation fluid through the first port while the rotational angle is below a second predetermined angle that is smaller than the first predetermined angle, and to decrease the first flow rate of the irrigation fluid through the first port when the rotational angle is greater than the second predetermined angle and below the first predetermined angle.

In some embodiments, the control system is further configured to control the conduit to increase the first aspiration rate of the irrigation fluid through the second port while the rotational angle is below a third predetermined angle that is greater than the second predetermined angle and smaller than the first predetermined angle, and to decrease the first aspiration rate of the irrigation fluid through the second port when the rotational angle is greater than the third predetermined angle and below the first predetermined angle.

In some embodiments, the control system is further configured to control the conduit to increase the second flow rate of the irrigation fluid through the second port while the rotational angle is below a fourth predetermined angle that greater than the first predetermined angle, and to decrease the second flow rate of the irrigation fluid through the second port when the rotational angle is greater than the first predetermined angle and below the fourth predetermined angle. In some embodiments, the control system is further configured to control the conduit to increase the second aspiration rate of the irrigation fluid through the first port while the rotational angle is below a fifth predetermined angle that is below the first predetermined angle, and to decrease the second aspiration rate of the irrigation fluid through the first port when the rotational angle is greater than the first predetermined angle and below the fifth predetermined angle.

In a further aspect, a surgical method is provided that in some embodiments includes operating an electrosurgical device to cause first and second electrodes coupled to instrument shaft of the device to deliver power to tissue, the electrosurgical device having first and second fluid ports adjacent to the first and second electrodes, monitoring a rotational angle of the shaft relative to a ground, and controlling at least one conduit to selectively communicate an irrigation fluid between a fluid source and at least one of the first and second ports by controlling the conduit to increase a flow rate of the irrigation fluid through the first port when the rotational angle exceeds a first predetermined angle and to decrease a flow rate of the irrigation fluid through the second port when the flow rate of the irrigation fluid through the first port increases.

The surgical method can vary in many ways. For example, the surgical method can further include controlling at least one conduit to increase the flow rate of the irrigation fluid through the first port and to decrease the flow rate of the irrigation fluid through the second port as the first port moves farther away from the ground and the second port moves closer to the ground.

BRIEF DESCRIPTION OF DRAWINGS

This disclosure will be more fully understood from the following detailed description taken in conjunction with the accompanying drawings, in which.

DETAILED DESCRIPTION

Figure 1:
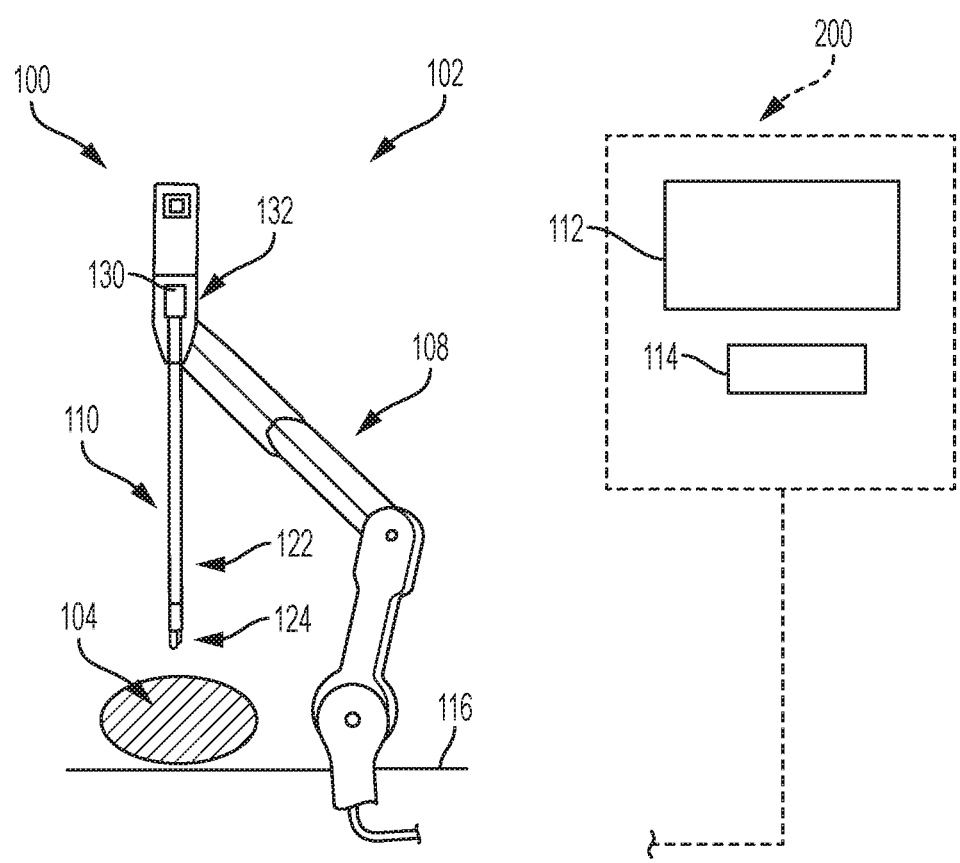
FIG. 1 is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Many surgical procedures involve removal and other invasive manipulation of tissue, which results in severing multiple blood vessels leading to blood loss. Significant blood loss may compromise the patient's health and it can complicate the surgery by resulting in accumulation of blood at the surgical site. For example, a broad area surgery, such as liver resection during which multiple blood vessels may be severed, can be complicated by blood loss into the surgical site.

An electrosurgical tool having at least one treatment electrode configured to apply energy to tissue can be used to seal blood vessels, thereby preventing blood loss. Such an electrosurgical tool can be, for example, a bipolar device having a pair of electrodes that are powered by radio frequency (RF) energy to heat and cauterize tissue and blood vessels. RF energy encompasses high-frequency alternating electrical currents (with a frequency typically ranging from 100 kHz to 5 MHz) that can have impact on biological tissue. In particular, application of RF energy causes tissue heating, which results in cell protein denaturation and desiccation. In this way, RF energy can be used to cut, coagulate, desiccate, or fulgurate tissue. Direct application of the electrodes to tissue may lead to undesired effects such as tissue charring and fouling of the electrodes by charred tissue sticking to them. Moreover, tissue, such as, for example, liver, may not offer sufficient conductivity for RF energy to be deposited near the electrodes, which can lead to electrode overheating and thus tissue charring and sticking to the electrodes.

To increase conductivity at the surgical site and thus reduce tissue charring and other undesirable effects, an electrically conductive fluid, such as a saline fluid, can be introduced into the surgical site near the electrodes to irrigate the site. Thus, electrosurgery, which can be a bipolar electrosurgery involving a use of active and return electrodes engaging tissue therebetween that is included in the electrical circuit, can be performed in a fluid environment, also referred to as a "wet field." In use, the electrically conductive fluid becomes heated as the electrodes apply RF energy (also referred to herein as "RF power") to tissue.

Although the heated fluid evaporates as it is being used, in some cases, excess of the fluid may accumulate which may result in undesirable consequences. Excess of fluid, as well as spent fluid, together with unwanted material such as the remnants of the cauterized tissue, may be removed from the surgical site by aspiration. However, it may be cumbersome and time-consuming for a surgeon to apply RF energy, irrigate, and aspirate the tissue, particularly when separate devices are required. Moreover, controlling irrigation and aspiration, particularly in a hand-held electrosurgical device with manual controls, such that appropriate amounts of fluid are delivered to the surgical site and removed therefrom, can be challenging.

Accordingly, systems, devices, and methods described herein allow controlling tissue cauterization and/or irrigation, as well as aspiration of fluids from a surgical site by a surgical or electrosurgical device or tool. The control can be performed in an automated manner. The electrosurgical tool can include a tool housing and an instrument shaft extending distally from the housing and having an end effector at a distal end thereof. The end effector includes first and second treatment electrodes configured to receive energy, such as RF energy, from an energy source and to apply the energy to tissue. The electrosurgical tool also includes an irrigation conduit or tube in fluid communication with a fluid source, such as a peristaltic pump, and an aspiration (or suction) conduit or tube in fluid communication with a vacuum source, such as a vacuum pump or another source. The irrigation tube has an outflow port in proximity to the electrodes, and the aspiration tube has an inflow port in proximity to the electrodes. The end effector can be configured to articulate with respect to the instrument shaft. Furthermore, in some embodiments, at least one of the irrigation and aspiration tubes can be extendable.

In some embodiments, the electrosurgical tool is configured to be coupled to a robotic surgical system that is used to control operation of various components of the electrosurgical tool. For example, the robotic surgical system can have a tool driver assembly configured to mate with a tool's housing such that components of the housing (e.g., various rotary inputs) receive a rotary output motion from the tool driver assembly of the robotic surgical system. In other embodiments the electrosurgical tool can be a hand held tool that is operably coupled to various actuators and a control system configured to control various aspects of the operation of the tool as discussed below.

The robotic surgical system can include or can be associated with a control system configured to control generation of energy by an electrosurgical generator (e.g., RF generator) configured to provide the energy to the electrodes of the tool. The control system is also configured to control a flow rate of an irrigation fluid delivered to the surgical site to increase conductivity of the tissue being treated at a surgical site, as well as an aspiration rate or an aspiration rate of fluids removed from the tissue at the surgical site. In some embodiment, the control system is configured to control irrigation of tissue in the vicinity of the electrodes based on power provided to the electrodes by an RF generator. In some embodiments, the control system is configured to control aspiration of fluids from the tissue being treated by the electrodes based on power provided to the electrodes by an RF generator, and to control irrigation of the surgical site based on the control of the aspiration. The control system controls the power, the irrigation flow rate, and the aspiration rate such that a desired power level is maintained and tissue sticking, charring, and other undesirable effects are decreased or eliminated. Moreover, as discussed below, the control system is configured to be fine-tuned to control one or more of the power, irrigation, and aspiration, such that it is adjustable in real time, in response to changes in tissue properties and electrodes position and other factors (e.g., electrode surface area in contact with tissue) as the tissue is being treated.

FIG. 1 is a perspective view of one embodiment of a surgical robotic system 100 that includes a patient-side portion 102 that is positioned adjacent to a patient 104, and control system 200 that can be located a distance from the patient, either in the same room, same medical facility, and/or in a remote location. The patient-side portion 102 generally includes at least one robotic arm 108 and a surgical tool or device 110 that is configured to releasably couple to the robotic arm 108. The control system 200 can include a display system 112 and various types of control systems or controls 114 for controlling the movement of the robotic arms 108, as well as movements and other functions of the surgical tool 110 during a surgical procedure.

The surgical tool 110 includes a tool or drive system housing 130 and an instrument shaft assembly 122 extending distally from the housing 130. The shaft assembly 122 has an end effector 124 coupled to a distal end thereof, which can include at least one treatment electrode operably coupled to an energy source and configured to deliver electrosurgical energy to tissue. The shaft assembly 122 can include various components, such as connectors for coupling the treatment electrodes to an energy source, an irrigation tube, an aspiration tube, an articulation rod, and/or any other components. In at least some embodiments, the instrument shaft assembly 122 is configured to rotate about a longitudinal axis thereof. It should be appreciated that the surgical tool 110 and its components are shown by way of example only, for the purpose of illustrating generally a surgical tool in which some embodiments can be implemented.

The tool or drive system housing 130 is configured to be releasably attached to the robotic arm 108, and the drive system housing 130 can include coupling features configured to allow releasable coupling of the tool 110 to the robotic system. As shown in the example of FIG. 1, the tool 110 can couple with the robotic arm 108 such that the drive system housing 130 sits on top of the motor housing 132. However, such coupling between the tool 110 and the robotic arm 108 is shown by way of example only, as other implementations can be used additionally or alternatively. For example, and as discussed above, the tool can be a hand held tool that is not associated with a robotic surgical system.

The robotic arm 108 can be wirelessly coupled to the control system 200 having a console with the display 112 and various user input devices. One or more motors (not shown) are disposed within a motor housing 132 that is coupled to an end of the robotic arm 108. The drive system housing 130 of the surgical tool 110 can house a drive system (not shown). The drive system includes various components (e.g., gears, drivers and/or actuators) configured to control operation of various assemblies of the surgical tool 110, such as any one or more of energy delivery, articulation, rotation, other types of movements, etc. Regardless of the specific way in which the drive system housing 130 is coupled to the motor housing 132, the drive system housing 130 is mounted to the motor housing 132 to thereby operably couple the motor(s) to the drive system. As a result, when the motors are activated by the control system, the motor(s) can actuate the drive system.

The surgical robotic system includes the at least one control system 114 that can receive user inputs and that can control the motor(s) in response to the user inputs and hence control movement and operation of various components of the surgical tool 110. Also, the control system can perform automatic control of at least some functions of the surgical tool. The robotic system is configured to automatically control operation of the surgical tool 110 such that, in use, certain parameters (e.g., power, a flow rate of a fluid delivered through the irrigation tube, an aspiration rate of a fluid aspirated through the aspiration tube, etc.) can be controlled "on the fly," as the surgical tool 110 is used to treat the patient 104 (e.g., to cauterize tissue).

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and tool assemblies 110.

A surgical tool that can implement the described techniques, such as, e.g., tool 110 of FIG. 1, can be coupled to a surgical robotic system that controls operation of the surgical tool. The tool can include in its housing motor-powered drivers that are configured to be selectively driven to actuate various elements of the tool. For example, as discussed in more detail below, the tool housing can include a gear assembly that interfaces and couples with at least one rotatable driven element (e.g., a motor) of the tool drive assembly to receive a rotary output motion therefrom.

In general, one or more motors can be used to drive various functions of a surgical tool. The functions can vary based on the particular type of surgical device, but in general a surgical device can include one or more drive systems that can be configured to cause a particular action or motion to occur, such as shaft and/or end effector rotation, end effector articulation, energy delivery, etc. In some embodiments described herein, the surgical tool can include one or more drive systems configured to cause irrigation, aspiration, advancement or retraction of an irrigation tube, and advancement or retraction of an aspiration tube. Each drive system can include various components, such as one or more gears that receive a rotational force from the motor(s) and that transfer the rotational force to one or more drive shafts to cause rotary or linear motion of the drive shaft(s).

The motor(s) can be located within the surgical device itself or, in the alternative, coupled to the surgical device such as via a robotic surgical system. Each motor can include a rotary motor shaft that is configured to couple to the one or more drive systems of the surgical device so that the motor can actuate the drive system(s) to cause a variety of movements and actions of the device. It should be noted that any number of motors can be used for driving any one or more drive systems on a surgical device. For example, one motor can be used to actuate two different drive systems for causing different motions. In certain embodiments, the drive system can include a shift assembly for shifting the drive system to between different modes for causing different actions. A single motor can in other aspects be coupled to a single drive assembly. A surgical device can include any number of drive systems and any number of motors for actuating the various drive systems. The motor(s) can be powered using various techniques, such as by a battery on the device or by a power source connected directly to the device or connected through a robotic surgical system. Additional components, such as sensors or meter devices, can be directly or indirectly coupled to the motor(s) in order to determine and/or monitor at least one of displacement of a drive system coupled to the motor or a force on the motor during actuation of the drive system.

In certain embodiments, when the at least one motor is activated, its corresponding rotary motor shaft drives the rotation of at least one corresponding gear assembly located within the drive system of the surgical device. The corresponding gear assembly can be coupled to at least one corresponding actuation shaft, thereby causing linear and/or rotational movement of the at least corresponding actuation shaft. While movement of two or more actuation shafts can overlap during different stages of operation of the drive system, each motor can be activated independently from each other such that movement of each corresponding actuation shaft does not necessarily occur at the same time or during the same stage of operation.

In some embodiments, a surgical system is provided that can include a surgical tool having a shaft having an end effector at a distal end thereof and at least one treatment electrode associated with the end effector, an aspiration tube, an irrigation tube, and a housing operably connected to the shaft. The aspiration tube can have an inlet port at a distal end thereof and the aspiration tube extends through the shaft. Similarly, an irrigation tube can extend through the shaft and can have an inlet port in proximity to the at least one electrode. The irrigation tube can be in fluid communication with a fluid source and the aspiration tube can be in fluid communication with a vacuum source. The surgical tool can also have a housing operably connected to the shaft and having at least one first rotatable element configured to be selectively driven to actuate at least one pump in fluid communication with the irrigation tube. The system can further include at least one motor operably connected to the housing and configured to selectively drive the first rotatable element to control a flow rate of a fluid delivered through the irrigation tube. The motor can be included in the surgical tool or it can be disposed outside the tool in the surgical system. For example, the motor can be disposed on an electromechanical robotic arm of the surgical system.

Figure 2:
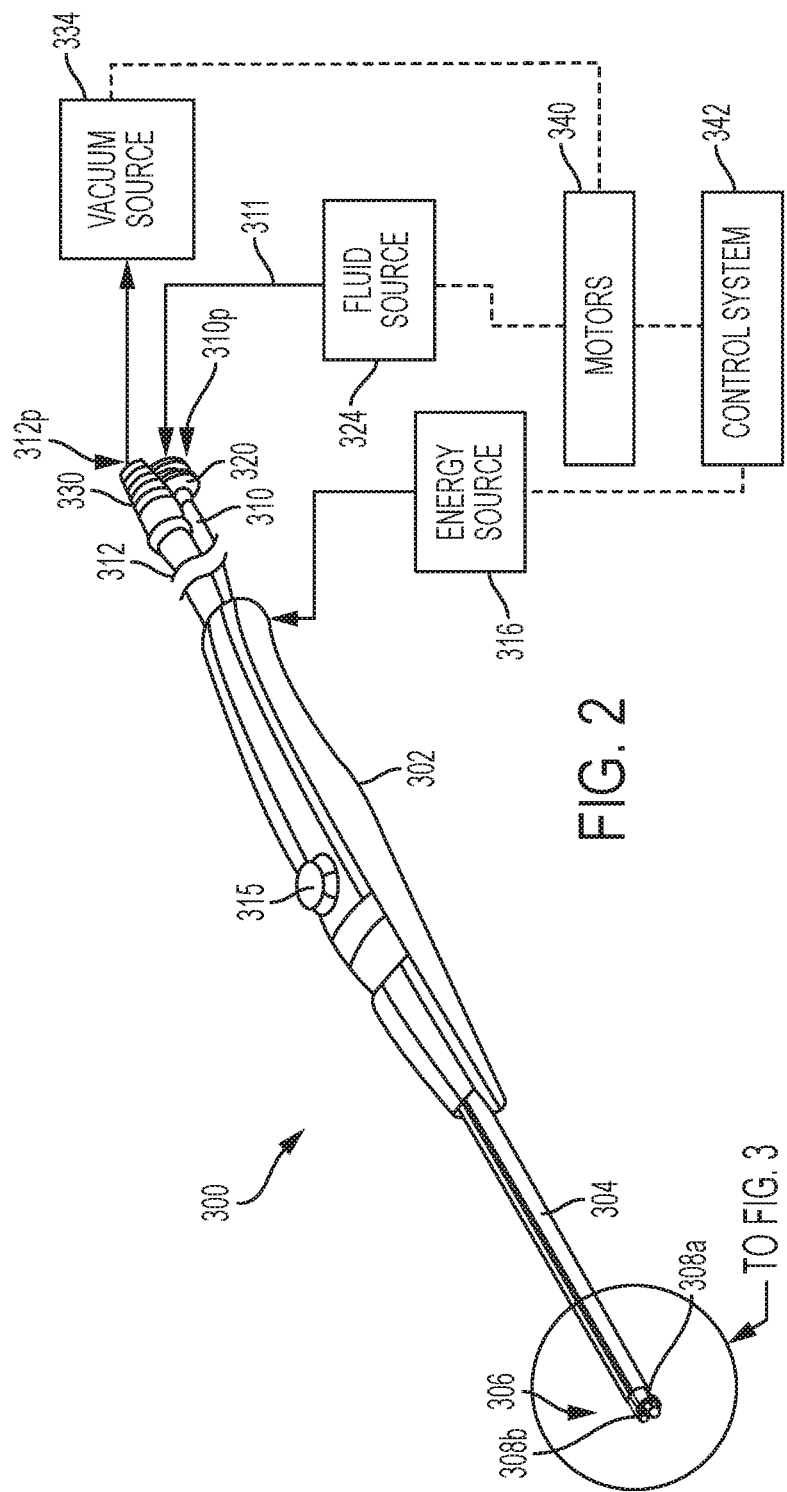
FIG. 2 is a perspective view of one embodiment of a surgical tool configured to be coupled to a surgical robotic system.
Figure 3:
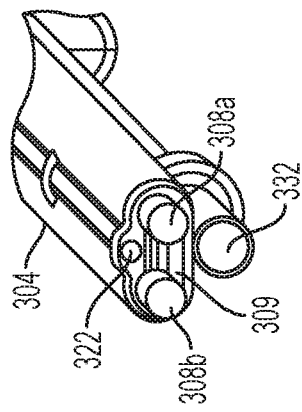
FIG. 3 is an end view of a distal end of an end effector of the surgical tool of FIG. 2.

FIG. 2 shows an embodiment of a surgical tool 300 which can be releasably coupled to a surgical robotic system and which can be controlled using the described techniques. The tool 300 can be an electrosurgical device that includes a tool housing 302, an elongate shaft 304 extending distally from the housing 302, and an end effector 306 coupled to a distal end of the shaft 304. The elongate shaft 304 can be configured to be rotated around a longitudinal axis thereof. The end effector 306 has at one treatment electrode associated therewith. In particular, in the illustrated embodiment, the surgical tool 300 can be a bipolar energy delivery device having two electrodes having energy transferred therebetween. Thus, as shown in FIG. 2, the end effector 306 has first and second electrodes 308a, 308b configured to deliver energy, such as RF energy, to tissue. The end effector 306 can be articulatable such that it is configured to articulate with respect to the shaft 304, as discussed below.

In use, the surgical tool 300 can be configured to apply RF energy to tissue in the wet field, such that a conductive fluid is delivered to a treatment site in proximity to the electrodes. Also, spent conductive fluid, as well as any other undesirable elements (e.g., byproducts of tissue coagulation), can be eliminated from the treatment site by aspiration. Accordingly, as shown in FIG. 2, the housing 302 can include an irrigation conduit or tube 310 extending through the shaft 304 and having a proximal port 320 at a proximal end 310p thereof, and a fluid evacuation or aspiration tube 312 also extending through the shaft 304 and having a proximal port 330 at a proximal end 312p thereof. At least one of the irrigation and aspiration tubes 310, 312 can be configured to advance distally and retract proximally with respect to a distal end of the shaft 304.

As further shown in FIG. 2, showing an example of a distal end of the surgical tool 300, the irrigation tube 310 extends through the shaft 304 such that a distal port 322 of the irrigation tube 310, which is configured to operate as an outlet port for fluid discharge, is disposed in proximity to the electrodes 308a, 308b. Similarly, the aspiration tube 312 extends through the shaft 304 such that a distal port 332 of the aspiration tube 312, which is configured to operate as an inlet port receiving fluids accumulated at the surgical site, is disposed in proximity to the electrodes 308a, 308b.

In the illustrated example, as shown in FIG. 2, the distal port 322 of the irrigation tube 310 is disposed above the distal port 332 of the aspiration tube 312. It should be appreciated that the shaft 304 can be rotatable, such that the position of the distal port 322 of the irrigation tube 310 with respect to the distal port 332 of the aspiration tube 312 can change. Nevertheless, the tool 300 is configured such that the treatment site (i.e., tissue being treated with the electrodes 308a, 308b) can be irrigated from a higher port which is disposed above the tissue, and suction can be applied to the treatment site adjacent to tissue, to reach fluids accumulated at the treatment site.

As shown in FIG. 2, the proximal port 320 of the irrigation tube 310, configured as a coupling, can be in fluid communication with a fluid source 324 which can provide fluid such as, e.g., saline, buffered saline, Ringer's solution, or other electrically conductive fluids such as aqueous fluids containing ionic salts. The fluid source 324 can include or can be associated with components that actively pump the fluid into the proximal fluid source port 320, as well as with control electronics. In the illustrated embodiments, the fluid source 324 can be in the form of a pump, such as a peristaltic pump that can be controlled via a control system associated with a surgical robotic system, as discussed in more detail below. The peristaltic pump can be disposed in the housing 302 of the surgical tool 300. Regardless of its specific configuration, the fluid source 324 accesses, via a fluid line 311, a fluid reservoir storing the electrically conductive fluid(s) that are delivered in a controlled manner through the distal port 322 of the irrigation tube 310.

The proximal port 330 of the aspiration tube 312, configured as a coupling, can be in fluid communication with a vacuum source 334 configured to generate an aspiration flow of fluids being evacuated from the surgical site. The vacuum source 334 can include components some of which are external to the tool's housing 302. For example, in some embodiments, the vacuum source 334 encompasses a vacuum-based pump disposed externally to the tool 300 (e.g., in the same operating room or a medical facility as the robotic system to which the tool 300 can coupled). The vacuum-based pump is configured to be selectively controlled to aspirate fluids through the aspiration tube 312. The vacuum source 334 can be coupled to a power supply and to a fluid collector configured to receive fluids and other material removed by the vacuum source 334. The vacuum source 334 is also operably coupled to a control system. The aspiration is carried out by applying vacuum through the distal port 332 of the aspiration tube 312. A differential volumetric flow rate between the distal port 332 side of the aspiration tube 312 and the side of the vacuum source 334 (e.g., the vacuum-based pump) causes a vacuum level or pressure differential, $\Delta P$, to be created between the distal port 332 side of the aspiration tube 312 and the vacuum source 334 side of the aspiration tube 312. Thus, in embodiments discussed herein, the control of aspiration is defined as a control of the vacuum or aspiration rate within the aspiration tube 312 between the vacuum source 334 and the distal port 332 of the aspiration tube 312.

As further shown in FIG. 2, the tool 300 can be coupled to an energy source 316 configured to supply energy, such as RF energy, to the electrodes 308a, 308b. The RF energy can be supplied from the energy source 316 to the electrodes 308a, 308b via a suitable connector 317, such as, e.g., a cable. A portion of the connector can extend through the housing 302 and the shaft 304. The energy source 316 can be an external RF generator configured to supply power to the tool 300. An output of the RF generator can be controlled to produce various waveforms to allow adjustment of RF energy applied by the electrodes 308a, 308b to tissue, to thereby have different effects on tissue. In some embodiments, the energy source 316 can include an external generator that may be powered by AC mains. In some implementations, the electrical and electronic circuit elements associated with the energy source 316 can be supported by a control circuit board assembly. The energy source 316 can include a control circuit configured to be selectively controlled to adjust a level of RF power and a time of application of the RF power in response to sensed changes in properties of tissue due to RF energy applied thereto by the electrodes 308a, 308b.

As discussed in more detail below, an external controller associated with the surgical robotic system to which the tool 300 can be operatively coupled can control operation of the energy source 316 to deliver electrosurgical energy to tissue. The energy source 316 (e.g., its microprocessor) can receive commands from the controller and can adjust voltage and/or current so that desired level of RF power is delivered by the electrodes 308a, 308b, based on the commands. The energy source 316 can include other components, such as, for example, a display and/or input devices configured to receive user input to control operation of the energy source 316. In some embodiments, the energy source 316 can be configured to be controlled by the controlled such the energy source 316 may not include some or all of the input devices for manual control of the energy source 316.

The housing 302 of the tool 300 can include one or more activation devices to permit a user to control the functions of the tool 300. For example, the tool 300 can include a valve 315 configured to provide access to the irrigation tube 310. In implementations in which the tool 300 can be interchangeably used as the hand-held or robot-controlled device, the valve 315 can be a metering valve that can be activated by a user to control an amount of fluid flowing through the irrigation tube 310. In such embodiments, the tool 300 can also include a control input device configured to receive user input to control delivery of RF energy to the electrodes. Such control input device can additionally or alternatively be disposed on or associated with the energy source 316.

As shown schematically in FIG. 2, the surgical tool 300 can be configured to be operably coupled to at least one motor 340 operably connected to the housing, the at least one motor 340 being configured to selectively control the fluid source 324 and the vacuum source 334 to deliver and remove fluids from the treatment site, respectively. For example, as discussed in more detail below, the fluid source 324, such as a peristaltic pump, can include a rotatable element configured to be selectively driven by one of the motors 340. Similarly, the vacuum source 334 can include an element (e.g., a valve in the housing 302) configured to be selectively driven by one of the motors 340. The surgical tool 300 can include other components in the tool housing 302, such as, for example, a shaft rotation driver assembly configured to activate components that cause the shaft 304 to rotate, an end effector articulation driver assembly configured to advance and retract an articulation rod and thus articulate the end effector 306 with respect to the shaft, and an aspiration tube extension driver configured to advance (or extend) and retract the aspiration tube 312. In addition, in some embodiments, the tool can include an irrigation tube extension driver configured to advance and retract the irrigation tube. The motors 340, which can be disposed in a tool driver of a surgical robotic system (e.g., in a robotic arm) can be configured selectively drive the various drivers in the tool housing, such that each motor drives a respective driver, though other arrangements can be implemented. As shown in FIG. 2, a control system 342, which can be a remote device, can be configured to control the motors 340, the energy source 316, and any other components included in or associated with the surgical tool 300.

As discussed above, the end effector 306 of the tool 300 includes the first and second electrodes 308a, 308b configured to receive electrical power from the energy source 316 and to apply RF power to tissue. The current can pass between the electrodes to allow formation of a closed-loop electrical circuit including an RF generator, the patient, and the electrodes (and the wiring). In the bipolar device, only the tissue disposed between the two electrodes is part of the electrical circuit.

Figure 4B:
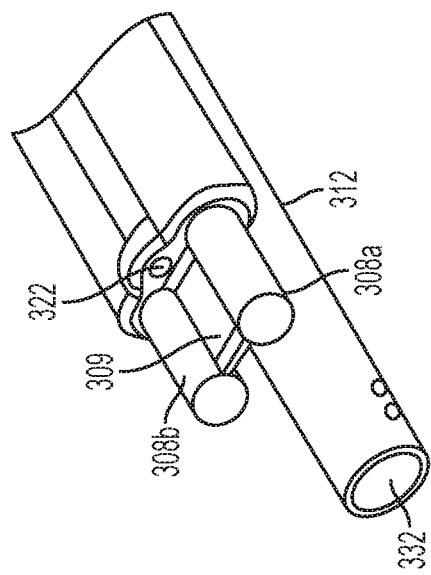
FIG. 4B is yet another view of the end effector of FIG. 3, showing an irritation tube in an extended configuration.
Figure 4A:
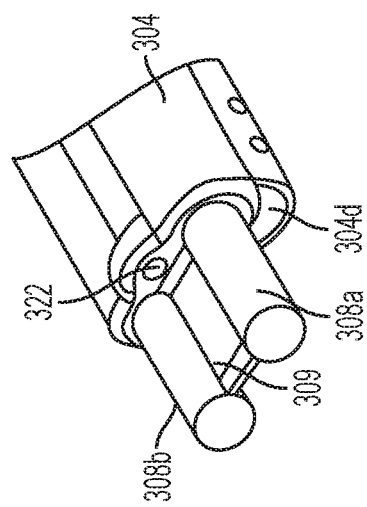
FIG. 4A is another view of the end effector of FIG. 3.

The electrodes 308a, 308b can extend beyond a distal end 340d of the tool's shaft 304. In the illustrated embodiment, as shown in FIG. 4B, the extended ends of the electrodes 308a, 308b can be separated by a diverter 309. The diverter 309 can contact the first electrode 308a at one side of the diverter 309, and the diverter 309 can contact the second electrode 308b at a second side of the diverter 309. The diverter 309 can include an electrically insulating material and/or a heat resistant material, which may include, e.g., plastic such as a polycarbonate, or a ceramic. In some embodiments, the diverter 309 can be deformable. In some implementations, the housing 302 can include a mechanism to control a configuration of the deformable diverter.

Figure 4C:
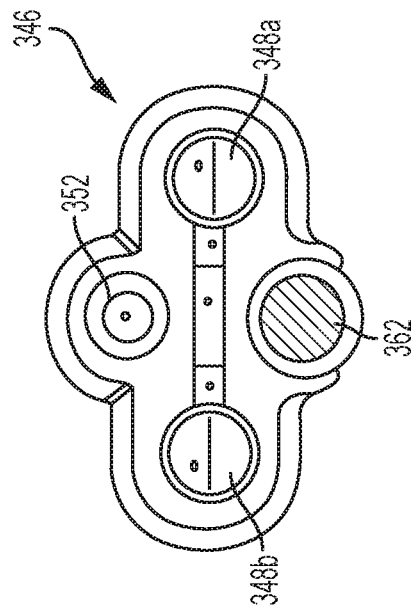
FIG. 4C is a cross-sectional proximal view of another embodiment of an end effector of a surgical tool.

As mentioned above, the aspiration tube 312 of the end effector 306 can be extendible and retractable. FIG. 4C illustrates the aspiration tube 312 in an extended configuration such that its distal port 322 is advanced distally with respect to the electrodes 308a, 308b. In some implementations, the irrigation tube can be similarly configured to be extended and retracted.

A surgical tool in accordance with the described techniques can have various configurations. Also, a surgical tool can have various types of end effectors having treatment electrodes. FIG. 4D illustrates another example of an end effector 346 having first and second electrodes 348a, 348b. A surgical tool having the end effector 346 can have, among other components, an irrigation tube having a distal port 352, and an aspiration tube having a distal port 362. The surgical tool can be similar to tool 300 of FIG. 2.

In some embodiments, as mentioned above, an end effector of a surgical tool, which can be releasably coupled to and controlled by a surgical robotic system, can be configured to articulate with respect to a longitudinal axis of a tool's shaft. For example, although not described in detail with respect to FIGS. 2, 3, 4A, and 4B, the end effector 306 of the surgical tool of FIG. 2 can be configured to articulate with respect to the shaft 304. The end effector 346 of FIG. 4C can also be configured to articulate with respect to a tool's shaft to which it is coupled.

Figure 5A:
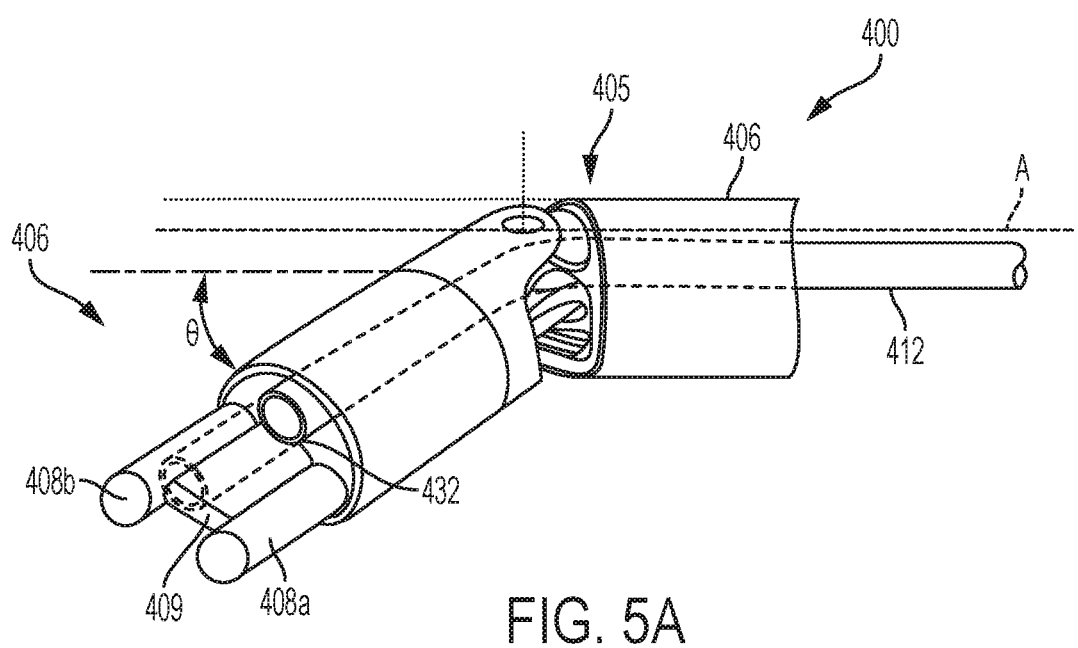
FIG. 5A is a perspective view of one embodiment of an articulatable end effector of an electrosurgical tool.
Figure 5B:
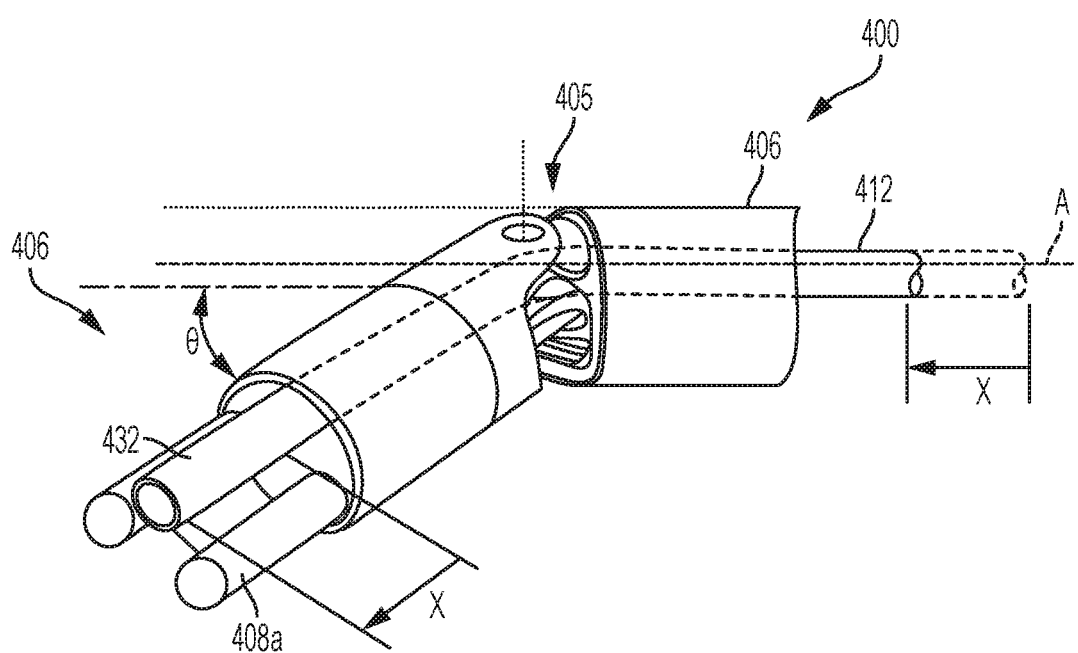
FIG. 5B is another view of the articulatable end effector of FIG. 5A, showing an aspiration tube of the electrosurgical tool in an extended configuration.

FIGS. 5A and 5B illustrate one embodiment of an articulatable end effector 406 of a surgical tool 400. The surgical tool 400, only a distal portion of which is shown, can be similar to tool 300 (FIG. 7) and the description of its components therefore not repeated in connection with FIGS. 5A and 5B. In some embodiments, the surgical tool 300 of FIG. 2 can have the end effector 406 as shown in FIGS. 5A and 5B. The end effector 406 having first and second electrodes 408a, 408b with a diverter 409 therebetween can be coupled distally to a tool's shaft 404 via a wrist 405 that allows articulation of the end effector 406 with respect to the shaft 404. The wrist 405 allows articulation of the end effector 406 such that the functions of the tool 400 (e.g., application of RF energy, irrigation, aspiration, etc.) are not affected.

In FIGS. 5A and 5B, the effector 406 is shown articulated with respect to the shaft 404 such that the effector 406 is disposed at an angle $\theta$ with respect to a longitudinal axis A of the shaft 404. Similar to tool 300 (FIG. 2), the surgical tool 400 includes an aspiration tube 412 with a distal port 432 and an irrigation tube (not shown). FIG. 5A shows the aspiration tube 412 in a non-extended, retracted configuration (and a retracted configuration of the tune 412 is shown in phantom), and FIG. 5B shows the aspiration tube 412 in the extended configuration such that the aspiration tube 412 is extended distally to a distance x. It should be appreciated that the distal portion of the surgical tool 400 is shown in FIGS. 5A and 5B to be upside down, and that the aspiration tube 412 is therefore shown above the electrodes 408a, 408b and the diverter 409 while the irrigation tube port is obscured.

Figure 6:
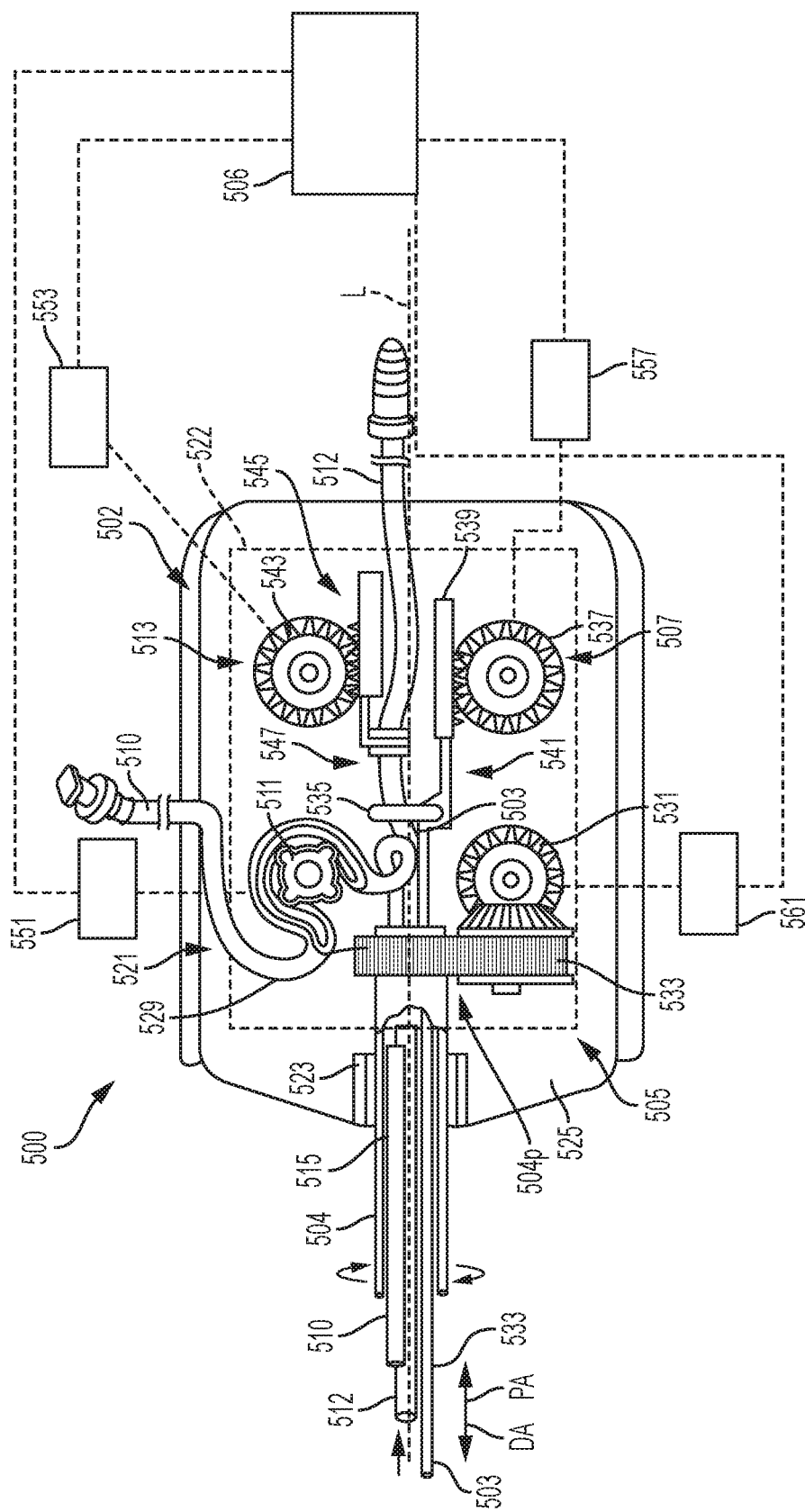
FIG. 6 is a partially transparent schematic view of one embodiment of an electrosurgical tool, with a drive system of the electrosurgical tool being coupled to motors that are operably coupled to a control system.

To allow articulation of an end effector of an electrosurgical tool, as well as movements of other components of the electrosurgical tool, the housing of the tool can include various actuators or drivers configured to be selectively driven to actuate respective components of the tool. FIG. 6 illustrates one embodiment of a surgical or electrosurgical tool 500 (which can also be referred to as an "electromechanical device") having a tool housing 502 including a drive system 522 and being coupled to a proximal end of an instrument shaft 504. The drive system 522 is shown coupled to motors 551, 553, 557, 561 that are operably coupled to a control system 506. A person skilled in the art will appreciate that the motors and control system can be located within the tool housing 502 to form a powered hand-held device, or they can be located external of the housing 502, such as in a surgical robotic system. In the illustrated embodiment, the motors 551, 553, 557, 561 and the control system 506 are located in a robotic system. As shown in FIG. 6, the instrument shaft 304 has a lumen 515 extending therethrough, and the lumen receives therein the articulation rod 503, the irrigation tube 510, and the aspiration tube 512. Moreover, aside from the differences described in detail below, the instrument shaft 504 of the electrosurgical tool 500 can be similar to the shaft 304 of the tool 300 of FIG. 2 and is therefore not described in detail herein. Further, for purposes of simplicity, certain components of the electrosurgical tool 500 are not illustrated in FIG. 6.

While the drive system 522 can have a variety of configurations, in this exemplary embodiment, the drive system 522 includes four drive assemblies: a pump drive assembly 521 including a pump 511 (e.g., a peristaltic pump) having at least one rotatable element and in fluid communication with an irrigation tube 510; a shaft rotation drive assembly 505 configured to cause the shaft 504 to rotate about its longitudinal axis L; an articulation drive assembly 507 configured to cause an articulation rod 503 to move in distal and proximal directions relative to the housing 502 and thus cause an end effector (not shown) coupled distally to the shaft 504 to articulate; and an aspiration tube movement drive assembly 513 configured to advance and retract the aspiration tube 312 relative to the housing 502. Each drive assembly, which is discussed in more detail below, can be coupled to a rotary motor shaft of a corresponding motor, which, in the illustrated embodiment, is a tool holder of a robotic arm of a surgical robotic system. The tool holder can include a motor housing, such as, e.g., motor housing 132 of FIG. 1. During actuation, the corresponding motor can actuate each drive assembly. Further, as described above, the motors are controlled by the control system 506.

In addition, although not shown in FIG. 6, the housing 502 can include a valve coupled to a vacuum source (which can be external to the tool 500) and actuated to control aspiration of fluids from a surgical site treated using the tool 500. Furthermore, although not present in this implementation, in some embodiments, the tool housing 502 can include an irrigation tube movement drive assembly configured to advance and retract an irrigation tube.

The pump drive assembly 521, the shaft rotation drive assembly 505, the articulation drive assembly 507, and the aspiration tube movement drive assembly 513 can each include corresponding at least one rotatable element that can receive a rotary output control motion from a corresponding motor. The output control motion received from the motor is converted into a rotary control motion for rotating the rotatable element and thus activating the corresponding drive assembly of the tool 500. The tool housing 502 can have a tool mounting plate 525 having various rotatable elements and associated components coupled thereto. In at least one embodiment, the housing 504 of the tool 500 is configured to receive a corresponding first rotary output motion from a surgical robotic system and convert that first rotary output motion to a rotary control motion for rotating the elongate shaft 504 about a longitudinal tool axis A1.

In some embodiments, the tool mounting plate 525 can have an adapter side having driven rotatable body portions, discs, or elements (referred to as "driven elements") that are coupled to corresponding rotatable elements (e.g., drive gears) of the tool housing that cause movement of corresponding drive assemblies of the housing. This occurs when the tool housing 504 is coupled to a tool driver assembly of a surgical robotic system such that motors of the tool driver assembly provide rotary control motion to the driven elements of the adapter side. It should be appreciated, however, that any other configurations of an interface between the surgical tool and the surgical robotic system can be implemented. For example, in some implementations, the rotatable elements (e.g., drive gears) of the tool mounting plate of the tool housing can be directly coupled to corresponding motors of the tool driver assembly of the surgical robotic system.

While the shaft rotation drive assembly 505 can have a variety of configuration, in some implementations, the shaft rotation drive assembly 505, as shown FIG. 6, can include a tube gear segment 529 that is formed on (or attached to) a proximal end 504p of the instrument shaft 504 for operable engagement with a rotational gear assembly. As shown, the rotational gear assembly includes a rotary drive gear 533 that is rotatably supported on the tool mounting plate 525 and that is in meshing engagement with the tube gear segment 529. The rotary drive gear 533 is also in meshing engagement with a rotation drive gear 531 that is operably coupled to a first motor 561. In use, when the shaft motor 561 is activated, its corresponding rotary motor shaft drives the rotation of the rotational gear assembly, such as the rotation drive gear 531, and consequently the tube gear segment 529, thereby causing the rotation of the instrument shaft 504.

In the illustrated embodiments, articulation of an end effector of the tool 500 (which can be similar, for example, to end effector 406 of FIGS. 5A and 5B) with respect to the elongate shaft 504 can be accomplished by axially moving the articulation rod 503 in distal and proximal directions "Da" and "Pa," respectively. Axial movement of the articulation rod 503 is accomplished by controlling translational axial movement of a drive bracket 535 operably coupled to a rotational gear assembly of the articulation drive assembly 507. The drive bracket 535 (e.g., in the form of a ring bracket) is translated by applying rotary output motions to the articulation drive assembly 507 that is operably supported on the tool mounting plate 535 as shown in FIG. 6. In this embodiment, the articulation drive assembly 507 includes an articulation drive gear 537 operably coupled to the second motor 557 controlled by the control system 506, as shown schematically in FIG. 6. The articulation drive gear 537 is in meshing driving engagement with a rack 539 coupled to the drive bracket 535 via an arm 541 extending distally from the rack 539 as shown in FIG. 6. In use, when the second motor 557 is activated, the motor 557 applies a rotary output motion to the rotational gear assembly, in particular, to the articulation drive gear 537, which causes the rack 539 to translate axially, thereby causing the articulation rod 503 an thus the end effector coupled thereto to translate axially.

While the pump drive assembly 521 have can various configurations, in the illustrated embodiment, the pump drive assembly 521 includes the peristaltic pump 511 that has at least one rotatable element and that is in fluid communication with the irrigation tube 510. As shown in FIG. 6, the pump 511 is operably coupled to a third motor 551 configured to apply a rotary output motion thereto, such that the pump controls a flow rate of a fluid delivered to a treatment side by the irrigation tube 510. The third motor 551 is operably coupled to the control system 506, as shown in FIG. 6.

In the illustrated embodiments, distal extension and proximal retraction of the aspiration tube 512 can be accomplished by controlling, via the control system 506, the aspiration tube movement drive assembly 513. While the aspiration tube movement drive assembly 513 have can various configurations, in the illustrated embodiment, the aspiration tube movement drive assembly 513 includes a drive gear 543 that is in meshing engagement with a rack 545 which is coupled to the aspiration tube 512 via a coupling 547. The drive gear 543 is operably coupled to the fourth motor 553 that is, in turn, operably coupled to the control system 506. In use, when the fourth motor 553 is activated, its corresponding rotary motor shaft drives the rotation of the drive gear 543, which causes the rack 545 to translate. Distal or proximal translation of the rack 545, which is coupled to the aspiration tube 512, causes corresponding distal extension or proximal retraction of the aspiration tube 512. In this way, in use, the aspiration tube 512 can be controlled to be disposed in proximity to an area within a treatment site in a patient's body from which elimination of fluids is desirable.

It should be appreciated that the motors 561,557, 551, 553 are referred to herein as "first," "second," "third," and "fourth," respectively, for description purposes only, and not to indicate any particular order. Also, although each motor is schematically shown to control a corresponding drive gear, in some implementations, one motor can control more than drive gear, or other implementations are possible. Furthermore, it should be understood that, as mentioned above, any one or more of the motors 561,557, 551, 553 can be located on the surgical tool 500, or they can be external to the tool 500. In addition, the tool 500 can include or can operably couple to other motors that are not shown herein.

Figure 7:
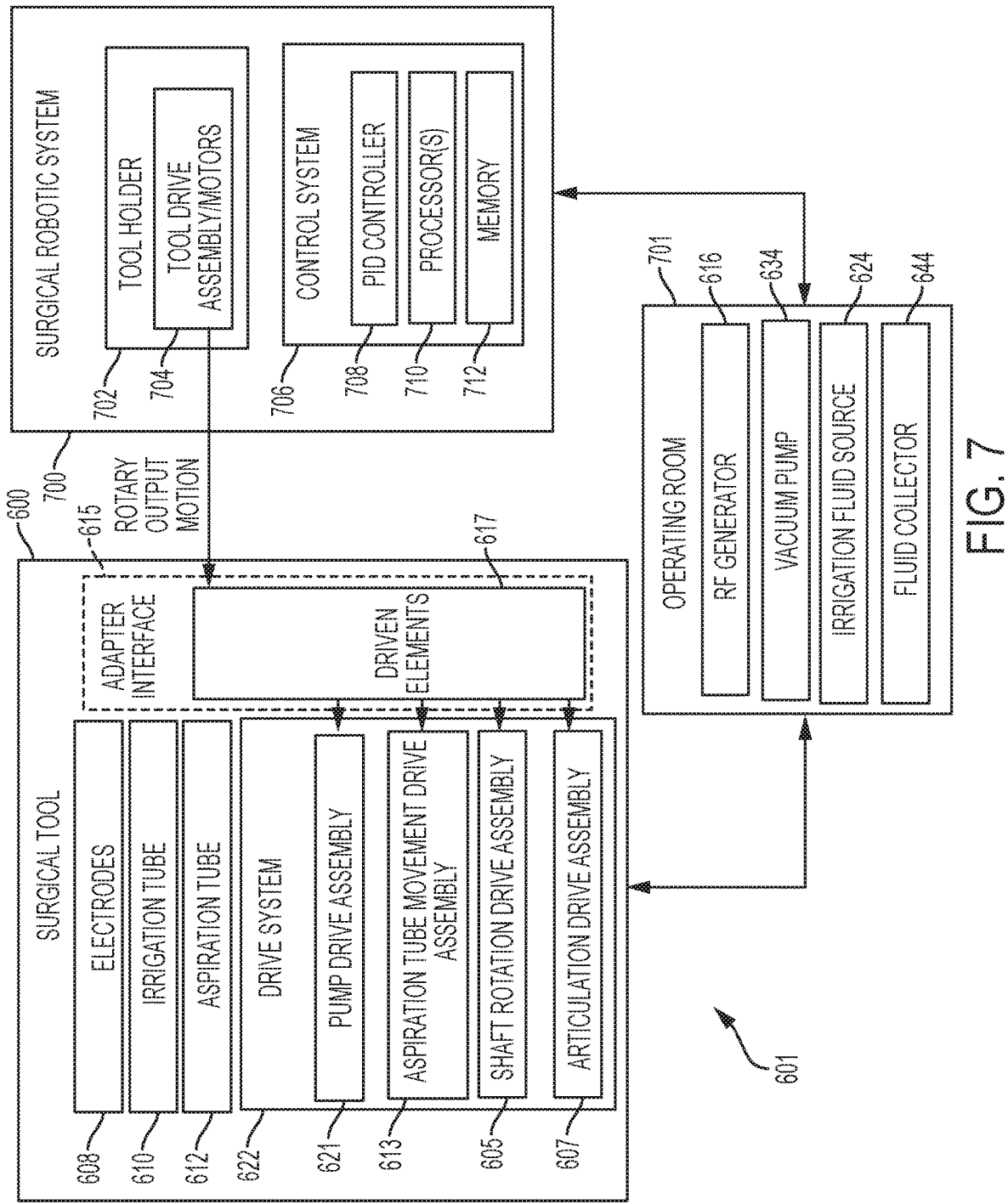
FIG. 7 is a block diagram illustrating an example of a system including a surgical tool and a surgical robotic system configured to control operation of the surgical tool.

FIG. 7 shows schematically a system 601 in which some embodiments can be implemented. As shown, the system 601 includes a surgical device or tool 600, a surgical robotic system 700, and an operating room 701. As shown, the surgical tool 600, which is generally similar to surgical tool 500 (FIG. 6), includes electrodes 608, an irrigation tube 610, an aspiration tube 612, and a drive system 622 that includes a peristaltic pump drive assembly 621, an aspiration tube movement drive assembly 613, a shaft rotation drive assembly 605, and an articulation driver assembly 607. The drive system 622 is disposed in a tool housing of the tool 600 that, in this embodiment, is configured to be mounted on the surgical robotic system 700. It should be understood that the components of the surgical tool 600 are shown schematically in FIG. 7 and that, for example, portions of the irrigation tube 610 and the aspiration tube 612 can be considered part of the drive system 602. The surgical tool 600 also includes an optional adapter interface 615 including driven elements 617 and operably coupled to the surgical robotic system 700. For example, as discussed above regarding FIG. 6, the surgical tool 600 has a tool mounting plate (e.g., tool mounting plate 525 of FIG. 6), which can have an adapter side having driven elements that are coupled to corresponding rotatable elements (e.g., drive gears) of the tool housing when the tool 600 is coupled to the surgical robotic system 700.

As shown in FIG. 7, the driven elements 617 are coupled to each of the pump drive assembly 621, the aspiration tube movement drive assembly 613, the shaft rotation drive assembly 605, and the articulation driver assembly 607. Thus, the driven elements 617 are configured to selectively receive a rotary output motion from a tool driver assembly (e.g., motors) 704 of the surgical robotic system, which causes the driven elements 617 to rotate such that they, in turn, cause the components of the drive system 622 to operate. The adapter interface 615 can be configured such that a driven element rotates a respective one of the peristaltic pump drive assembly 621, the aspiration tube movement drive assembly 613, the shaft rotation drive assembly 605, and the articulation driver assembly 607. However, in other implementations, one driven element can be configured to operatively couple to more than one component of the surgical tool.

It should be appreciated that the adapter interface 615 is optional and that, in some embodiments, the components of the drive system 622 can be configured to directly operably couple to corresponding motors disposed on the surgical robotic system 700. Also, in some implementations, for example, when the surgical tool is configured to be interchangeably used as a hand-held tool or as a robotic system-driven tool (or in other implementations), some or all of the motors can be located on the surgical tool.

As shown in FIG. 7, the surgical robotic system 700 includes a tool holder 702 including the tool drive assembly/motors 704. The robotic system 700 also includes a control system 706, which is generally similar to control system 506 (FIG. 6) and which is schematically shown to encompass a PID controller 708, at least one processor 710, and a memory 712. It should be understood that that the control system 706 can be or can include a suitable computing device having the at least one processor 710 and memory 712. The PID controller 708 can be implemented in the form of computer-executable instructions stored in the memory 712 and executable by the at least one processor 710. However, in some implementations, however, some or all components of the PID controller 708 can be implemented in electronic circuitry. Furthermore, the control system 706 can include various other types of controllers, such as PI (proportional-integral), PD (proportional-derivative), P (proportional), or I (integral) controllers.

The control system 706, generally, can control movement and actuation of the surgical tool 600. For example, the control system 706 can include at least one computer system and can be operably coupled to at least one motor of the tool drive assembly 705 that drives the drive system 602 on the surgical tool 600. The computer system can include components, such as the at least one processor 710, that are configured for running one or more logic functions, such as with respect to a program stored in the memory 712 coupled to the processor 710. For example, the processor 710 can be coupled to one or more wireless or wired user input devices ("UIDs"), and it can be configured for receiving sensed information, aggregating it, and computing outputs based at least in part on the sensed information. These outputs can be transmitted to the drive system 602 of the surgical tool 600 to control the surgical tool 600 during use.

In certain embodiments, the control system 706 can be a closed-loop feedback system. The stored data within the computer system can include predetermined threshold(s) for one or more stages of operation of the drive system. When the control system 706 is actuated, it drives one or more motors on or coupled to the surgical tool 600, consequently actuating the drive system 602 through the use of the tool 600. In use, the control system 706 can receive feedback input from one or more sensors coupled to the motor(s) that sense displacement and/or torque of the motor(s). The computer system can aggregate the received feedback input(s), perform any necessary calculations, compare it to the predetermined threshold for the corresponding stage of operation, and provide output data to the motor(s). The control system 706 receives another feedback input, such as tissue impedance sensed by the electrodes as they apply RF energy to the tissue.

If at any time during each stage of operation the control system determines that the received input deviates from a desirable value, exceeds a maximum predetermined threshold, or is less than a minimum predetermined threshold, the control system can modify the output data sent to the motor based on the programmed logic functions. For example, the control system can modify the output data sent to the motor(s) to reduce a current delivered to the motor to thereby reduce a rotational speed of the motor(s) or to stop movement of the motor(s).

As also shown in FIG. 7, in this example, the operating room system 701 includes an RF generator 616 configured to supply RF energy to the tool's electrodes 608, a fluid source 624 configured to supply fluid (e.g., saline or another fluid) to the irrigation tube 610, a vacuum pump 634 configured to provide vacuum force to the aspiration tube 612, and a fluid collector 644 configured to receive fluids (and possibly solid matter) aspirated by the aspiration tube 612.

It should be appreciated that the various components are shown as being included in the surgical tool 600, the surgical robotic system 700, and the operating room 701 by way of example only. Also, the operating room 701 is shown as a component separate from the surgical tool 600 and the robotic system 700 by way of example only, since some of the components shown in FIG. 7 as included in the operating room 701 can be considered part of one or both the surgical tool 600 and the surgical robotic system 700. For example, the RF generator 616 can be considered part of the robotic system 700 or, in some implementations, part of the surgical tool 600. In use, the RF generator 616 coupled to the tool 600 can be disposed, for example, on a cart located in the operating room when the surgery that involve the use of the tool 600 is performed. Thus, the components of the operating room 701 are shown in FIG. 7 to indicate relatively large components that, in at least one implementation, are disposed in an operating room or other location in a medical facility since these components are less portable than the surgical tool 600. For example, an operating room can include a built-in vacuum pump configured to couple to various devices that require vacuum pressure for operation, such as the aspiration tube 612, in this example. It should also be appreciated that each of the surgical tool 600, the surgical robotic system 700, and the operating room 701 includes other components that are not shown in FIG. 7 for the sake of simplicity.

In the illustrated embodiments, the surgical tool can be configured to apply RF energy to tissue, which results in RF current flowing through the tissue and the tissue being heated via resistive heating. The tissue offers resistance to the current flowing therethrough and the amount of electrical current flowing into the tissue is directly related to the amount of power delivered by the RF generator and the resistance or impedance of the tissue. Effects of the RF energy (current) in the tissue are determined based on electrical properties of the current (frequency, amperage, voltage, power, and waveform of an output), time of exposure of the tissue to the RF current, properties of the tissue (e.g., impedance, fluid content, etc.), a configuration and size of electrodes, and other factors. In the illustrated embodiments, operation of a surgical tool can be controlled via a control system (which can include more than one controller), such as a control system 706 (FIG. 7) when the surgical tool is coupled to a surgical robotic system. The control system can be configured to control the application of RF energy to tissue based on monitored parameters, to achieve a desired effect on tissue. Furthermore, the control system controls the surgical tool to perform other functions, such as irrigation, aspiration, shaft rotation, end effector articulation, etc.

In some embodiments, a control system associated with a surgical robotic system and operably connected to an electrosurgical generator controls power provided by a power generator to electrodes of a surgical tool "on the fly," as the surgical tool is used to treat a tissue. The control system is configured to compare an actual power delivered to the tissue through the electrodes to a predetermined, target power set point, wherein the actual power is determined based on monitored tissue impedance. The control system is also configured to control a flow rate of an irrigation fluid through at least one port of an irrigation conduit or tube in fluid communication with a fluid source, such as a peristaltic pump. For example, in some embodiments, the control system compares a target, or set, flow rate (a "flow rate set point") of an irrigation fluid based on an actual flow rate of an irrigation fluid. The actual flow rate can be assessed, for example, based on monitored tissue impedance. The difference between the actual flow rate and the flow rate set point is used to determine a current control value for a motor configured to operate a peristaltic pump delivering the irrigation fluid through at least one port of an irrigation tube. In some embodiments, the surgical tool is controlled such that an irrigation fluid is delivered to a tissue only when the electrodes of the tool are in contact with the tissue.

In the illustrated embodiments, as discussed in more detail below, the control system can control the power using a proportional-integral-derivative (PID) controller, and a flow rate of an irrigation fluid through a port of the tool can be controlled based on the power (determined based on the sensed impedance) using the PID controller.

The PID controller is a closed-loop control feedback mechanism designed to eliminate a need for continuous operator attention during a process. The PID controller acquires an actual value (or process variable) and derives a control signal from a difference or error between a predetermined set point value and the actual value. Thus, the PID controller can automatically adjust system variables with the goal of maintaining a process variable at the set point. The PID controller continuously calculates the error value e(t) as the difference between a desired set point and a measured process variable and applies a correction based on proportional, integral, and derivative terms. The controller attempts to minimize the error over time by adjusting a control variable u(t), such as, for example, power supplied to electrodes, current supplied to a motor, etc. The PID controller includes proportional control (P), integral control (I), and derivative control (D) terms or portions. The P term is proportional to the amount of the error signal and depends on the present time, the I term is proportional to the amount and duration of the error signal (i.e. depends on accumulation of past errors), and the D term provides an output that is proportional to the rate of change of the error such that D term's goal is to anticipate future errors based on the current rate of change.

The control variable u(t) is a weighted sum of P, I, and D terms and is defined as:

$$u(t) = K_p e(t) + K_i \int_o^t e(\tau)d\tau + K_d \frac{de(t)}{dt}, \quad (1)$$

where $K_p$, $K_i$, and $K_d$ are coefficients or gains for the proportional, integral, and derivative terms, respectively. In the illustrated embodiments, the gains $K_p$, $K_i$, and $K_d$ are varying coefficients that may be set based on monitored control signals, such as the power (measured based on tissue impedance acquired through the electrodes) and the flow rate of an irrigation fluid through a port (also referred to herein, for the sake of brevity, a "flow rate"). The control system is configured to adjust the output value to a desired value. To compute the control gains $K_p$, $K_i$, and $K_d$, in one embodiment, the control system can use the time rate of change in the impedance $$\frac{\Delta Z}{\Delta t},$$

along with the time rate of change in the flow rate, $$\frac{\Delta Q}{\Delta t}.$$

Figure 8A:
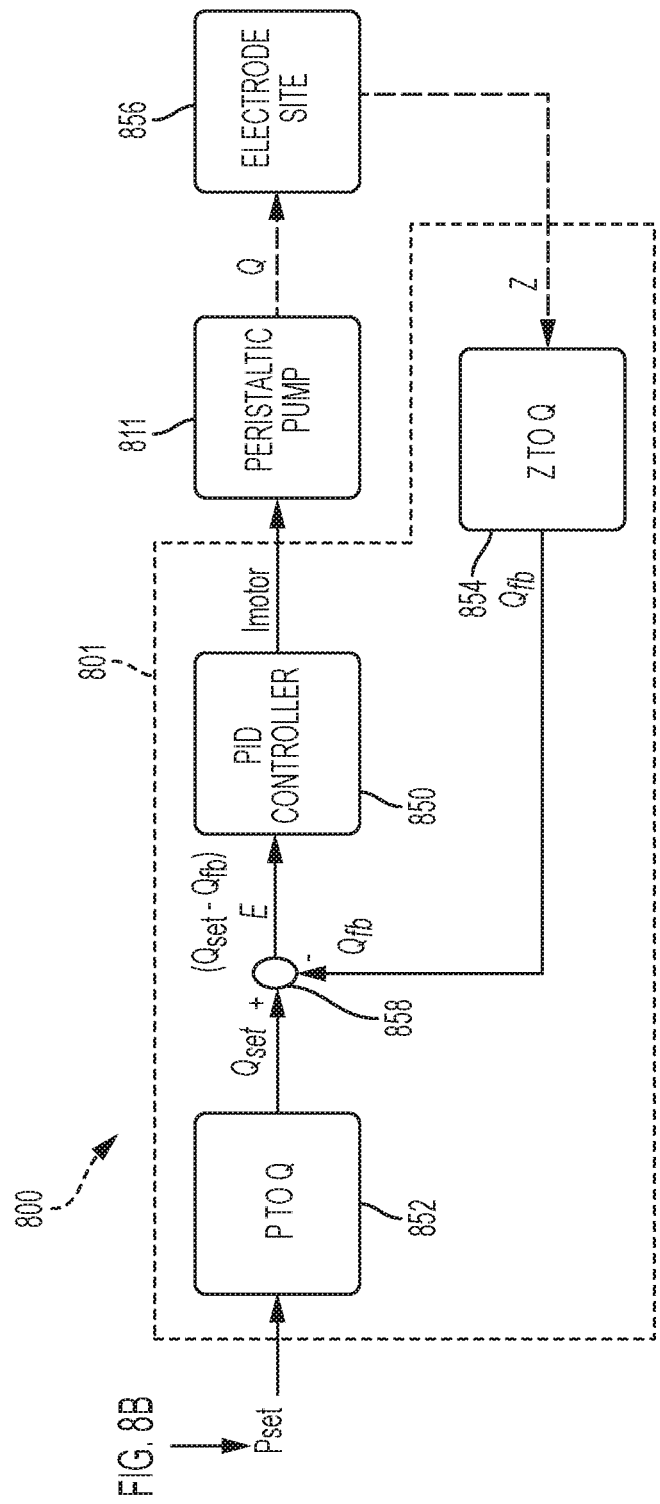
FIG. 8A is a block diagram illustrating an example of a system configured to control a flow rate of an irrigation fluid delivered through a port of an irrigation tube extending through a surgical tool, flow rate being controlled based on comparison of powered delivered to a tissue to a power set point.

FIG. 8A illustrates a control system 800 configured to control a flow rate of an irrigation fluid delivered by electrodes of a surgical tool to a surgical site, based on a deviation of power delivered to tissue through the electrodes from a predetermined power set point, Pset. The control system 800 is configured to adjust the flow rate in real time, based on a deviation of the power from its desired or target power value Pset. The surgical site is referred to herein as an "electrode site" since the irrigation fluid (e.g., a saline or other conducing fluid) is delivered into the area of a tissue in a patient's body to which treatment electrodes of the tool apply RF energy, to allow the treatment to be performed in the wet field. The system 800 can be used to control a flow rate of a fluid delivered through a port of an irrigation tube, such as, e.g., irrigation tube 310 (FIG. 2), irrigation tube 510 (FIG. 6), irrigation tube 610 (FIG. 7) or any other irrigation tube or conduit at least a portion of which extends through the surgical tool.

Figure 8B:
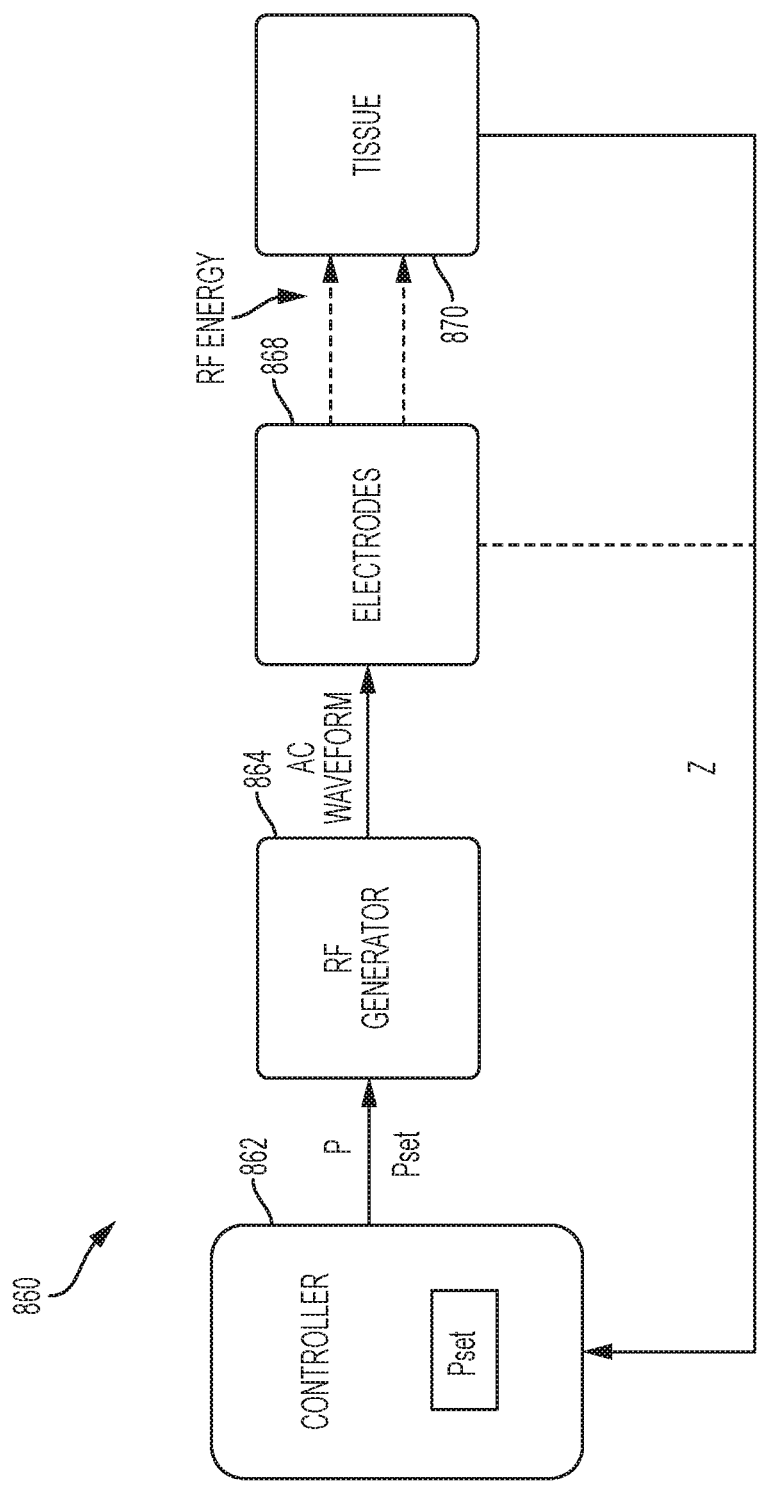
FIG. 8B is a block diagram illustrating an example of a system configured to control power generated by an RF generator and delivered to a tissue through electrodes of a surgical tool.

As shown in FIG. 8A, the control system 800 can include a peristaltic pump 811 (e.g., pump 511 of FIG. 6), a PID controller 850, a first "P to Q" conversion factor 852, and a second "Z to Q" conversion factor 854. The control system 800 includes a controller 801 encompassing the PID controller 850, and the "P to Q" and "Z to Q" conversion factors 852,854, and the controller 801 can be part of control system 706 of surgical robotic system 700 of FIG. 7. The peristaltic pump 811 is configured to regulate a flow rate (Q) of the fluid delivered to an electrode site 856. The sensed impedance between the electrodes leads the flow rate of the fluid delivered by the pump 811 through the irrigation tube to the electrode site 856. The impedance measured between the electrodes is converted into a flow rate, referred to as a feedback flow rate (Qfb), by the (known) conversion factor "Z to Q" 854. The RF power set point, Pset, determined as schematically shown in FIG. 8B, is converted into a flow rate set point, Qset ("Flow rate set point" in FIG. 9), by the (known) conversion factor shown as "P to Q" 852 in FIG. 8. The quantity "(Qset−Qfb)" is an error signal, denoted by "e" in FIG. 8A, which is generated by an adder 858 that performs the function of subtracting the feedback Qfb from the flow rate set point Qset. As shown, the error signal "e" is supplied to the PID controller 850 that processes the error signal "e" and computes a motor current, Imotor, which is applied to a motor controlling the peristaltic pump 811 to produce the desired flow rate Q. The motor current Imotor is increased or decreased based on the deviation of the actual flow rate Qfb from the flow rate set point Qset. In this way, the deviation of the actual flow rate Qfb (determined based on the sensed impedance) from the flow rate set point Qset is used to control operation of the pump 811.

Figure 9:
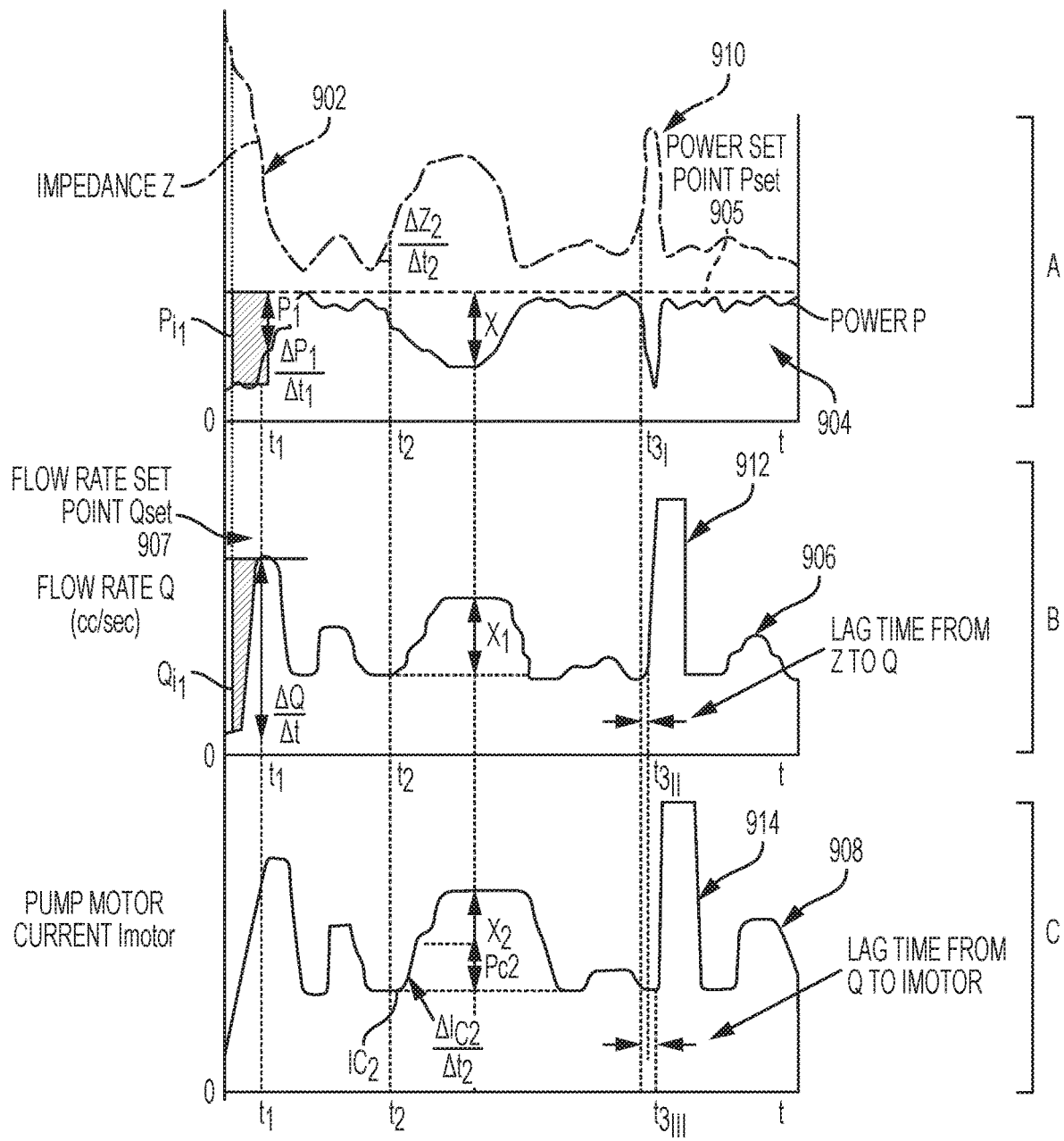
FIG. 9 shows graphs illustrating an example of variation of monitored tissue impedance, power, a flow rate of an irrigation fluid delivered through a port of an irrigation tube, and a motor current control signal provided to a motor driving a pump that controls the flow rate of the irrigation fluid through the irrigation tube, as function of time.

FIG. 8B shows a system 860 configured to control power delivered from an RF source to a tissue through electrodes of an electrosurgical tool, such as any of the surgical tools described herein. As shown, the system 860 includes a controller 862 configured to determine the power P, based on sensed tissue impedance. As also shown in FIG. 8B, the controller 862, which can be included, e.g., in control system 706 (FIG. 7), includes the power set point Pset, which can be defined in any suitable manner, based on target power that is desired to be delivered to the tissue. For example, it can be received by the controller 862 based on user input. As shown in FIG. 9, discussed in more detail below, in the example illustrated, the power set point Pset can be in the form of a constant. However, in some implementations of the controller 862, the power set point can be adjustable based on various factors, such as, e.g., the sensed issued impedance. Regardless of how it is determined, the power set point Pset is used in controller 801 (FIG. 8A), and it can be used in other controllers or control systems described herein.

The power to be applied by an RF generator 864 to the tissue is generated by the controller 862. As shown in FIG. 8B, a signal indicating the determined power P is provided by the controller 862 to the RF generator 864 that produces the desired power at electrodes 1308 of the electrosurgical tool. For example, the RF generator 864 can send a respective voltage control signal (shown by way of example as "AC Waveform") to the electrodes 1308 that apply corresponding current ("RF energy") to a tissue 870, in view of the goal of achieving the power set point Pset. The tissue 870 can be located, e.g., at the electrode side 856 (FIG. 8A). As shown in FIG. 8B, impedance Z (in Ohms) monitored at the electrode 1308 site is used to adjust the power P (in Watts). In the illustrated embodiments, the controller 862 is configured to adjust the power P such that the power delivered to the tissue treats the tissue in the manner that avoids tissue charring and sticking of the tissue to the electrodes.

FIG. 9 shows an example of a process of controlling a flow rate of an irrigation fluid based on a deviation of RF power from a power set point Pset during a surgical procedure. The process shown in FIG. 9 can be performed, for example, by the system 800 of FIG. 8A and system 860 of FIG. 8B, through these systems are exemplary only and control systems having other configurations can be used additionally or alternatively.

Section A of FIG. 9 includes a graph 902 illustrating an example of variation of tissue impedance Z as a function of time, and a graph 904 illustrating an example of variation of the power P as a function of time, wherein the power P is power delivered by an RF power source to a tissue through electrodes of an electrosurgical tool. Section B of FIG. 9 shows a graph 906 illustrating an example of variation of a flow rate Q as a function of time. Section C of FIG. 9 shows a graph 908 illustrating an example of variation of a motor current ("Imotor") delivered to a motor configured to drive a pump (e.g., pump 811 in FIG. 8A) of the electrosurgical tool, as a function time. In the illustrated embodiments, as discussed above, the motor configured to cause the peristaltic pump 811 to rotate is located on the surgical robotic system. However, in some implementations, the motor can be located on the surgical tool.

In the example shown in FIG. 9, the power P is monitored based on a predetermined power set point Pset (line 905) that is set on the RF generator, as shown, e.g., in FIG. 9B. Deviation of the power P from the power set point Pset is used to control the irrigation. In particular, as discussed above in connection with FIG. 8A, the flow rate Q of the irrigation fluid provided to the tissue (electrode site) is determined based on the power P, which is, in turn, determined based on the tissue impedance Z. A flow rate set point Qset (shown in line 907 in section B of FIG. 9) can be determined based on the power set point Pset, and deviation of the flow rate Q from the flow rate set point Qset is used to control, via a PID controller, the motor current Imotor.

As shown in FIG. 9, the power P (graph 904) is generally inversely proportional to the impedance Z (graph 902) such that, when the impedance increases, the power P is decreased. The irrigation flow rate Q (graph 906) is generally directly proportional to the impedance Z, through the flow rate Q increases with some delay after the impedance Z has decreased. Also, as shown in FIG. 9, although the curve for the irrigation fluid flow rate generally follows the impedance curve, the flow rate can vary differently than the impedance. For example, when the impedance is below a certain value, the flow rate may remain constant. As shown in FIG. 9, the pump motor current Imotor (graph 908) is generally directly proportional to the flow rate Q.

In the illustrated embodiment, as mentioned above, the control system includes the PID controller to calculate an error value as a difference between a target power set point (which is desired to be delivered to a tissue) and actual power delivered to the tissue by the electrodes. The PID controller applies a correction to the error value based on proportional P, integral I, and derivative D terms. Each of the terms has tunable coefficients that can be derived from monitored parameters.

As shown in section A of FIG. 9, in the illustrated example, at a time point t1, the power (graph 904) applied to the tissue (determined based on the sensed impedance shown in the graph 902) is below the power set point Pset, such that a value of the power P1 at the time point t1 can be a proportional term of the error value. A hashed area (Pi1) under a line 905 indicating the power set point Pset and above the curve for the power P (graph 904) at a time interval from zero to t1 (thus an area under the curve) indicates how long the actual power has been different from the power set point Pset, and this area can be an integral term of the error value. In section A, a slope $$\frac{\Delta P1}{\Delta t1}$$

indicates a rate of change of the power over time, such as whether the power changes in the manner that it approaches the target Pset value or that is goes away from the target Pset. The rate of change $$\frac{\Delta P1}{\Delta t1}$$

can be a derivative term of the error value. In the illustrated embodiments, the larger each of the P1, Pi1, and rate of change $$\frac{\Delta P1}{\Delta t1}$$

power values becomes, the more it affects the flow rate Q.

Furthermore, as shown in section B of FIG. 9, at the time point t1, the flow rate (graph 906) of the irrigation fluid provided to the tissue (determined based on the sensed impedance shown in the graph 902 in section A) is at flow rate set point Qset (line 907). A hashed area (Qi1) under a line 907 indicating the flow rate set point Qset and above the curve for the actual flow rate Q (graph 906) at the time interval from zero to t1 indicates how long the actual flow rate been different from the flow rate set point Qset. A slope $$\frac{\Delta Q}{\Delta t}$$

indicates a rate of change of the actual flow rate over time. In the illustrated embodiments, the larger each of the flow rate values, area under the curve Qi1, and rate of change $$\frac{\Delta Q}{\Delta t}$$

of the flow rate becomes, the more it can affects the motor current Imotor.

As additionally shown in FIG. 9, the magnitude of the deviation (or an error) of the actual power P (graph 904) from the power set point Pset (line 905) is shown by an arrow x, the magnitude of the deviation of the actual flow rate Q (graph 906) from the flow rate set point Qset (line 907) is shown by an arrow x1, and the magnitude of the deviation of the motor current Imotor (graph 908) from the actual power at the time point t2 is shown by an arrow x2. As shown, the deviation x1 is greater than the deviation x, and the deviation x1 is also greater than the deviation x2.

In this example, the flow rate Q is approximately inversely proportional to the actual power P and is thus approximately directly proportional to the impedance Z. The current Imotor is approximately directly proportional to the flow rate Q. The flow rate is controlled such that it lags from the impedance Z, and the pump motor control current Imotor lags from the flow rate. In particular, in FIG. 9, there is a delay between an increase of the impedance a time point $t3_1$, which leads to a peak 910, and a corresponding increase in the flow rate at a time point $t3_{11}$, which leads to a corresponding peak 912 of the flow rate. Similarly, a delay between the beginning of peak 912 of the flow rate at a time point $t3_{11}$ and a beginning of a corresponding peak 914 of the current Imotor at a time point $t3_{111}$ indicates that the current Imotor lags from the flow rate Q. These lags or delays between the time domain signals shown in FIG. 9 can be used to trigger the PID controller terms.

Figure 10:
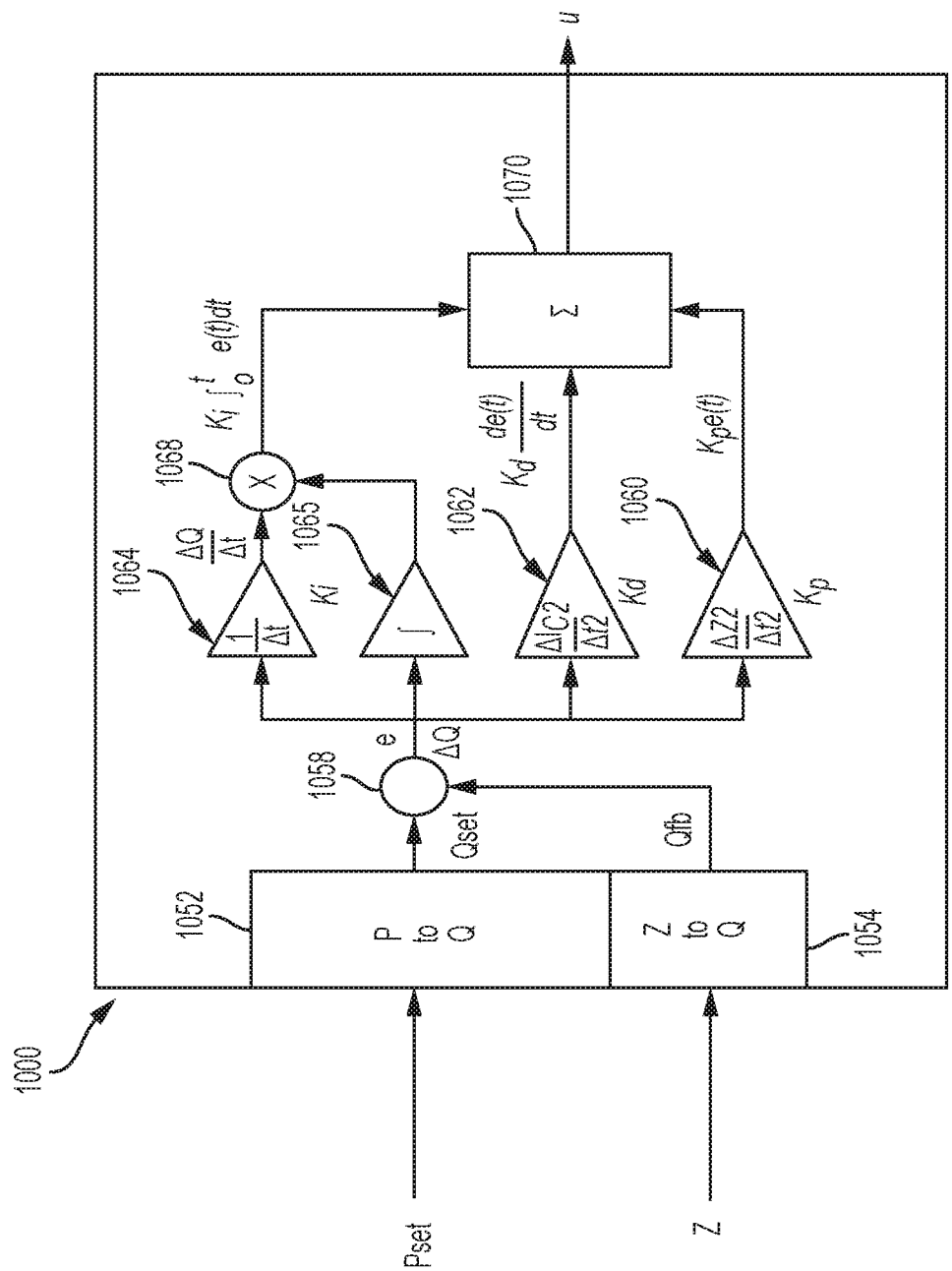
FIG. 10 is a block diagram illustrating an example of a proportional-integral-derivative (PID) controller.

FIG. 10 shows an example of a PID controller 1000, such as the PID controller 850 of FIG. 8A, that can be used in the illustrated embodiments to generate an output control signal ("u"), such as the motor applied to a motor controlling the peristaltic pump 811 to produce the desired flow rate Q. As shown, the PID controller 1000 includes a "P to Q" conversion factor block 1052 providing a flow rate set point value (Qset), and a "Z to Q" conversion factor block 1054 providing a feedback flow rate value (Qfb). The Qset and Qfb flow rates are supplied to an adder 1058 that subtracts Qfb from Qset to generate an error signal "e", also denoted as ΔQ in FIG. 10. The error signal "e" is provided to each of proportional, derivative, and integral gain blocks 1060, 1062, 1064 of the PID controller 1000, respectively. The integral gain block 1064 denotes an integral gain $$\frac{1}{\Delta t2}$$

that is, together with an output of an integrator block 1065 determining duration of the error signal ΔQ, is supplied to a multiplier 1068 that provides an integral portion of the PID controller 1000 to a summer 1070. The proportional and integral gain blocks 1060, 1062 also provide their respective outputs to the multiplier 1068 that generates the output control signal u, such as an Imotor current for controlling a motor causing a peristaltic pump to rotate.

As shown in FIG. 10, the proportional, derivative, and integral gain blocks 1060, 1062, 1064 of the PID controller 1000 have respective gains or coefficients $K_p$, $K_d$, and $K_i$. In this example, the coefficient $K_p$ of the proportional gain block 1060 is $$\frac{\Delta Z2}{\Delta t2},$$

the coefficient $K_i$ of the integral gain block 1064 is $$\frac{\Delta Q}{\Delta t},$$

and the coefficient $K_d$ of the derivative gain block 1062 is $$\frac{\Delta I_{c2}}{\Delta t2}.$$

It should be appreciated, however, that the implementation of the PID controller 1000 in FIG. 10 is exemplary only, and that any of the gains $$\frac{\Delta P1}{\Delta t1}, \frac{\Delta Z2}{\Delta t2}, \frac{\Delta Q}{\Delta t}, \text{ and } \frac{\Delta I_{c2}}{\Delta t2}$$

shown in FIG. 9 can be used as any of the coefficients $K_p$, $K_i$, and $K_d$ for the PID controller 10. Also, any one of the gains $$\frac{\Delta P1}{\Delta t1}, \frac{\Delta Z2}{\Delta t2}, \frac{\Delta Q}{\Delta t}, \text{ and } \frac{\Delta I_{c2}}{\Delta t2},$$

for example, a change in the flow rate $$\frac{\Delta Q}{\Delta t},$$

can be used as a coefficient for all of the proportional, derivative and integral gain blocks 1060, 1062, 1064 of the PID controller 1000. Also, although the PID controller 1000 is shown, control of operation of the peristaltic pump 811 can be performed using a PI (proportional integral), PD (proportional derivative), or another controller.

A control system can be configured to control an electrosurgical device or tool in various ways. In some embodiments, a control system is configured to control an aspiration rate of fluids aspirated from a target tissue by an aspiration tube of the tool based on sensed impedance of the target tissue. The control system is further configured to control a flow rate of a fluid delivered by an irrigation tube of the tool based on the aspiration rate. For example, the control system can be configured to control a motor coupled to the vacuum source to cause the vacuum source to increase the aspiration rate as the impedance increases. The flow rate of the irrigation fluid can be controlled such that an increase of the aspiration rate is followed by an increase in the flow rate, and the increase in the flow rate being proportionate to the increase in the aspiration rate.

Figure 11:
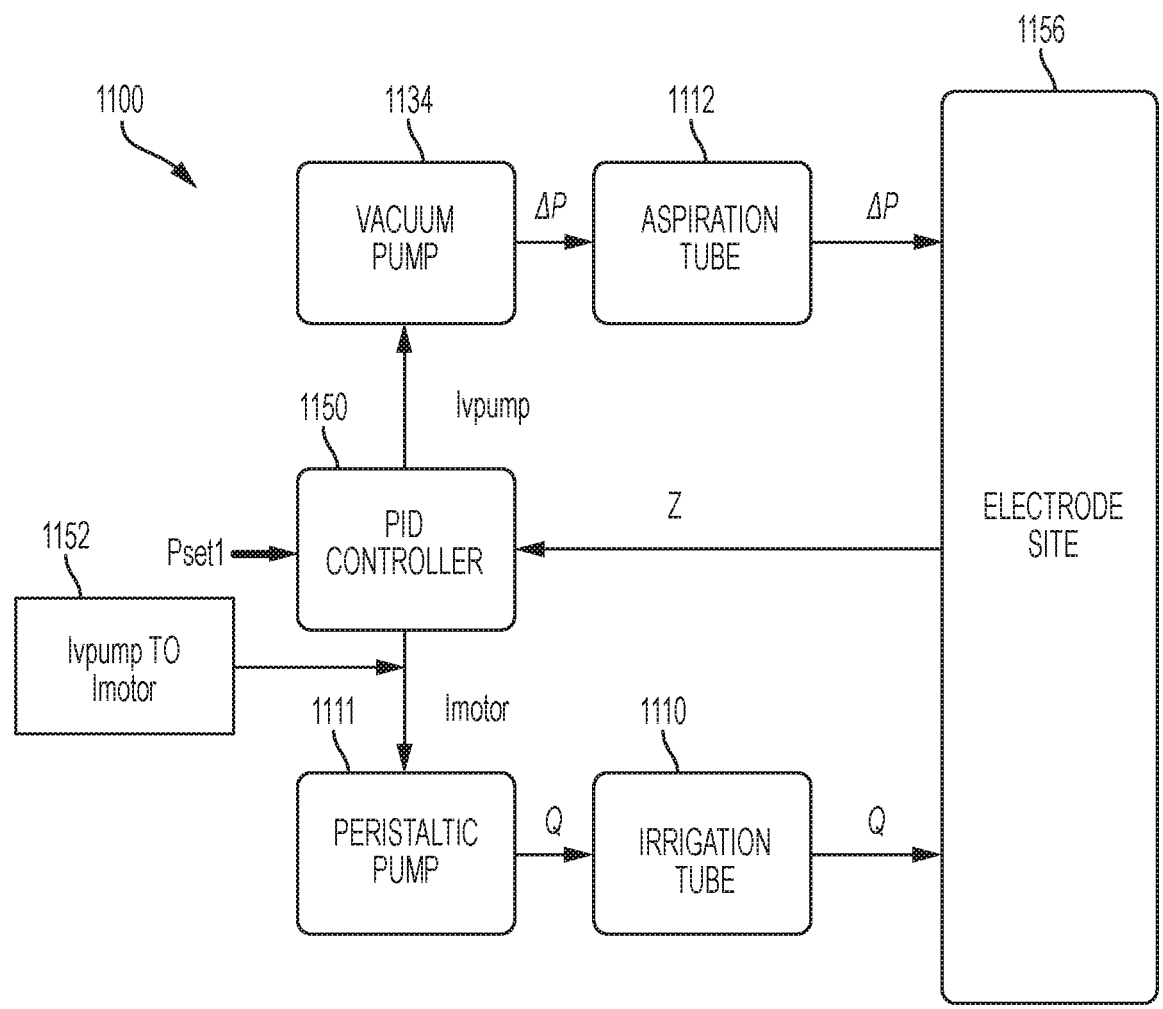
FIG. 11 is a block diagram illustrating an example of a control system configured to control an aspiration rate through a port of an aspiration tube based on measured tissue impedance and to control a flow rate through a port of an irrigation tube based on the aspiration rate.

FIG. 11 illustrates a control system 1100 configured to control an aspiration rate of a fluid being aspirated, based on tissue impedance sensed when the tissue is treated with electrodes of an electrosurgical tool, and to control a flow rate of an irrigation fluid being delivered to the tissue based on the controlled aspiration rate. As shown in FIG. 11, in this example, the control system 1100 includes a PID controller 1150, a vacuum source or pump 1134 configured to deliver a vacuum force to an aspiration tube 1112 at the controlled aspiration rate, and a peristaltic pump 1111 configured to provide a fluid to an irrigation tube 1110 at the controlled irrigation flow rate. The PID controller 1150 can be included in control system 706 (FIG. 7). In this example, the PID controller 1150 is configured to control the vacuum pump 1134 such that a current control signal Ivpump generated for a motor controlling operation of the vacuum pump 1123 is used to generate a current control signal Imotor for the peristaltic pump 1111, as discussed in more detail below.

The irrigation tube 1110 delivers the fluid to an electrode site 1156 in the vicinity of electrodes of the electrosurgical tool, and the aspiration tube 1112 aspirates fluids, which can include solid matter, from the electrode site 1156. In this example, the PID controller 1150 receives a power set point Pset1 and determines a difference (or an error) between the power set point Pset1 and actual power delivered into the tissue that is determined based on sensed tissue impedance ("Z" in FIG. 11). Thus, similar to controller 801 (FIG. 8A), the PID controller 1150 has a "Z to P" conversion factor configured to convert sensed impedance values into power values. The PID controller 1150 generates a current control signal ("Ivpump" in FIG. 11) for controlling operation of the vacuum pump 1134. For example, the control signal Ivpump can be used to control a motor causing operation of the vacuum pump 1134, which can be a built-in motor or a motor external to the vacuum pump 1134. The thus controlled vacuum pump 1134 controls an aspiration tube communicatively coupled between the vacuum pump 1134 and an inflow port of the aspiration tube in proximity to the tool's electrodes, to aspirate fluids at the electrode site 1156 at the desired aspiration rate corresponding to the control signal Ivpump, as shown in FIG. 11.

Figure 12:
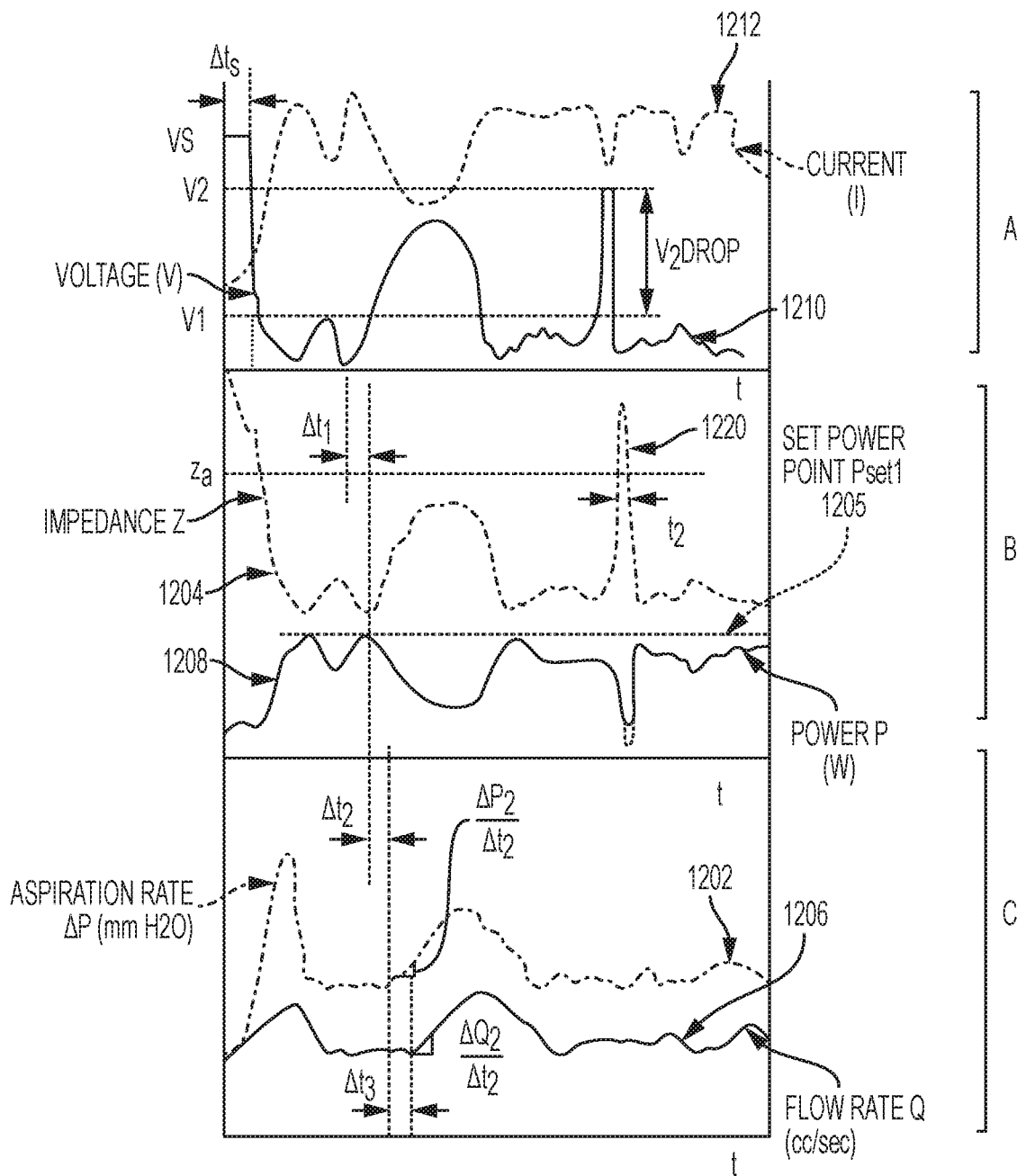
FIG. 12 shows graphs illustrating an example of variation of monitored tissue impedance, power, current, voltage, an aspiration rate of fluids aspirated through a port of an aspiration tube, and a flow rate of an irrigation fluid delivered through a port of an irrigation tube, as function of time.

As mentioned above, the PID controller 1150 is also configured to generate a current control value ("Imotor" in FIG. 11) for controlling current provided to a motor causing operation of the peristaltic pump 1111. The peristaltic pump 1111, driven by the motor operated based on the control value Imotor, controls the irrigation tube 1110 to deliver a fluid to the electrode site 1156 at the desired flow rate, as shown in FIG. 11. In this embodiment, the flow rate is controlled based on the aspiration rate, and the control signal Imotor is thus generated based on the control signal Ivpump. For example, the flow rate Q is controlled such that it is linked to the aspiration rate ΔP, as shown in FIG. 12 discussed below. Furthermore. FIG. 11 shows schematically that the control system 1100 can include an "Ivpump to Imotor" conversion part 1152 configured to compute the control signal Imotor based on the control signal Ivpump. As one example, the Imotor can be calculated as follows:

$$Imotor(n+1)=c*Ivpump(n), \quad (2)$$

where c is a constant that scales the amplitude of the motor current Ivpump, (n+1) is the next calculation, and n is the present calculation time step. It should be appreciated that the control signal Imotor can be generated based on the control signal Ivpump in various other ways, such that, as a result, the control signal Imotor for the peristaltic pump motor is proportionally linked to the control signal Ivpump for the vacuum pump motor.

FIG. 12 illustrates an example a process of controlling, during use of an electrosurgical tool for tissue coagulation, an aspiration rate of fluid(s) at a surgical site based on sensed tissue impedance, and controlling a flow rate of an irrigation fluid delivered to the surgical site based on an aspiration rate. During a surgical procedure involving wet field coagulation, a temperature of the irrigation fluid used to increase electrical conductivity of a tissue at the surgical site can increase within a short period time. Thus, it is desirable to remove the irrigation fluid from the surgical site at an appropriate aspiration rate. Thus, before further delivery of the irrigation is performed, it is desirable to ensure timely removal of the heated irrigation fluid from the treatment site. In some embodiments, the flow rate of the irrigation fluid can be linked to the aspiration rate of the fluids from the surgical site.

In at least some embodiments, the process of FIG. 12 can be performed using the control system 1100 of FIG. 11. FIG. 12 shows, in section C, a graph 1202 illustrating variation of the aspiration rate ΔP (which is a change of a rate of pressure over time, measured, in this example, in mm H2O) as a function of time t. As shown, the aspiration rate ΔP varies based on sensed tissue impedance Z, shown as a function of time t in a graph 1204 in section B of FIG. 12. FIG. 12 also shows an example of the control of a flow rate Q (measured, in this example, in cc/sec), shown as a function of time t in a graph 1206 in section C of FIG. 12, based on the controlled aspiration rate ΔP.

The aspiration rate can be measured in various ways. For example, in some embodiments, a surgical tool, such as surgical tool 500 in FIG. 6, can include a vacuum-based pump in addition to or instead of the peristaltic pump 511. The vacuum-based pump can be driven by a motor (e.g., motor 551 in FIG. 6, which can be on a robotic system) similar to the way in which the pump 511 is driven. Furthermore, because in this embodiment the irrigation flow rate trails the aspiration rate, in some implementations, a peristaltic pump, such as peristaltic pump 511 in FIG. 6, may not be included in the surgical tool.

Section B of FIG. 12, showing the impedance graph 1202, also shows a graph 1208 illustrating actual power P (in Watts) delivered to the tissue, as a function of time t. As in other embodiments, the power P is controlled based on measurements of the tissue impedance. A line 1205 indicating a power set point Pset1 shows a predetermined desired or target power. The power set point Pset1 can be determined, for example, in the same or similar manner as Pset shown in FIG. 8B. In at least one embodiment, the power set point Pset1 can be 125 W, though it should be appreciated that other values can be used. In the described embodiment, the power generated by an electrosurgical generator, such as an RF generator, is controlled by regulating voltage and/or current so that a certain power level range is delivered and a maximum power level is not exceeded. The power is controlled with the goal of maintaining it around the power set point Pset1.

Section A of FIG. 12 illustrates variation of voltage (V) (graph 1210) and current (I) (graphs 1212) corresponding to the power P, as a function of time. As shown, the voltage V fluctuates between a zero value (or a value that is close to zero such that the electrodes do not deliver enough power to tissue to coagulate the tissue) and a predetermined upper threshold value V2, such as, e.g., 100V. A predetermined baseline voltage or a lower threshold value (e.g., 25V) is also shown in section A of FIG. 12 as V1. The voltage is regulated to remain between the zero value and the upper threshold V2, where the voltage above the lower threshold V1 is interpreted as a peak in voltage, indicating that the tissue is being coagulated.

As shown in section A of FIG. 12, in use, once the surgical tool is activated to cause its electrodes to deliver RF energy to the tissue, no voltage regulation occurs within a first time period Δts that follows the initial activation of the electrodes. As also shown in section A, at the beginning of the activation of the electrodes, the initial voltage Vs can be relatively high, such as. e.g., in one example, 130V. After the initial time period Δts, the power is controlled by regulating the voltage based on the sensed impedance. As shown, generally, an increase in the impedance results in a decrease in the power, and vice versa. Thus, section B of FIG. 12 shows, in the graphs 1208 and 1204 in section B, that a decrease of the impedance during a time period Δt1 corresponds to an increase in the power. Further, as discussed above regarding system 1100 of FIG. 11, the increase in the impedance generally results in an increase in the aspiration rate. Thus. FIG. 12 illustrates that, as the impedance increases during a time period Δt2 (graph 1204), the aspiration rate (graph 1202) also increases. The increase in the aspiration rate is followed by a proportional increase in the irrigation flow rate, wherein the increase in the irrigation flow rate occurs with a certain delay (shown as a time period Δt3), from a time when the increase in the aspiration rate occurs.

During a surgical procedure, an electrosurgical tool is manipulated such that its electrodes apply RF energy to various areas of a tissue being coagulated. Thus, the tool is manipulated such that the electrodes are moved on the tissue. Also, the tool can be manipulated such that the electrodes are lifted off the tissue (such that there is no contact with the tissue), the tool is moved (by moving a robotic arm to which it is coupled to another location at the surgical site), and the electrodes are returned into contact with the tissue at this other location. Such lifting off and moving to a new location of the electrodes can occur multiple times during the surgical procedure. The irrigation fluid can be delivered to a tissue at a surgical site being coagulated when the electrodes are near or in contact with the tissue. Moreover, in some embodiments, the irrigation fluid is delivered to the tissue at the surgical site only when the electrodes are determined to be in contact with the tissue. Whether or not the electrodes are in contact with the tissue can be determined in various ways.

In general, in the illustrated embodiments, the flow rate of an irrigation fluid depends on monitored tissue impedance that, in turn, is used to adjust power applied to the tissue. The power can be controlled, by a power generator and/or a control system configured to control the power generator, based on values of the monitored impedance and a time period during which the impedance has certain value(s). Furthermore, the monitored tissue impedance can be used to determine whether the electrodes are in contact with the tissue. Conductivity of the tissue is monitored and the power is initiated when the monitored conductivity indicates that electrodes are in contact with tissue. For example, in some embodiments, the power generator can be controlled to reduce power delivered through the electrodes when the monitored impedance exceeds a predetermined impedance maximum. The predetermined impedance maximum can be referred to as a tissue contacting threshold which the control system uses to determine, based on the monitored tissue impedance, whether the electrodes are in contact with the tissue. The tissue contacting threshold can be selected for a particular surgical procedure, for example, by calibrating the surgical tool to determine tissue reaction, such that a desired reaction to sensed low and high impedance states can be achieved. When the impedance is above the tissue contacting threshold and the power delivery is reduced or ceased, the flow rate of the irrigation fluid can be reduced or the irrigation can be ceased, to prevent tissue and blood from sticking to the electrodes. The predetermined tissue contacting threshold (or impedance maximum) can be selected by the surgeon or the version of the tool that communicates to the generator or robotic system. In other words, a procedure-specific instrument for liver, for example, may have a different predetermined impedance maximum than a procedure-specific instrument for orthopedic applications such as spine surgery.

In some embodiments, the power generator is controlled to reduce or cease power delivery through the electrodes when the monitored impedance exceeds a predetermined impedance maximum, and resume power delivery if the monitored impedance remains above the predetermined impedance maximum for a predetermined time period. The predetermined impedance maximum can be referred to as a tissue contacting threshold which the control system uses to determine, based on the monitored tissue impedance, whether the electrodes are in contact with the tissue. FIG. 12 shows, by way of example, a maximum impedance Za that is used to determine whether the electrodes are in contact with the tissue. When the impedance Z exceeds the maximum impedance Za, a peak or spike in the impedance Z is detected, and the power P is controlled accordingly. In some embodiments, the power can be controlled based on the duration of the impedance peak and the amplitude the impedance peak. For example, if the impedance spike above the maximum impedance Za is detected, the power to the power delivery through the electrodes can be ceased. If the impedance remains above the maximum impedance Za for a predetermined time period (e.g., the impedance does not drop as the power delivery is ceased), which indicates that the increase in the impedance was part of a proper tissue coagulation process, the power delivery can be resumed.

FIG. 12 shows, in section B, a spike or peak 1220 in the impedance Z shown in the graph 1204, where the impedance exceeds the tissue contacting threshold Za. In the graph 1204, the impedance peak 1220 exceeds a predetermined impedance maximum Za and the impedance remains above the predetermined threshold Za for the relatively short period of time ta. Thus, the impedance peak 1220 is considered indicative of the electrodes being lifted off the tissue. To decrease a risk of tissue sticking to the electrodes and tissue charring, such a short impedance spike event can cause the control system to cease power delivery to the electrodes or to decrease the power to a low level. As shown in the graph 1210 in section A, the impedance peak 1220 results in a peak in the voltage such that the voltage reaches the upper threshold V2 and then drops below the lower threshold V1, such as the power (graph 1208) and the current also decrease.

In some embodiments, a control system controls a generator to reduce power delivered to an electrosurgical tool. The power can be controlled to be reduced when measured tissue impedance exceeds a predetermined threshold. When the impedance is below the predetermined threshold (e.g., a tissue contacting threshold), the power can be delivered according to a load curve (i.e. a curve showing delivered power versus load impedance) that can be referred to as a full load curve. When it is detected that the tissue impedance exceeds the predetermined threshold, the power can be reduced. The tissue contacting threshold can be selected and optimized for a particular procedure and/or based on a technique used by a surgeon (e.g., based on reacting to sensed low and high impedance states). An irrigation fluid can be delivered by the electrosurgical device to a tissue at a treatment site when the electrodes are in contact with the tissue. Changes in tissue conductivity changes are sensed and the power is initiated when the electrodes are in contact with tissue.

In some embodiments, additionally or alternatively to using monitored tissue impedance to determine whether electrodes of an electrosurgical tool are in contact with the tissue, pressure exerted on the electrodes can be monitored to determine whether the electrodes are in contact with the tissue. The pressure exerted on the electrodes can be sensed (as a vector) and the flow rate of the irrigation can be controlled to increase as the pressure exerted on the electrodes increases. Thus, a suitable control system is configured to determine whether the tissue is contacted by the electrodes.

In some embodiments, in use, the degree of contact of the electrodes with the tissue is determined by a control system to assess a desired intent of a surgeon. For example, the electrodes can be maintained in nearly constant contact with the tissue, and the power level and irrigation flow rate are reduced over time to reduce heat and fluid build-up in the surgical site. In some embodiments, the power level can be reduced while the irrigation rate remains substantially the same or is increased to clear the surgical site of blood. Such techniques can be used in conjunction with various configurations of the surgical tool, including various implementations of an aspiration assembly.

Figure 13:
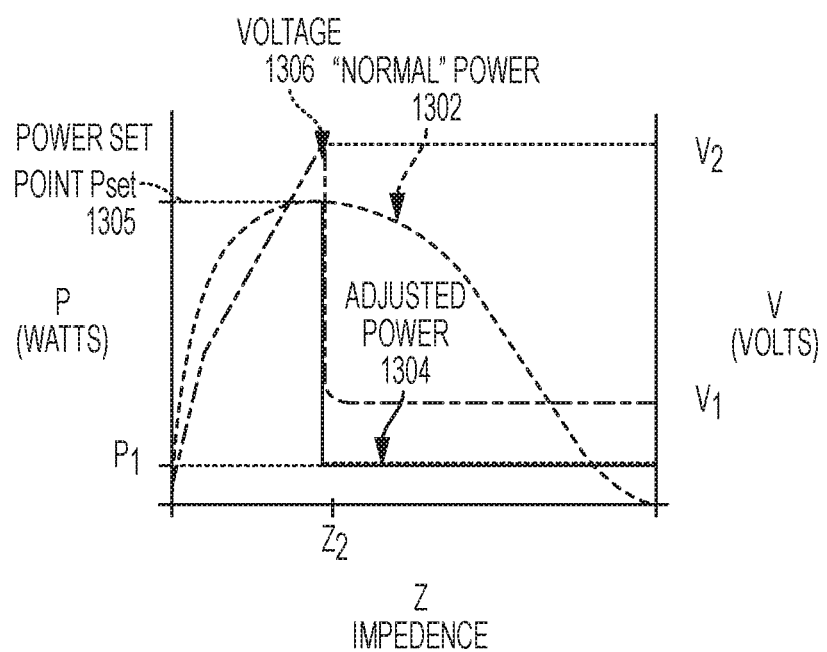
FIG. 13 shows graphs illustrating an example of power and voltage curves of a power generator as a function of monitored tissue impedance, the power curves including a curve showing "normal" power and a curve showing adjusted power when the impedance exceeds a maximum impedance.

FIG. 13 shows graphs illustrating controlling the power P and voltage V as a function of the impedance Z. In particular, a graph 1302 is "normal" (e.g., full load) power curve corresponding to the power applied when the tissue is being coagulated, and a graph 1304 shows adjusted power corresponding to power adjusted when a short spike in the impedance is detected. In this example, the normal power curve 1302 shows the power that increases from zero at a beginning of a surgical procedure, and reaches a power set point Pset, shown as a line 1305. As shown in FIG. 13, if the reduction of voltage (graph 1306), and therefore power, is not followed by a drop in the impedance (which indicates that the tissue is being coagulated), the power is controlled in accordance with the "normal" power curve 1302. The Pset can be determined, e.g., as shown for power set point Pset in FIG. 8B. A graph 1306 illustrates variation of the voltage V based on the impedance Z. As shown, when the impedance is below the predetermined threshold Za, the power is below the power set point Pset and its values are disposed on essentially one curve, such that the power curves of the graphs 1302, 1304 coincide. When the impedance exceeds the maximum impedance threshold Za, the power curves 1302 and 1304 deviate from one another. In particular, as shown in FIG. 13, the "normal" power curve 1302 plateaus for a certain time period around the Za value and continues to have the approximately bell-like shape (slightly skewed to the left, in this example). The power curve 1302 corresponds to a scenario when the tissue is being treated as desired, according to normal operating conditions.

In the event of a short impedance spike (such as, e.g., the peak or spike 1220 in FIG. 12), the voltage can be controlled such that it spikes to the upper threshold V2 (e.g., 100V) and then drops to the lower threshold V1 (e.g., 25V). When the reduction of voltage (and therefore power) results in the drop of impedance, this indicates that the electrodes of the electrosurgical tool have been lifted off the tissue (which resulted in the spike in the impedance). A generator load curve can be modified to prevent tissue sticking and charring. The V1 and V2 can have various suitable values, and, in at least one embodiment, V2 is about 100V and V1 is about 25V. As shown in FIG. 13, as the voltage (graph 1306) is decreased to V1, the power (graph 1304) is decreased to a baseline power level Pb, which can indicate that the power is zero or close to zero. In this way, when the high impedance is followed by the reduction of power, tissue sticking to electrodes and charring can be avoided. As shown in the graph 1304, the power can then remain at the level Pb.

In some embodiments, the electrosurgical tool can be operated such that the electrodes are in continuous contact with a tissue being treated. Additionally or alternatively, the electrosurgical tool can be operated in a mode such that the electrodes are brought in contact with the tissue for treating the tissue and then lifted off the tissue, where such operation can be repeated a number of times during a surgical procedure. As the electrodes are picked up off the tissue, moved, and returned to be in contact with the tissue multiple times, the power level and the flow rate of an irrigation fluid can be increased during time periods when the electrodes are in contact with the tissue. The power can be turned off or decreased and the flow rate of the irrigation fluid can be reduced or stopped when the electrodes are lifted off the tissue to prevent tissue and blood from sticking to the electrodes. During either of the operating modes (or during a combination mode that involves aspects from both of the modes), when a high tissue impedance is detected (e.g., the impedance exceeds a certain threshold), the controller will need to determine whether the electrodes are lifted off the tissue, or whether the conductivity of the tissue is low (i.e. an insufficient amount of irrigation fluid is delivered to the tissue), or whether the high tissue impedance is detected due to tissue properties (a high impedance tissue). When the high impedance is detected due to the tissue properties, no action may be required to be taken in response to the measured high tissue impedance.

As discussed above, in some embodiments, a control system is configured to vary a flow rate of an irrigation fluid and power delivered to an electrosurgical tool when an increase in tissue impedance is encountered, to limit voltage and therefore prevent tissue sticking and/or balancing conductivity. In some embodiments, when high tissue impedance is detected, the control system controls a generator to reduce the RF power delivered to the electrodes of the electrosurgical tool. For example, the power can be controlled using the power curves as shown in FIG. 13. If the reduction of power does not result in a decrease in the impedance (which may indicate that the electrodes are in contact with the tissue), the control system can control the electrosurgical tool to increase a flow rate of an irrigation fluid delivered to the treatment site. The flow rate can be controlled based on deviation of the power from a power set point, as shown, for example, in FIG. 9.

If the increase of the flow rate of the irrigation fluid does not cause the impedance to decrease (which may indicate that a high impedance tissue is encountered by the electrodes), the control system can control a generator to operate as if the impedance is lower than the actual detected impedance. In this way, the generator will increase the power as if the actual measured impedance were smaller than the detected impedance. In some embodiments, a control system (which can be part of control system 706 of FIG. 7) is configured to interrupt an electrical connection between a power generator and an end effector of a surgical tool when monitored impedance exceeds a predetermined threshold. For example, a resistor can be shorted to shift a load curve of the generator. The power generator can be sent a false signal, instructing the power generator to operate as if the connection has not been interrupted. For example, the control system can transmit manipulated tissue impedance data to the generator to cause the generator to deliver energy that it would not deliver based on unmanipulated impedance data because it would violate the generator's predetermined normal operating conditions. The control system can thus allow the robotic system to effect tissue treatment without the generator making changes to predetermined normal operating conditions (e.g., control curves). In at least some embodiments, the control system can operate to fool or spoof the generator as described in U.S. patent application Ser. No. 15/689,072 (now U.S. Pat. No. 10,932,808, entitled "Methods, Systems, and Devices For Controlling Electrosurgical Tools," filed on even date therewith, the entire content of which is incorporated by reference herein. For example, the control system can operate to control various switches, as discussed in U.S. patent application Ser. No. 15/689,072 (now U.S. Pat. No. 10,932,808).

Figure 14A:
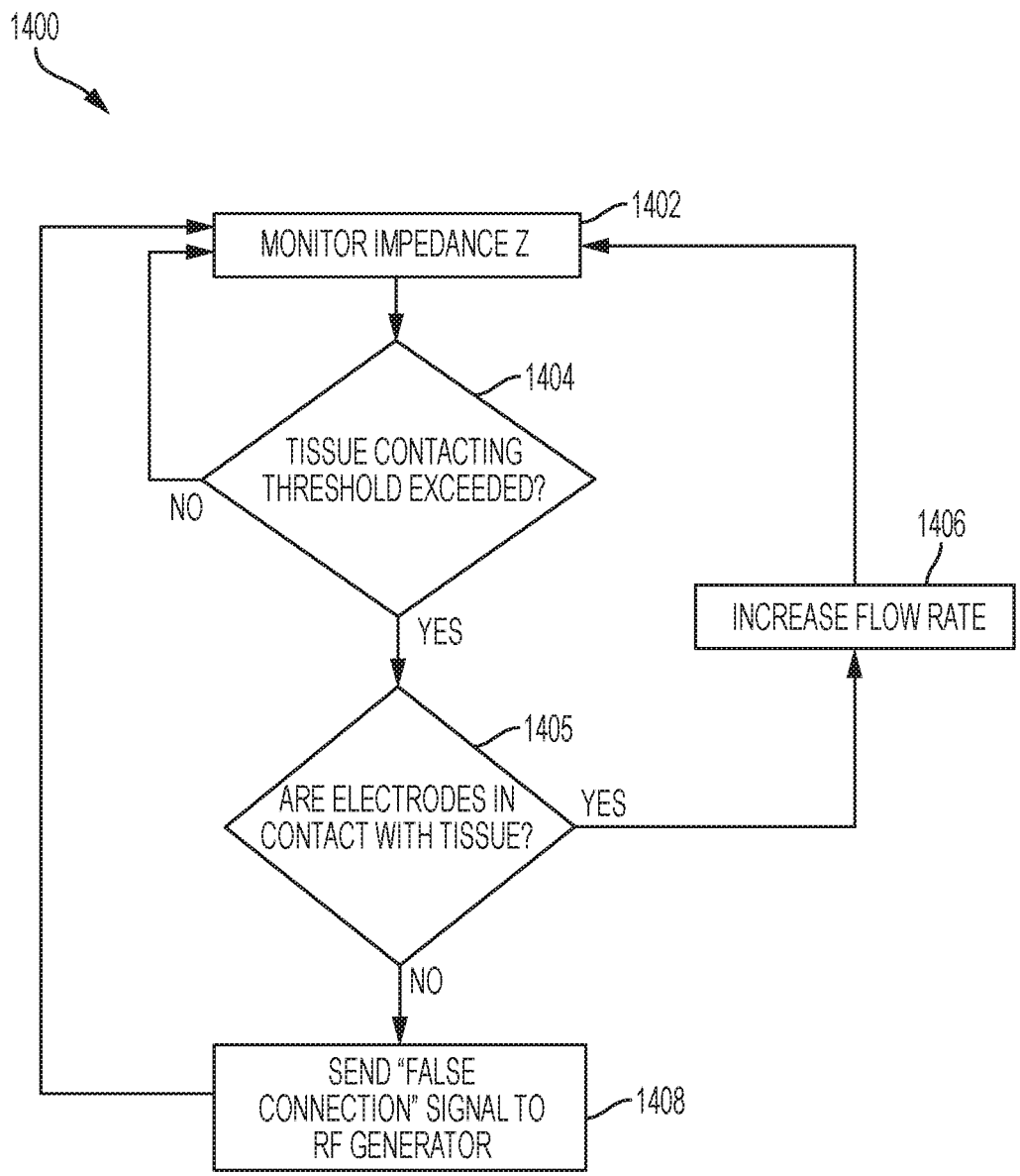
FIG. 14A is a flow chart illustrating an example of a process of controlling an electrosurgical tool when monitored tissue impedance exceeds a predetermined threshold.

FIG. 14A shows an example of a process 1400 of controlling operation of an electrosurgical tool when high tissue impedance is detected. As shown, the impedance is monitored at block 1402. At decision block 1404, it is determined, based on the monitored tissue impedance, whether a threshold tissue impedance is exceeded. The threshold impedance can be, e.g., a tissue contacting threshold. If the threshold tissue impedance is exceeded, the process 1400 follows to block 1405 where it is determined whether the electrodes are in contact with the tissue. If it is determined that the threshold tissue impedance is not exceeded, the process returns to block 1402, as shown in FIG. 12.

The processing at block 1405 can involve operating the control system using the power curves shown in FIG. 13. Thus, the power delivered to the electrodes can be decreased. If the reduction of power does not result in the decrease in the impedance, it can be determined that the electrodes are not in contact with the tissue. Alternatively, if the reduction of power results in the decrease in the impedance, it can be determined that the electrodes are in contact with the tissue. In this case, if it has been determined, at decision block 1405, that the electrodes are in contact with tissue, the flow rate of the irrigation fluid can be increased, as shown at block 1406, and the process 1400 can returns to block 1402.

However, if it is determined that the electrodes are not in contact with the tissue, in this example, the control system sends a "false connection" signal to the RF generator, at block 1408. The RF generator can then operate as if it is still connected to the electrodes, using predetermined logic functions that allow artificial ceasing power delivery to the electrodes or reducing the power delivered to the electrodes.

As also show in FIG. 14A, the control system can continue monitoring the tissue impedance, such that the process 1400 returns to block 1402. In some embodiments, the RF generator operates according to a power vs. load impedance curve with the "false connection" signal applied. For example, a load resistor connected to output terminals of the generator can emulate a tissue contact and shift the load curve, and therefore the power output of the generator, into another area of the load curve. In some embodiments, the "false connection" signal can be used by the control system to spoof the generator as described, for example, in U.S. patent application Ser. No. 15/689,072 (now U.S. Pat. No. 10,932,808) mentioned above.

It should be appreciated that the process 1400 is shown by way of example only and that various actions can be taken when it is determined that the tissue impedance is above a certain threshold. Also, the process 1400 can vary in different ways. For example, in some embodiments, whether or not the tool electrodes are in contact with the tissue can be determined (e.g., at block 1405 of FIG. 14A) based on pressure determined to be exerted on the electrodes. For example, the control system can use a force input from a motor configured to operate a robotic arm having the surgical tool coupled thereto, to determine whether the end effector is in contact with the tissue when the impedance is above a predetermined threshold. If a certain torque threshold is exceeded in a tool driver motor controlling movements of the tool's end effector (e.g., via controlling an instrument shaft having the end effector coupled thereto), such measure of a force resistance from the tissue can indicate that the electrodes are in contact with the tissue. If the torque threshold is not exceeded, it can be determined that the electrodes are not in contact with the tissue, and the generator can be fooled such that an artificial load turning off or decrease of the power delivered to the end effector can be performed.

Figure 14B:
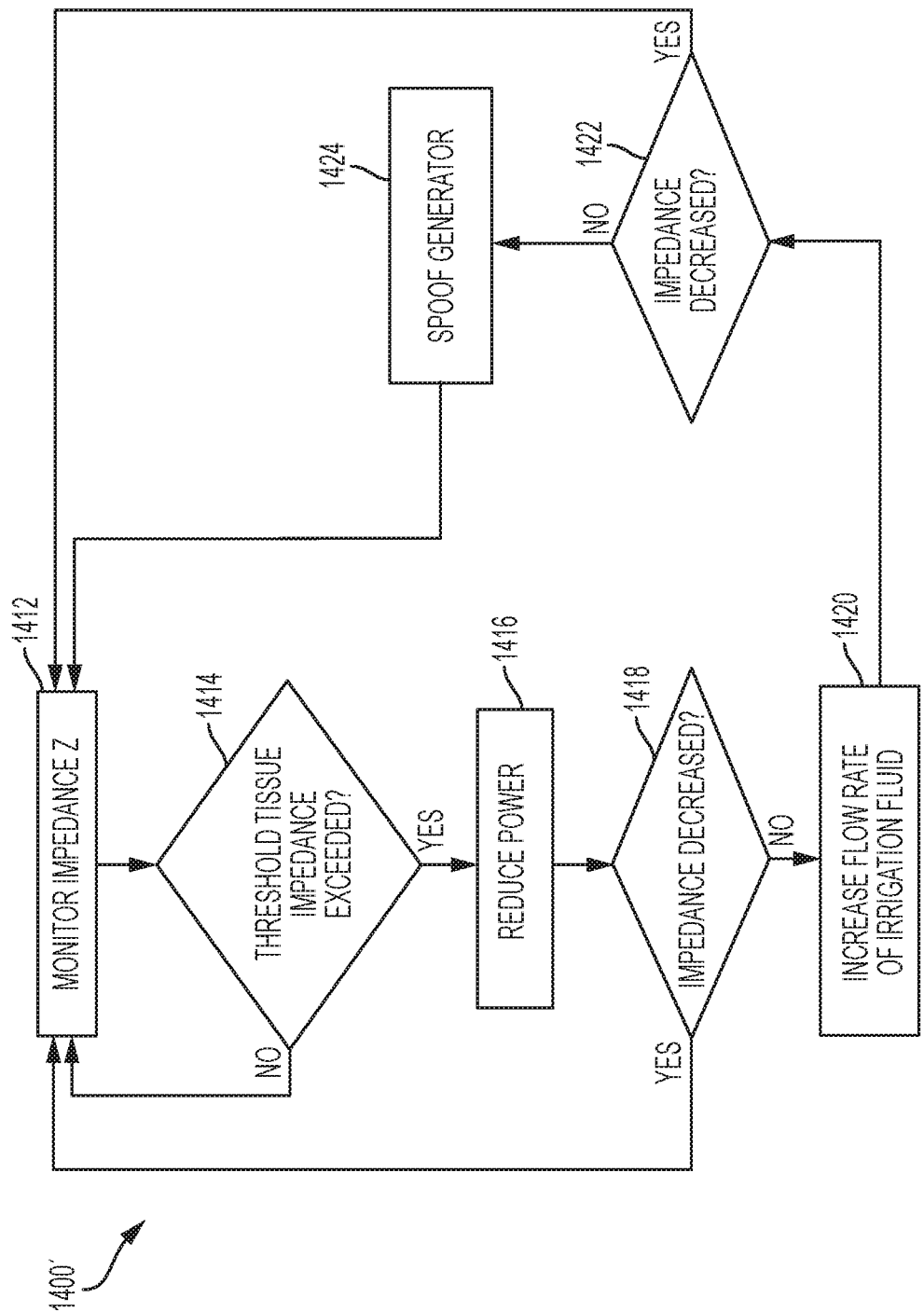
FIG. 14B is a flow chart illustrating another example of a process of controlling an electrosurgical tool when monitored tissue impedance exceeds a predetermined threshold.

FIG. 14B shows an embodiment of a process 1400' of controlling operation of an electrosurgical tool when tissue impedance is above a certain predetermined threshold. The impedance is monitored at block 1412. If it is determined, at block 1414, that the threshold tissue impedance is exceeded, the process 1400 follows to block 1416 where the power is reduced. The control system can control the electrosurgical tool using the power curves as shown, e.g., in FIG. 13. The power can be reduced (or, in some embodiments, turned off), and the flow rate of the irrigation fluid can be reduced or stopped.

Next, it is determined, at decision block 1418, whether the reduction of the power resulted in the decrease in the impedance. If this is the case, the process 1400' returns to block 1412 to further monitor the impedance. Alternatively, if the reduction of the power did not result in the decrease in the impedance, the process 1400' follows to the block 1420 where a flow rate of an irrigation fluid is increased. The flow rate can be controlled, e.g., based on a deviation of power from a power set point (e.g., in accordance with the control process shown in FIG. 9). If this results in the decrease in the impedance, which is determined at block 1422, the process 1400' returns to block 1412. Alternatively, if the increase in the irrigation fluid flow rate does not result in the decrease in the impedance (which may indicate, e.g., that a high impedance tissue is encountered by the electrodes), the generator can be spoofed, at block 1424. For example, as discussed above, the generator can be operated as if the impedance is lower than the actual measured impedance, such that the generator increases the power, even though it would normally decrease the power. The process 1400' can then return to block 1412. It should be appreciated that the process 1400' in FIG. 14B is shown to return to block 1412 after the processing at blocks 1418, 1422, 1424 by way of example only, as the process 1400' can terminate at any of blocks 1418, 1422, 1424. Furthermore, the order of the processes is shown in FIG. 14B by way of example only, and the processing at blocks 1416, 1420, 1424 can be performed in the order different from the order shown in FIG. 14B.

In some embodiments, a flow rate of an irrigation fluid through at least one fluid port of the surgical tool is controlled based on a rotational angle of the instrument shaft relative to a ground. For example, an electrosurgical tool can include first and second irrigation ports, and the flow rate through the ports can be controlled based on the shaft's rotational angle.

Furthermore, in some embodiments, an electrosurgical tool can include first and second ports that can interchangeably selectively operate as irrigation and aspiration ports. In such embodiments, the configuration of each port (i.e. whether it is currently delivers or aspirates a fluid) is controlled based on based on a rotational angle of the instrument shaft relative to a ground. The rotational angle is also used to control an irrigation flow rate of an irrigation fluid through one of the first and second ports, and an aspiration flow rate of fluids at the surgical site through another one of the first and second ports.

During treatment of tissue at a surgical site with electrodes of an electrosurgical tool, the tool's end effector having the electrodes can be disposed at various angles with respect to the tissue. Tissue impedance will change depending on the angle at which the electrodes are disposed, and different power thus should be applied to the tissue. Accordingly, in some embodiments, application of RF power to the tissue by the electrodes is controlled based on an orientation of the end effector with respect to the tissue. The end effector and a tool's shaft to which the end effector is coupled can be aligned such that they change the orientation with respect to the tissue together. Alternatively, the end effector can articulate with respect to the shaft (as shown for end effector 406 in FIGS. 5A and 5B). Regardless of whether the end effector is articulated with respect to the tool, as the angle of the end effector, and thus the electrodes, relative to the tissue changes, the RF power applied by the electrodes to the tissue can be adjusted accordingly. Also, as discussed in more detail below, the change in the angle of the end effector results in a change of a surface area of the tissue that is subjected to heat.

Figure 15A:
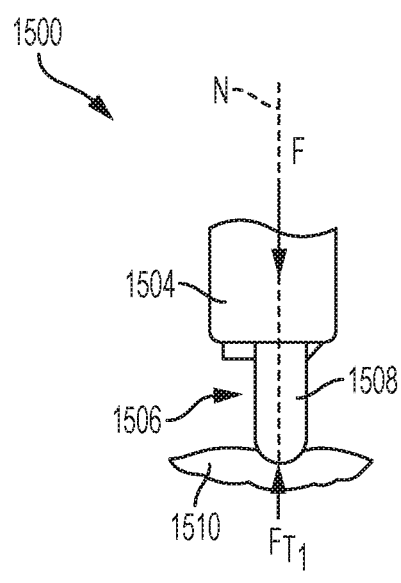
FIG. 15A is a perspective side view of one embodiment of a distal portion of an electrosurgical tool including an end effector with treatment electrodes, showing the end effector disposed in contact with a tissue such that a longitudinal axis of the end effector coincides with a gravity vector.
Figure 15B:
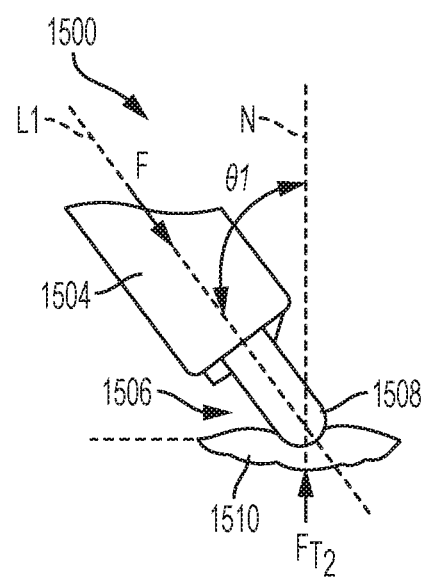
FIG. 15B is a perspective side view of the end effector of FIG. 15A, showing the end effector tilted such that it is at an angle with respect to the gravity vector.

FIGS. 15A and 15B illustrate an embodiment of an end effector 1506 coupled to an instrument shaft 1504 of a surgical tool 1500 treating a tissue 1510 that is shown schematically. The end effector 1506 has electrodes 1508 and it is similar, for example, to end effector 506 (FIGS. 5A and 5B), such that its description is not repeated herein. Thus, although not shown in FIGS. 15A and 15B, the end effector 1506 can include an irrigation port and an aspiration port, as well as other components. The surgical tool 1500 is configured to be coupled to a surgical robotic system configured to control operation of the surgical tool 1500, including application of RF power by the electrodes 1508 to the tissue 1510. In particular, at least one control system associated with the surgical robotic system controls application of RF power by the electrodes 1508 based on the orientation of the electrodes 1508 with respect to the tissue. Because orientation of joints of a robotic arm (and/or other components) having the surgical tool 1500 coupled thereto is known, the control system can measure an angle of the electrodes 1508 with respect to the tissue and can adjust RF power based on the measured angle. The control system also controls an amount of force (or pressure) applied by the electrodes 1508 to the tissue.

FIGS. 15A and 15B illustrate a side view of the end effector 1506, such that a side of one of the electrodes 1508 is shown while another one of the electrodes 1508 is obscured. FIG. 15A shows the end effector 1506 disposed at a zero angle θ with respect to an axis N normal to a "ground" that, for the purpose of this description, is the tissue. In other words, in the illustrated embodiment, the angle θ is a tilt or tilting angle of the end effector with respect to a gravity vector. At such position of the end effector 1506 relative to the tissue 1510, both of the electrodes 1508 apply a compressive force F to the tissue 1510, and the tissue 1510, in turn, applies a resistive force $F_{T1}$ against the electrodes 1508, as shown in FIG. 15A. The resistive force applied by the tissue 1510 to the electrodes 1508 in contact with the tissue can be measured, for example, by using suitable pressure sensors, and/or using other devices. The robotic system can acquire from the tool 1500 information on the resistive force experienced by the electrodes, which allows the robotic system to determine a change in the angle of the end effector. A resulting contact force $F_T$ exerted by the electrodes 1508 (their tips) (positioned as shown in FIG. 15A) to the tissue 1510 is determined based on the compressive force F and resistive force $F_{T1}$. Section B of FIG. 16 illustrates a graph 1602 showing a contact force $F_T$ as a function of an angle θ of the electrodes 1508 relative to the tissue.

In some embodiments, the contact force $F_T$ exerted by the electrodes 1508 to the tissue can be determined by sensing torque (e.g., using a torque sensor) of a motor controlling operation of a robotic arm (e.g., robotic arm 108 in FIG. 1) having the tool with the electrodes 1508 coupled thereto. The determined torque is used to access the amount of force being applied to the motor when the electrodes are in contact with the tissue.

FIG. 15B shows an example of the end effector 1506 being angled with respect to the tissue 1510 such that the end effector 1506 is disposed at a non-zero, acute angle θ1 with respect to the axis N normal to the tissue. In this embodiment, the angle θ is shown as an angle between a longitudinal axis L1 of the effector 1506 and the axis N normal to the tissue 1510. Further, in this embodiment, the end effector 1506 can be angled relative to the tissue 1510 such that both of the electrodes 1508 are angled in the same manner, i.e., forward or backward, rather than sideways. In this way, both of the electrodes 1508 apply substantially the same compressive force to the tissue. It should be appreciated that the end effector 1506 is shown tilted to the left in FIG. 15A by way of example only as, in use, it can be angled in the opposite direction. At the angled position of the end effector 1506, the electrodes 1508 apply the compressive force F to the tissue 1510, and the tissue 1510 applies a resistive force $F_{T2}$ to the electrodes 1508, as shown in FIG. 15B. It should be appreciated that the compressive force and the resistive force for the two electrodes can be averaged.

Figure 16:
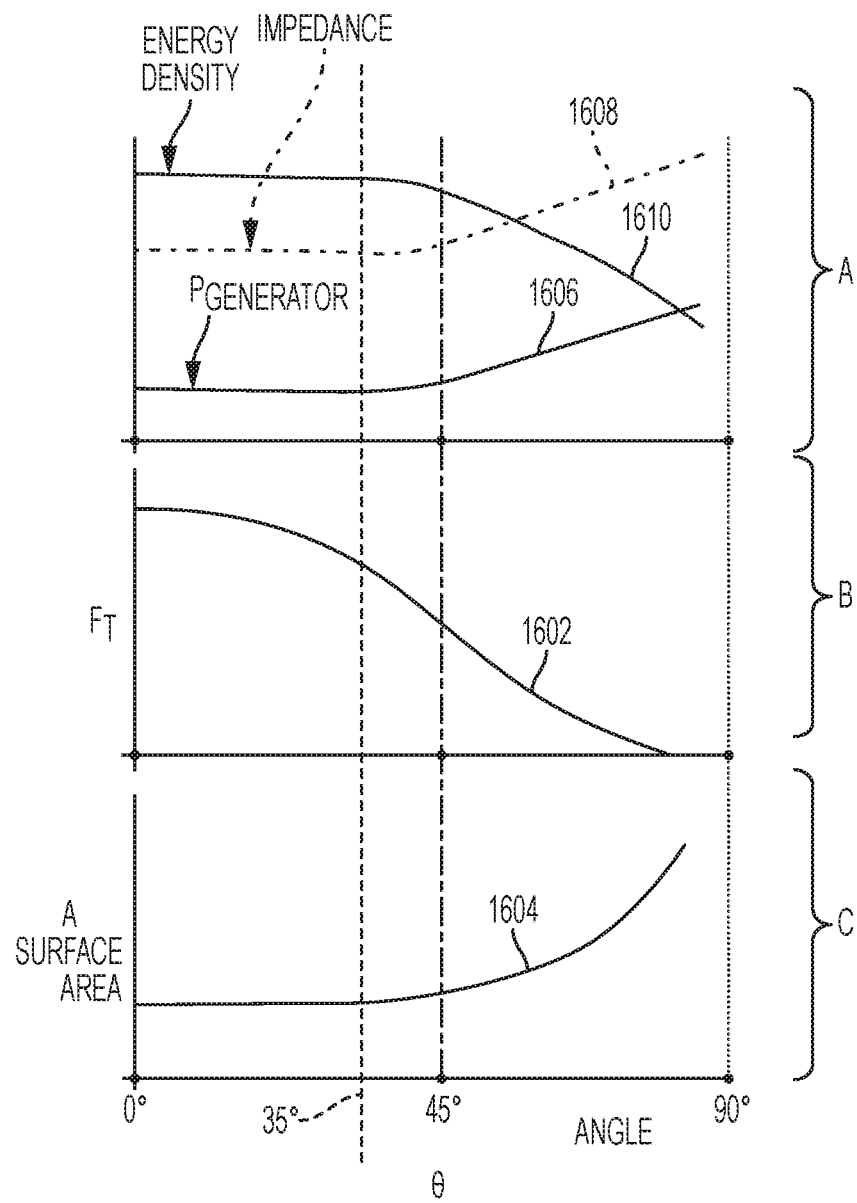
FIG. 16 shows graphs illustrating an example of variation of parameters as a function of the angle of the end effector of FIG. 15A with respect to the gravity vector, the parameters including monitored tissue impedance, generator power, energy density, contact force exerted by the electrodes on tissue, and a surface area of the electrodes in contact with the tissue.

As the angle θ, which, in this embodiment, is measured as an angle between a longitudinal axis L1 of the effector 1506 and the axis N normal to the tissue 1510, increases, the contact force $F_T$ that the tissue 1510 experiences decreases, as shown in the graph 1602 in FIG. 16. It should be noted that, in the illustrated embodiment, as the orientation of the electrodes 1508 with respect to the tissue changes such that the electrodes 1508 are moved from being generally perpendicular to the tissue 1510 (as shown in FIG. 15A) to being angled with respect to the tissue 1510, the angle θ is considered to increase. As further shown in FIG. 16, as the angle θ increases, a surface area A of the electrodes 1508 that is in contact with the tissue 1510 increases, as shown by a graph 1604 in section C of FIG. 16 illustrating the surface area A as a function of the angle θ. When the contact force $F_T$ decreases and the surface area A increases, to maintain appropriate level of the RF energy applied to the tissue, it is required to increase the RF power delivered by the electrodes 1508 to the tissue 1510. Thus, in some embodiments, the control system is configured to control a power generator to increase the RF power provided to the electrodes 1508 that apply the RF power to the tissue. FIG. 16 shows, in section A, a graph 1606 illustrating a variation of the RF power ("Pgenerator") provided by the generator, as a function of the angle θ defining an angle of the electrodes 1508 relative to the tissue.

A current or energy density of the electrodes, such as amount of electrical current passed through a certain area of the tissue (defined as the total amount of current divided by the surface areas of the electrodes), generally decreases as the electrodes' surface area in contact with the tissue increases. Thus, a graph 1608 in section A of FIG. 16 shows the amount of energy density ("Energy Density") as a function of the angle θ. The total amount of the electrical current flowing into the tissue depends on the amount of the power delivered by the RF generator and the encountered impedance (or resistance) of the tissue. A graph 1610 in section A of FIG. 16 shows the variation of the impedance ("Impedance") of the tissue as a function of the angle θ. In particular, as the power delivered by the RF generator is increased based on the increase of the angle θ, the impedance of the tissue also increased proportionally to the increase in the power.

As shown in FIG. 16, in this example, the power (graph 1606) remains substantially the same as the angle θ increases from zero to a certain angle, such as about 35 degrees. As the angle reaches about 35 degrees, the power is slowly increased. When the angle reaches 45 degrees, the surface area (graph 1604) increases at a higher rate, and the power (graph 1606) is increased at a higher rate.

In the illustrated embodiment, the control system of the surgical robotic system is configured to control the RF generator to adjust the RF power depending on the angle θ defining an angle of the electrodes 1508 relative to the tissue. In some implementations, however, the control system may not be able to control the RF generator. In such implementations, the control system can be configured to instruct the electrodes of the surgical tool to increase the contact force applied to tissue as the electrodes are angled with respect to the tissue (e.g., such that the angle θ as shown in FIGS. 15B and 16 increases). In this way, the compressive force, shown as F in FIGS. 15A and 15B, will change to reflect a change in the electrodes' angle and the resulting increase of the surface area.

Figure 17A:
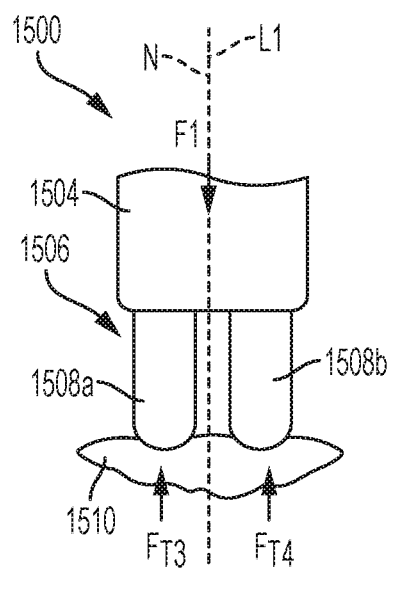
FIG. 17A is a perspective front view of one embodiment of a distal portion of an electrosurgical tool including an end effector with treatment electrodes, showing the end effector disposed in contact with a tissue such that a longitudinal axis of the end effector coincides with a gravity vector.
Figure 17B:
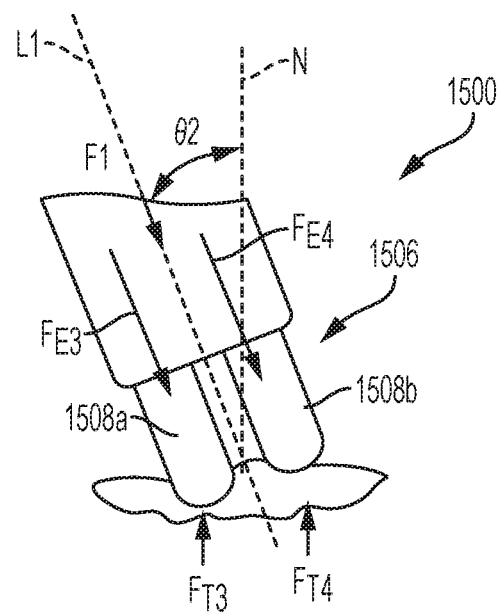
FIG. 17B is a perspective front view of the end effector of FIG. 17A, showing the end effector tilted such that it is at an angle with respect to the gravity vector.
Figure 18:
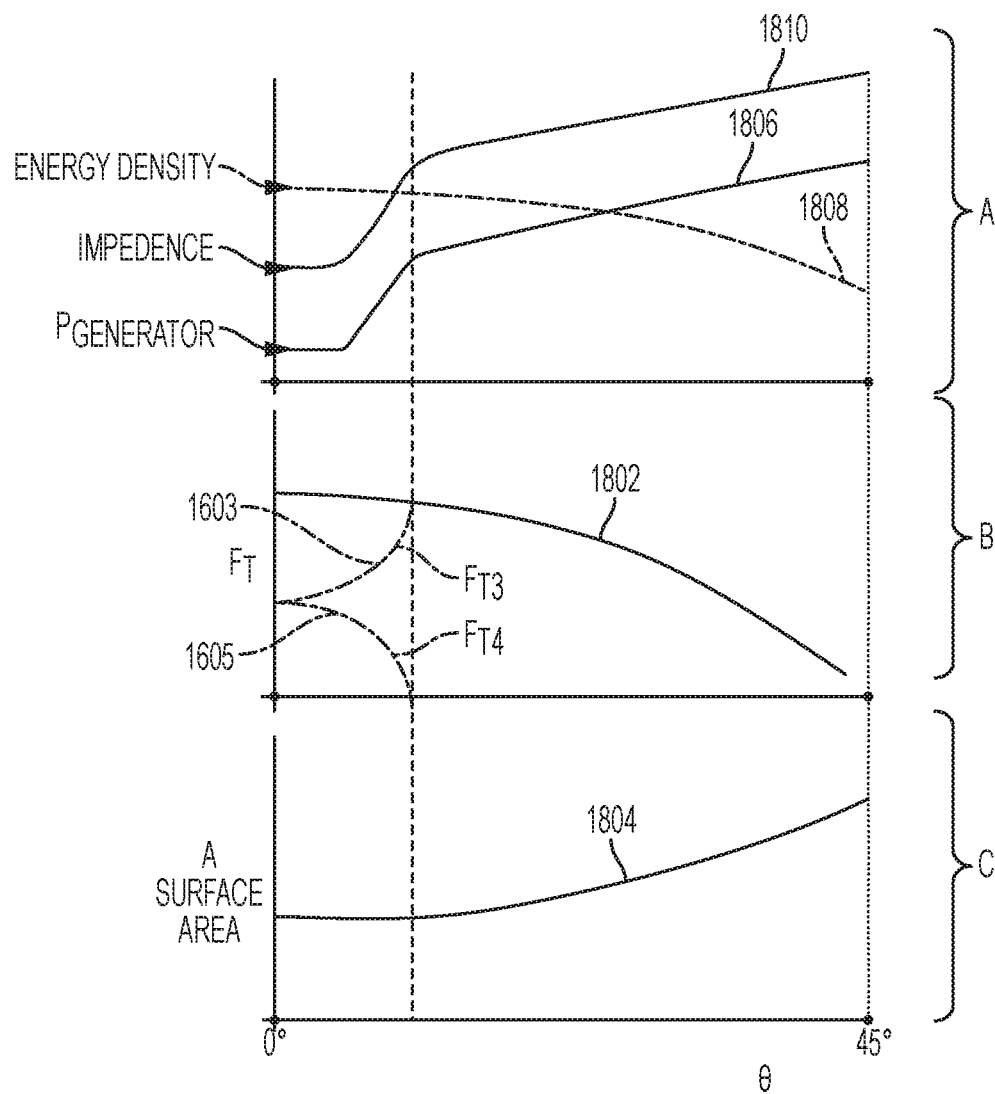
FIG. 18 shows graphs illustrating an example of variation of parameters as a function of the angle of the end effector of FIG. 17A with respect to the gravity vector, the parameters including monitored tissue impedance, generator power, energy density, contact force exerted by each of the electrodes on tissue, and a surface area of the electrodes in contact with the tissue.

FIGS. 17A, 17B, and 18 illustrate another example of a controlling RF power based on an angle of an end effector, and thus the electrodes, with respect to the tissue. FIGS. 17A and 17B illustrate a front view of the end effector 1506 of the surgical tool 1500 such that both first and second electrodes 1508a, 1508b are shown. In this example, the end effector 1506 can be angled sideways such that the electrodes 1508a, 1508b apply different contact forces to the tissue 1510.

FIG. 17A illustrates the electrodes 1508a, 1508b disposed at a zero angle θ with respect to an axis N normal to a "ground" that, for the purpose of this description, is the tissue. Thus, the longitudinal axis L1 of the effector 1506 coincides with the axis N normal to the tissue. At such position of the end effector 1506, the electrodes 1508 apply a compressive force F1 to the tissue 1510, and the tissue 1510, in turn, applies resistive forces $F_{T3}$, $F_{T4}$ against the electrodes 1508a, 1508b, respectively, as shown in FIG. 17A. In the example of FIG. 17A, the resistive forces $F_{T3}$, $F_{T4}$ against the electrodes 1508a, 1508b are substantially the same.

FIG. 17B shows an example in which the electrodes 1508a, 1508b are disposed at acute angle θ2, measured between the longitudinal axis L1 of the effector 1506 and the axis N. In this example, the second electrode 1508b applies less force to the tissue as the electrodes are angled. For example, as shown in FIG. 17B, as the end effector 1506 is angled sideways (to the left, in this example), the first electrode 1508a is pressed with greater force into the tissue. The resistive forces $F_{T3}$, $F_{T4}$ applied by the tissue 1510 to the electrodes 1508a, 1508b are therefore different, such that the resistive force $F_{T3}$ is greater than the resistive force $F_{T4}$. Thus, the first electrode 1508a applies a contact force $F_{E3}$ that is greater than a contact force $F_{E3}$ applied by the second electrode 1508b. Accordingly, the RF power provided to the electrodes is controlled based on how much power needs to be delivered to the second electrode 1508b.

FIG. 18 shows, in section B, a graph 1802 illustrating a combined contact force $F_T$ applied by both of the electrodes 1508a, 1508b to the tissue, as a function of the angle θ. The power can be controlled based on an angle of the end effector and therefore a force of the lighter one of the electrodes 1508a, 1508b. Section B also shows separate graphs 1603, 1605 illustrating the respective contact forces $F_{E3}$, $F_{E4}$ applied by the electrodes 1508a, 1508b to the tissue, respectively. As shown in section B of FIG. 18, in this example, when the end effector is not tilted or tilted only slightly to the left, the resistive forces $F_{T3}$, $F_{T4}$ (and the respective contact forces $F_{E3}$, $F_{E4}$) are substantially equal to one another. As the end effector is angled further to the left relative to the axis N, the resistive force $F_{T3}$ applied to the first electrode 1508a increases proportionally to a decrease in the force $F_{T4}$ applied to the second electrode 1508b. The respective contact forces $F_{E3}$, $F_{E4}$ change similarly. The force applied by the second electrode 1508b to the tissue is used to control power. As the electrodes are angled, the second electrode 1508b becomes lifted off the tissue 1510 and the resistive force $F_{T4}$ decreases. At a certain angle, such as, in this example, about 10 degrees, the resistive force $F_{T4}$ becomes zero when the second electrode 1508b is no longer in contact with the tissue. Thus, as shown in FIG. 18, the tissue impedance ("Impedance," graph 1810) between the electrodes increases and the RF power ("Pgenerator," graph 1806) increases.

As shown in a graph 1804 in section C of FIG. 18, the surface area A of the electrodes in contact with the tissue increases as the angle θ increases. Similar to the example of FIGS. 15A to 16, the RF power increases as the end effector 1506 is oriented such that the angle θ increases, as shown in the graph 1806 in section A. As also shown in section A of FIG. 18, the tissue impedance (graph 1810) increases as the angle θ increases, and the energy density ("Energy Density," graph 1808) decreases as the angle θ increases.

In the illustrated embodiments, as discussed above, an end effector of a surgical tool includes first and second electrodes, as well as irrigation and aspiration ports of respective irrigation and aspiration lines or tube. A surgical tool in which some embodiments can be implemented can include first and second irrigation ports. Such surgical tool has a conduit configured to selectively communicate an irrigation fluid between a fluid source and at least one of the first and second irrigation ports. Control of a flow rate of the fluid delivered through the first and second irrigation can take gravity into consideration, with the goal of keeping both the electrodes wet. In particular, when an instrument shaft with the end effector having the first and second irrigation ports is disposed substantially parallel to the ground, such that the first and second irrigation ports are disposed at the same height from the ground, a first flow rate of the irrigation fluid through the first port is substantially the same as a second flow rate of the irrigation fluid through the first port. However, as the instrument shaft is rotated relative to the ground, a flow rate of the irrigation fluid through a port that is farther from the ground increases, and a flow rate of the irrigation fluid through another port that is closer to the ground decreases.

Accordingly, a surgical system is provided that includes an electrosurgical device including an instrument shaft and an end effector formed at a distal end thereof, the end effector having first and second electrodes that are opposed to each other and first and second fluid ports adjacent to the first and second electrodes. The surgical system also has at least one conduit configured to selectively communicate an irrigation fluid between a fluid source and at least one of the first and second irrigation ports, and a control system configured to monitor a rotational angle of the shaft relative to a ground and to increase a flow rate of the irrigation fluid through the first port when the rotational angle exceeds a first predetermined angle and to decrease a flow rate of the irrigation fluid through the second irrigation port when the flow rate of the irrigation fluid through the first irrigation port increases.

Figure 19A:
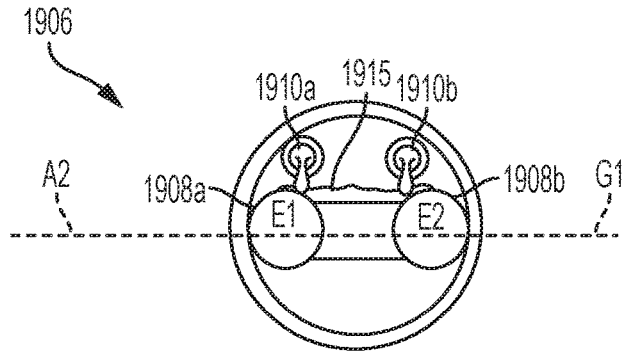
FIG. 19A is a distal end view of one embodiment of an end effector of an electrosurgical tool including first and second treatment electrodes and first and second ports, showing the end effector disposed at a zero rotational angle with respect to a ground.
Figure 19B:
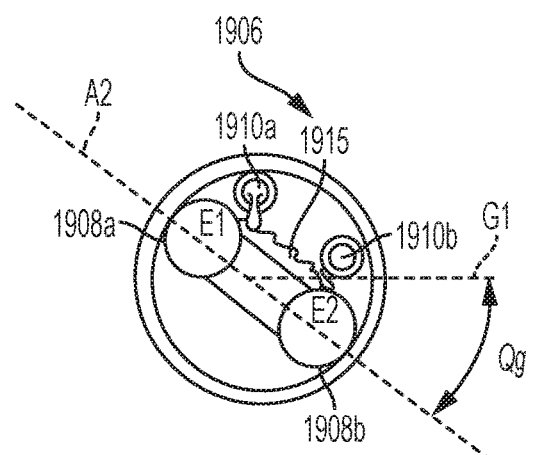
FIG. 19B is a distal end view of the end effector of FIG. 19A, showing the end effector disposed at a rotational angle with respect to the ground.

FIGS. 19A and 19B show one embodiment of an end effector 1906 including first and second electrodes 1908a, 1908b (also marked as "E1" and "E2") that are opposed to each other and first and second irrigation ports 1910a, 1910b adjacent to the first and second electrodes 1908a, 1908b. Although not shown in FIGS. 19A and 19B, the end effector 1906 is coupled to a distal end of an instrument shaft of an electrosurgical device. The electrosurgical device can be similar, for example, to tool 300 (FIG. 2). The electrosurgical device having the end effector 1906 also includes a conduit configured to selectively communicate an irrigation fluid between a fluid source and at least one of the first and second irrigation ports 1910a, 1910b. Although not shown in FIGS. 19A and 19B, it should be appreciated that the conduit is similar to an irrigation port, such as irrigation port 310 in FIG. 2. Thus, similar to the irrigation port 310, the conduit communicates an irrigation fluid from a fluid source (e.g., fluid source 324 in FIG. 2) to a port at the distal end of the end effector. However, in this embodiment, the conduit selectively communicates the irrigation fluid from the fluid source to one of the first and second irrigation ports 1910a, 1910b. It should be noted that, like in the other embodiments described herein, the irrigation fluid is a conductive fluid used to increase conductivity of a tissue being treated by the first and second electrodes 1908a, 1908b. Also, it should be appreciated that the end effector 1906 is shown by way of example only and that the electrodes and the ports can be disposed in other ways with respect to each other.

The electrosurgical device having the end effector 1906 is configured to be coupled to a surgical robotic system that controls, via a control system, a flow rate of the fluid through the first and second irrigation ports 1910a, 1910b. In particular, the control system (e.g., control system 706 in FIG. 7) is configured to monitor a rotational angle of the instrument shaft relative to a ground. FIG. 19A shows the end effector 1906 positioned at a zero angle with respect to a ground shown schematically as a dashed line G1. Thus, a plane A2 extending through the electrodes 1908*a*, 1908*b* is parallel to the ground G1, as schematically shown in FIG. 19A. It is understood that the ground G1 can be defined as a normal to a gravity vector. At the position of the end effector 1906 shown in FIG. 19A, the control system controls the conduit (e.g., by controlling a suitable pump in fluid communication with the conduit) to deliver the irrigation fluid through both of the first and second ports 1910*a*, 1910*b* at substantially the same rate. Thus, FIG. 19A shows schematically an irrigation fluid 1915 accumulated evenly around the first and second ports 1910*a*, 1910*b*.

Figure 20:
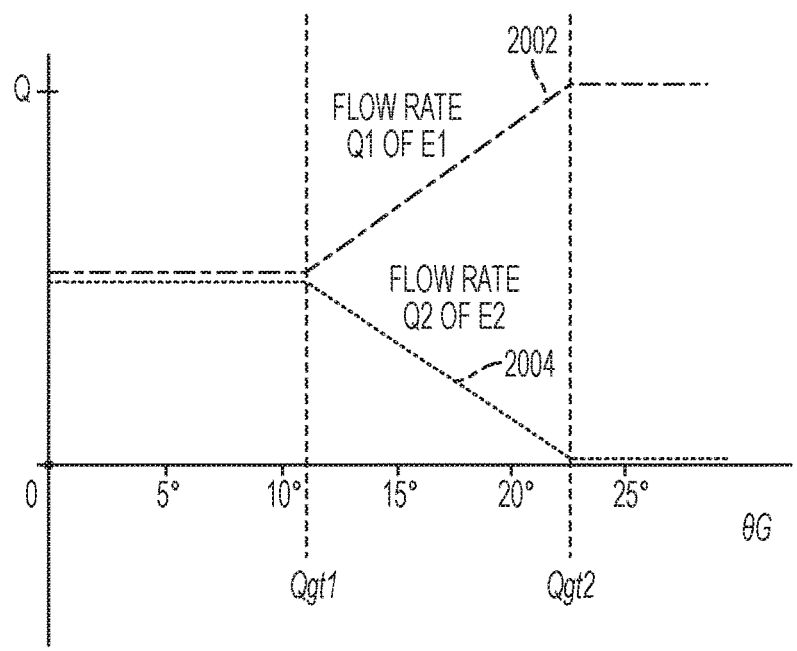
FIG. 20 shows graphs illustrating variation of a flow rate of an irrigation fluid through the first and second ports of the end effector of FIGS. 19A and 19B, as a function of the rotational angle of the end effector with respect to the ground.

When the instrument shaft is rotated with respect to the ground G1 such that the plane A2 extending through the electrodes 1908*a*, 1908*b* is oriented at an angle θg relative to the ground G1, as shown in FIG. 19B, the control system controls the conduit to change the flow rates of the irrigation fluid through the first and second ports 1910*a*, 1910*b*. The flow rate of the irrigation fluid through the first port 1910*a* can be increased when the rotational angle θg exceeds a first threshold, and the flow rate of the irrigation fluid through the second port 1910*b* is decreased when the flow rate of the irrigation fluid through the first port 1910*a* increases. FIG. 20 illustrates graphs for the flow rate Q of an irrigation fluid through a port as a function the rotational angle θg. As shown in FIG. 20, a flow rate Q1 through the first port 1910*a* (a graph 2002) and the flow rate Q2 through the second port 1910*b* (a graph 2004) remain substantially the same while the rotational angle θg of the instrument shaft is less than a first predetermined angle θgt1 (e.g., about 12 degrees, in this example).

In the illustrated embodiment, when the rotational angle θg exceeds the first threshold angle θgt1, the control system controls the conduit (e.g., by controlling the suitable pump) to increase the flow rate of the irrigation fluid through the first port 1910*a* and to decrease the flow rate of the irrigation fluid through the second irrigation port 1910*b*. In this example, the first port 1910*a* is located farther from the ground than the second port 1910*b*. In this way, a flow rate through the port that is disposed more "on top" of the electrodes is controlled to be increased while a flow rate of the port disposed lower is decreased. The first port 1910*a* thus provides the fluid to flow the fluid over the tissue and both of the electrodes. This occurs until the rotational angle θg is below a second threshold angle θgt2 (e.g., about 22.5 degrees, in this example). Thus, as shown in FIGS. 19B and 20, when the rotational angle θg exceeds the second threshold angle θgt2, the flow rate through the first port 1910*a* (graph 2002) remains the same, whereas the flow rate through the second port 1910*b* (graph 2004) becomes zero such that no fluid is provided to the surgical site through the second port 1910*b*. In this embodiment, as the instrument shaft is rotated with respect to the ground G1, the flow rates of the irrigation fluid through the first and second ports 1910*a*, 1910*b* will change, in accordance with the graphs 2002, 2004 in FIG. 20. It should be appreciated that the first and second threshold angles θgt1, θgt2 are shown in FIG. 20 by way of example only, as other angles can be used as first and second threshold angles. For example, in at least one embodiment, when the rotational angle θg is less than 15 degrees, both first and second ports 1910*a*, 1910*b* provide irrigation fluid, and when the rotational angle θg exceeds 15 degrees, the top-most port (e.g., the port 1910*a* in FIG. 19B) provides the fluid. The flow rate of the fluid provided through at least one of the ports can be decreased gradually or all at once, based on a threshold angle.

In some embodiments, both a flow rate of an irrigation fluid and an aspiration rate of fluids through first and second ports of an end effector of an electrosurgical tool can be selectively controlled based on a rotational angle of an instrument shaft of the electrosurgical tool relative to a ground. The first and second ports are coupled to at least one conduit configured to selectively communicate an irrigation fluid between a fluid source and at least one of the first and second ports and to selectively aspirate fluid (e.g., a spent irrigation fluid) between another one of the first and second ports and a vacuum source. In other words, each of the first and second ports can interchangeably operate as an irrigation port through which an irrigation fluid is delivered to the surgical site or an aspiration port through which the irrigation fluid is eliminated or aspirated from the surgical site. Furthermore, the conduit is controlled such that a flow rate of a delivered fluid and an aspiration rate of an aspirated fluid are increase or decrease depending on the rotational angle of the instrument shaft.

The at least one conduit, configured to provide selective fluid communication between each of the first and second ports and an irrigation fluid source and a vacuum source, can be in various forms. For example, it can include any of irrigation and aspirations conduits or tubes described herein. As another example, in some embodiments, the conduit can include tubes that can communicate fluid either from the surgical site (aspiration) or to the surgical site (irrigation).

The flow rate of a fluid delivered to the surgical site is controlled by controlling operation (e.g., a speed of rotation) of a peristaltic pump. In some embodiments, the aspiration is controlled by controlling an aspiration rate (or vacuum) that is a rate of change of in pressure differential over time, measured in millimeters of water (mm H2O) or mercury (mm Hg). However, in other embodiments, the aspiration can also be defined in terms of an aspiration flow rate, which is a flow of a fluids (measured, e.g., in cc/min or cc/sec) through a conduit or tube. For example, a peristaltic pump can be used to control the aspiration flow rate such that the aspiration flow rate is determined by the speed of the pump. In the illustrated embodiment in which the first and second ports can interchangeably operate to deliver or evacuate fluids from a surgical site, a control system of a robotic system can be configured to control at least one peristaltic pump to cause fluids to be delivered or aspirated through a port of the first and second ports. Thus, the conduit, configured to provide selective fluid communication between each of the first and second ports and an irrigation fluid source and a vacuum source, can be operatively coupled to a peristaltic pump that is operated by a suitable motor to control a fluid flow rate or an aspiration flow rate through the first and second ports.

Figure 21:
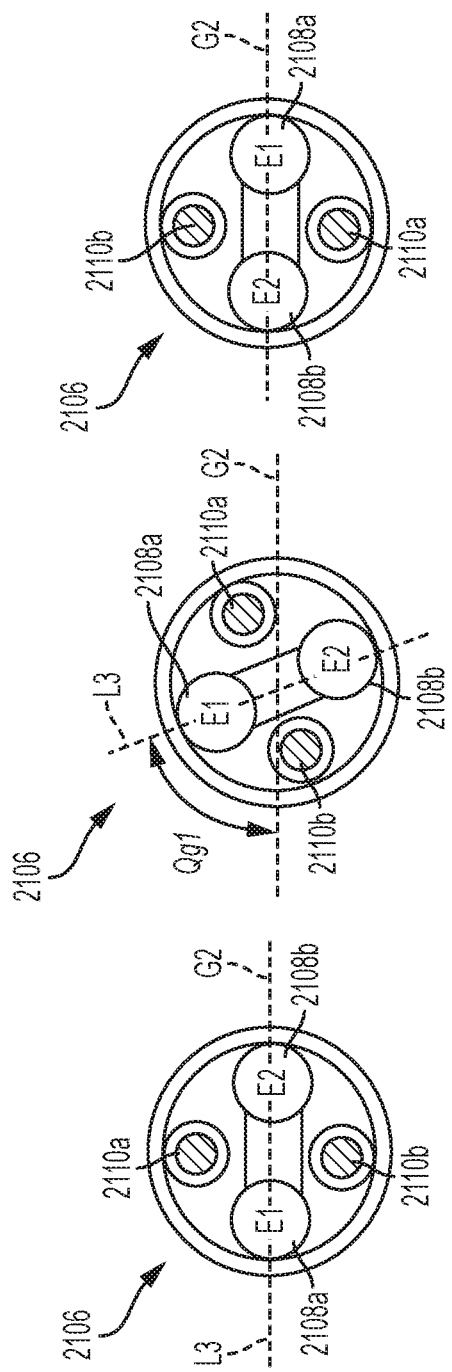
FIG. 21A is a distal end view of one embodiment of an end effector of an electrosurgical tool including first and second treatment electrodes and first and second ports, showing the end effector disposed at a zero rotational angle with respect to a ground, wherein the first port operates as an irrigation port and the second port operates as an aspiration port.
FIG. 21B is a distal end view of the end effector of FIG. 21A, showing the end effector disposed at a first rotational angle with respect to the ground, wherein the first port operates as an irrigation port and the second port operates as an aspiration port.
FIG. 21C is a distal end view of the end effector of FIG. 21B, showing the end effector disposed at a second rotational angle with respect to the ground that is greater than the first rotational angle, wherein the first port operates as an aspiration port and the second port operates as an irrigation port.

FIGS. 21A-21C and 22 show one embodiment of an end effector 2106 coupled to a distal end of an instrument shaft of an electrosurgical device. In this example, the end effector 2106 has first and second electrodes 2108*a*, 2108*b* that are opposed to each other, and first and second fluid ports 2010*a*, 2010*b* adjacent to the first and second electrodes 2108*a*, 2108*b*. In particular, as shown in FIGS. 21A-21C, the first fluid port 2110*a* is disposed between the first and second electrodes 2108*a*, 2108*b* (shown as "E1" and "E2") on one side of a distal end of the end effector 2106, and the second fluid port 2110*b* is also disposed between the first and second electrodes 2108*a*, 2108*b* and it is diametrically opposed to the first fluid port 2110*a*. The surgical system including the electrosurgical device also has first and second conduits coupled to the first and second fluid ports 2010*a*, 2010*b*, respectively. Each of the first and second conduits is configured to selectively communicate an irrigation fluid between a fluid source and a port to which the conduit is coupled or to selectively aspirate a fluid through the port, depending on a rotational angle of the instrument shaft with respect to the ground.

FIG. 21A shows the end effector 2106 in the position in which it is disposed at a zero angle with respect to the ground G2. In this position, an axis L3 extending through both the first and second end effectors 2108a, 2108b is substantially parallel to the ground G2. Further, in the position of the end effector 2106 as shown in FIG. 21A, the first port 2110a, which is a top port relative to the gravity, operates as an irrigation port delivering an irrigation fluid at a first irrigation flow rate, and the second port 2110b (a bottom port relative to the gravity) operates as an aspiration port aspirating fluids at a first aspiration flow rate. It should be noted that, depending on the implementation of the surgical tool, the aspiration through a port can be measured as an aspiration rate (measured, e.g., in mm H2O or mm Hg) and/or aspiration flow rate (measured, e.g., in cc/min or cc/sec), and that the aspiration rate is discussed in this embodiment by way of example only.

Figure 22:
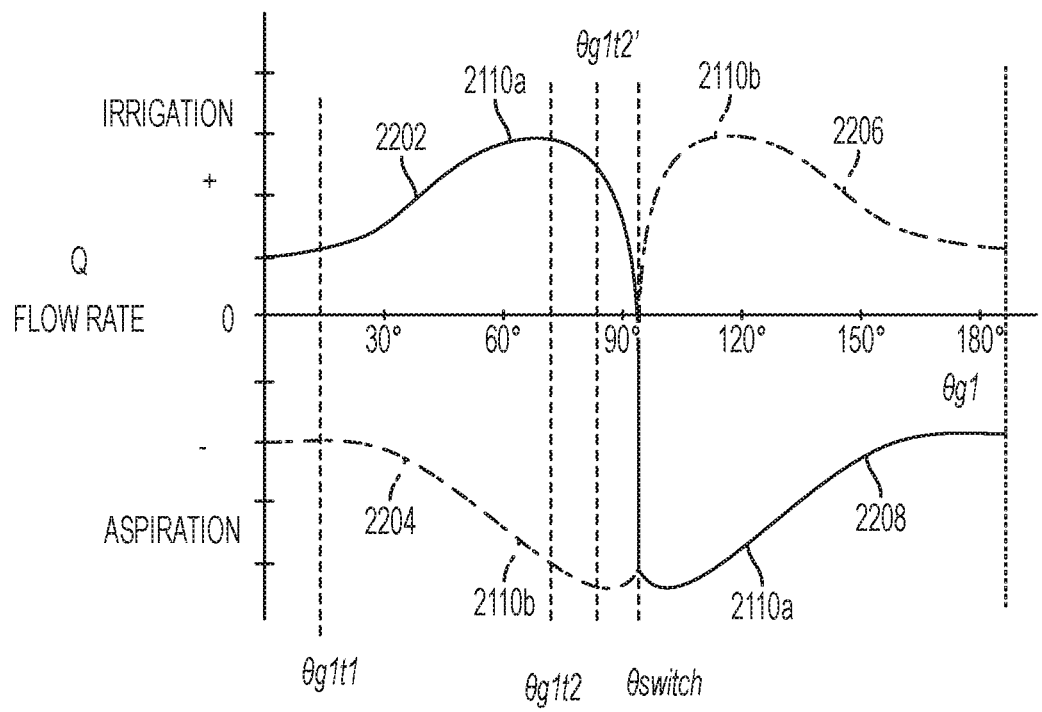
FIG. 22 shows graphs illustrating variation of a flow rate and an aspiration rate of an irrigation fluid through the first and second ports of the end effector of FIGS. 21A-21C, as a function of the rotational angle of the end effector with respect to the ground.

FIG. 22 illustrates, in graphs 2202, 2204, 2206, 2208, a flow rate through the first and second ports 2110a, 2110b as a function of the angle $\theta g1$ with respect to the ground. In particular, the graph 2202 shows an irrigation flow rate of the first port 2110a operating as an irrigation port, the graph 2204 shows an aspiration flow rate of the second port 2110b operating as an aspiration port, the graph 2206 shows an irrigation flow rate of the second port 2110b operating as an irrigation port, and the graph 2208 shows an aspiration flow rate of the first port 2110b operating as an aspiration port.

As the rotational angle $\theta g1$ remains below a certain first threshold angle ($\theta g1t1$ in FIG. 22), the irrigation flow rate through the first port 2110a and the aspiration flow rate through the second port 2110b are each maintained at approximately the same respective values, as shown in the graphs 2202, 2204 in FIG. 22. In this example, the first threshold angle $\theta g1t1$ is about 15 degrees, though it should be appreciated that this is an exemplary value only. As the rotational angle $\theta g1$ exceeds the first threshold angle $\theta g1t1$, the control system causes the first irrigation flow rate and the first aspiration flow rate to increase, which occurs up to a certain second threshold value ($\theta g1t2$ in FIG. 22, about 70 degrees). It should be noted that, in FIG. 22, the second threshold value $\theta g1t2$ is shown in the graph 2202 for the flow rate through the first port 2110a that approximately follows a right-skewed bell-shaped curve. As shown in the graph 2204, in this example, the aspiration flow rate through the second port 2110b has another second threshold $\theta g1t2'$, greater than the second threshold value $\theta g1t2$. When the aspiration flow rate through the second port 2110b exceeds its second threshold $\theta g1t2'$, the aspiration flow rate decreases, as shown in the graph 2202. It should be appreciated that, in some embodiments, the irrigation fluid flow rate and the aspiration flow rate can have the same thresholds, or their values can be different from those shown in FIG. 22.

FIG. 21B shows the instrument shaft that has been rotated with respect to the ground G2 (clockwise, as in this example) such that the angle $\theta g1$ increases and the end effector 2106 becomes positioned at an angle relative to the ground G2 that is approximately equal to the threshold value $\theta g1t1$ (about 70 degrees, as shown in FIG. 22). As shown in FIG. 22, at this position, the first port 2110a operates as the irrigation port delivering an irrigation fluid at a greater irrigation flow rate than the flow rate through the first port 2110a in FIG. 21A. Similarly, the second port 2110b shown in FIG. 21B aspirates fluids at an aspiration rate that is greater than the aspiration rate through the second port 2110b in FIG. 21A.

The respective flow rates through the first and second ports 2110a, 2110b are increased until the angle exceeds the second threshold angles $\theta g1t2$, $\theta g1t2'$, at which point the irrigation flow rate through the first port 2110a decreases and the aspiration rate through the second port 2110b decreases, as shown in the graphs 2202. 2204. As shown in FIG. 22, as the instrument shaft is rotated further and reaches a switch threshold value $\theta switch$ (i.e. $\theta g1$ is about 90 degrees, in this example), the functions of the first and second ports switch such that the first port 2110a becomes operating as an aspiration port (the graph 2208) and the second port 2110b becomes operating as an irrigation port (the graph 2206).

As shown in FIG. 22, the graphs 2206, 2208 show a dependence of a flow rate from the angle $\theta g1$ proportionally to a dependence of the flow rate shown in the graphs 2202, 2204. In particular, in the graph 22206, the flow rate through the second port 2110b increases and then decreases, following approximately a left-skewed bell-like curve that mirrors the shape of the curve of the graph 2202. Similarly, the aspiration rate through the first port 2110a, shown in the graph 2208, also increases and then decreases, following approximately a left-skewed bell-like curve that mirrors the shape of the curve of the graph 2204. As shown in the graph 2208, the increase of the aspiration rate through the first port 2110a is at a greater rate than the increase in the flow rate through the second port 2110b (graph 2206). Also, the aspiration rate through the first port 2110a decreases at a greater rate than the decrease in the flow rate through the second port 2110b (graph 2206). As shown in the graphs 2206, 2208, when the rotational angle $\theta g1$ reaches a certain threshold, such as about 160 degrees, the respective flow rates through the first and second ports 2110a, 2110b are maintained at approximately the same respective constant values.

FIG. 21C shows the end effector 2106 after the first and second ports switched their "roles," such that the first port 2110a operates as an aspiration port and the second port 2110b operates as an irrigation port. In FIG. 21C, the ports are shown rotated 180 degrees with respect to their positions shown in FIG. 21A, such that the aspiration flow rate through the first port 2110a is relatively low and the irrigation fluid flow rate through the second port 2110b is also relatively low, in accordance with the graphs 2208, 2206 in FIG. 22.

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers.

A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 23:
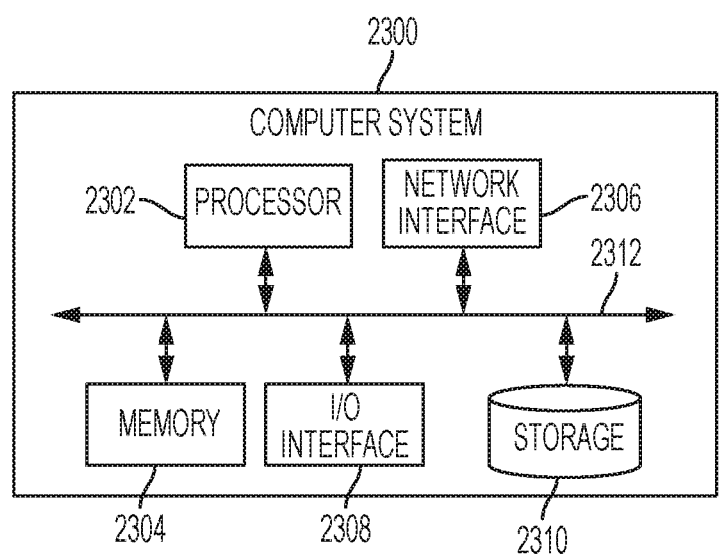
FIG. 23 illustrates one exemplary embodiment of a computer system that can be used to implement a control system of the present disclosure.

FIG. 23 illustrates one exemplary embodiment of a computer system 2300. As shown, the computer system 2300 includes one or more processors 2302 which can control the operation of the computer system 2300. "Processors" are also referred to herein as "controllers." The processor(s) 2302 can include any type of microprocessor or central processing unit (CPU), including programmable general-purpose or special-purpose microprocessors and/or any one of a variety of proprietary or commercially available single or multi-processor systems. The computer system 2300 can also include one or more memories 2304, which can provide temporary storage for code to be executed by the processor(s) 2302 or for data acquired from one or more users, storage devices, and/or databases. The memory 2304 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 2300 can be coupled to a bus system 2312. The illustrated bus system 2312 is an abstraction that represents any one or more separate physical busses, communication lines/interfaces, and/or multi-drop or point-to-point connections, connected by appropriate bridges, adapters, and/or controllers. The computer system 2300 can also include one or more network interface(s) 2306, one or more input/output (IO) interface(s) 2308 that can include one or more interface components, and one or more storage device(s) 2310.

The network interface(s) 2306 can enable the computer system 2300 to communicate with remote devices, e.g., motor(s) coupled to the drive system 257 that is located within the surgical device or a robotic surgical system or other computer systems, over a network, and can be, for non-limiting example, remote desktop connection interfaces, Ethernet adapters, and/or other local area network (LAN) adapters. The 10 interface(s) 2308 can include one or more interface components to connect the computer system 2300 with other electronic equipment, such as the sensors located on the motor(s). For non-limiting example, the 10 interface(s) 2308 can include high speed data ports, such as universal serial bus (USB) ports, 1394 ports, Wi-Fi, Bluetooth, etc. Additionally, the computer system 2300 can be accessible to a human user, and thus the 10 interface(s) 2308 can include displays, speakers, keyboards, pointing devices, and/or various other video, audio, or alphanumeric interfaces. The storage device(s) 2310 can include any conventional medium for storing data in a non-volatile and/or non-transient manner. The storage device(s) 2310 can thus hold data and/or instructions in a persistent state, i.e., the value(s) are retained despite interruption of power to the computer system 2300. The storage device(s) 2310 can include one or more hard disk drives, flash drives, USB drives, optical drives, various media cards, diskettes, compact discs, and/or any combination thereof and can be directly connected to the computer system 2300 or remotely connected thereto, such as over a network. In an exemplary embodiment, the storage device(s) 2310 can include a tangible or non-transitory computer readable medium configured to store data, e.g., a hard disk drive, a flash drive, a USB drive, an optical drive, a media card, a diskette, a compact disc, etc.

The elements illustrated in FIG. 23 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 2300 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 2300 can also include a web server for generating and/or delivering the web pages to client computer systems.

In an exemplary embodiment, the computer system 2300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   a surgical tool, comprising:
      a shaft having an end effector at a distal end thereof and a first treatment electrode and a second treatment electrode associated with the end effector, an aspiration tube extending through the shaft with a center of the aspiration tube arranged at a first position within the shaft and having an inlet port at a distal end thereof, wherein the aspiration tube is extendible and retractable with respect to the first and the second treatment electrode, and an irrigation tube extending through the shaft with a center of the irrigation tube arranged at a second position within the shaft and having an outlet port in proximity to the first and the second treatment electrode, the irrigation tube being in fluid communication with a fluid source, wherein the aspiration tube and the irrigation tube are non-concentrically arranged such that the first position and the second position are radially offset from one another, and the first treatment electrode and the second treatment electrode are arranged between the aspiration tube and the irrigation tube within the shaft; and
      a housing operably connected to the shaft, the housing having a pump in fluid communication with the irrigation tube, the pump having at least one first rotatable element configured to be selectively driven to actuate the pump; and
      a plurality of motors configured to be operably connected to the housing, a first motor of the motors being configured to selectively drive the first rotatable element of the pump to control a flow rate of a fluid delivered through the irrigation tube.

2. The surgical system of claim 1, wherein the housing further includes a second rotatable element configured to be selectively driven by a second motor of the motors to control extension and retraction of the aspiration tube.

3. The surgical system of claim 2, wherein the housing further has a third rotatable element configured to be selectively driven to cause articulation of the end effector with respect to the shaft, and the housing further has a fourth rotatable element configured to be selectively driven to cause rotation of the shaft about a longitudinal axis thereof.

4. The surgical system of claim 3, further comprising an electrosurgical generator configured to provide electrosurgical energy to the first and the second treatment electrode and configured to be controlled by the control system.

5. The surgical system of claim 4, wherein the PID controller is configured to output the current control value to the first motor such that the flow rate of the fluid increases when the tissue impedance increases.

6. The surgical system of claim 4, wherein the flow rate set point is determined based on desired power to be applied by the first and the second treatment electrodes to a tissue to cause a desired effect on the tissue.

7. The surgical system of claim 6, wherein the control system is configured to control the fifth motor such that the vacuum source increases the aspiration rate as the impedance increases, and the pump increases the flow rate of the fluid such that an increase in the flow rate occurs with a predetermined delay and proportionate to an increase in the aspiration rate.

8. The surgical system of claim 7, wherein the control system is configured to increase the power when the tilting angle exceeds a predetermined value.

9. The surgical system of claim 3, wherein the control system comprises a proportional-integral-derivative (PID) controller that is configured to output a current control value to the first motor based on a difference between a flow rate set point and an actual flow rate, wherein the actual flow rate is determined based on tissue impedance and the flow rate set point is determined based on a power set point.

10. The surgical system of claim 3, further comprising a vacuum source in fluid communication with the aspiration tube and controlled by a fifth motor of the motors, wherein the control system is configured to:
    control the fifth motor to selectively drive the vacuum source to adjust, based on measured tissue impedance, an aspiration rate of fluid aspirated through the aspiration tube, and
    control the first motor to selectively drive the first rotatable element to actuate the pump to adjust the flow rate of the fluid based on the aspiration rate.

11. The surgical system of claim 3, wherein the control system is configured to control power provided by an electrosurgical generator to the first and the second electrodes, based on a tilting angle of the first and the second electrodes with respect to a gravity vector.

12. The surgical system of claim 1, wherein the first and the second treatment electrodes are configured to apply radiofrequency (RF) energy to tissue.

13. The surgical system of claim 1, wherein the system is a surgical robotic system having a tool driver assembly configured to operably mate with the housing, the surgical robotic system being associated with a control system.

14. A surgical system, comprising:
an electromechanical device including an instrument shaft and an end effector formed at a distal end thereof and first and second treatment electrodes associated with the end effector;
an aspiration tube extending through the shaft with a center of the aspiration tube arranged at a first position within the shaft and having an inlet port in proximity to the electrodes, the aspiration tube being in fluid communication with a vacuum source, and the aspiration tube being extendible and retractable with respect to the first and second treatment electrodes;
an irrigation tube extending through the shaft with a center of the irrigation tube arranged at a second positions within the shaft and having an outlet port in proximity to the electrodes, the irrigation tube being in fluid communication with a fluid source, wherein the aspiration tube and the irrigation tube are non-concentrically arranged such that the first position and the second position are radially offset from one another, and the first treatment electrode and the second treatment electrode are arrant ed between the aspiration tub and the irrigation tube within the shaft;
a housing coupled proximally to the shaft, the housing comprising a pump operably coupled to the irrigation tube, the housing being configured to operably connect to a tool drive assembly of a robotic surgical system; and
a control system configured to control a flow rate of an irrigation fluid delivered through the outlet port of the irrigation tube based on power received by the electrodes.

15. The surgical system of claim 14, wherein the control system is configured to control the flow rate by controlling an aspiration rate of fluid aspirated through the inlet port of the aspiration tube based on the power, and by controlling the flow rate based on the controlled aspiration rate.

16. The surgical system of claim 14, wherein the control system is configured to control the flow rate based on monitoring the power by monitoring a deviation of the power from a power set point.

17. A method of treating tissue, comprising:
actuating a power generator to deliver power to a tissue at a treatment site through first and second electrodes of an electrosurgical tool operably coupled to the power generator;
monitoring impedance of the tissue as the electrical energy is applied to the tissue to determine a deviation of actual power from a power set point; and
controlling a flow rate of an irrigation fluid provided to the treatment site by an irrigation tube extending through a shaft and having a center of the irrigation tube arranged at a first position in fluid communication with a pump, the flow rate being controlled based on the monitored impedance;
controlling an aspiration rate of a fluid aspirated from the treatment site by an aspiration tube extending through the shaft and having a center of the aspiration tube arranged at a second position that is extendable and retractable with respect to the first and second electrodes, wherein the irrigation tube and the aspiration tube are non-concentrically arranged such that the first position and the second position are radially offset from one another, and the first treatment electrode and the second electrode are arranged between the aspiration tube and the irrigation tube within the shaft.

18. The method of claim 17, further comprising controlling the flow rate of the irrigation fluid when it is determined that the first and the second electrodes are in contact with the tissue.

19. The method of claim 17, further comprising controlling the power generator to
cease power delivery through the electrodes when the monitored impedance exceeds a predetermined impedance maximum, and
resume power delivery if the monitored impedance remains above the predetermined impedance maximum for a predetermined time period.

20. The method of claim 17, wherein the aspiration tube is in proximity to the electrodes such that the aspiration rate is increased in response to an increase in the monitored impedance, and further controlling the flow rate such that the flow rate increases proportionate to an increase in the aspiration rate.

* * * * *